(12) United States Patent
Birk

(10) Patent No.: US 9,155,650 B2
(45) Date of Patent: Oct. 13, 2015

(54) BARIATRIC DEVICE AND METHOD FOR WEIGHT LOSS

(75) Inventor: Janel Birk, Oxnard, CA (US)

(73) Assignee: APOLLO ENDOSURGERY, INC., Austin, TX (US)

(*) Notice: Subject to any disclaimer, the term of this patent is extended or adjusted under 35 U.S.C. 154(b) by 456 days.

(21) Appl. No.: 13/635,332

(22) PCT Filed: Mar. 15, 2011

(86) PCT No.: PCT/US2011/028565
§ 371 (c)(1),
(2), (4) Date: Sep. 14, 2012

(87) PCT Pub. No.: WO2011/116025
PCT Pub. Date: Sep. 22, 2011

(65) Prior Publication Data
US 2013/0013084 A1    Jan. 10, 2013

Related U.S. Application Data

(60) Provisional application No. 61/314,131, filed on Mar. 15, 2010, provisional application No. 61/407,430, filed on Oct. 27, 2010.

(51) Int. Cl.
*A61B 19/00* (2006.01)
*A61F 5/00* (2006.01)

(52) U.S. Cl.
CPC ............. *A61F 5/0076* (2013.01); *A61F 5/0079* (2013.01)

(58) Field of Classification Search
CPC ...................................................... A61F 5/006
USPC ............................................................ 604/8, 9
See application file for complete search history.

(56) References Cited

U.S. PATENT DOCUMENTS

| 4,416,267 A | 11/1983 | Garren et al. |
| 4,607,618 A | 8/1986 | Angelchik |
| 4,648,383 A | 3/1987 | Angelchik |
| 4,739,758 A | 4/1988 | Lai et al. |
| 4,774,956 A | 10/1988 | Kruse et al. |
| 4,844,068 A | 7/1989 | Arata et al. |
| 4,899,747 A | 2/1990 | Garren et al. |

(Continued)

FOREIGN PATENT DOCUMENTS

| DE | 102007025312 | 11/2008 |
| EP | 1397998 | 3/2004 |

(Continued)

*Primary Examiner* — Leslie Deak
(74) *Attorney, Agent, or Firm* — Gordon & Jacobson, PC

(57) ABSTRACT

A bariatric device 10 for use in inducing weight loss, comprising a lower stomach element 26 which contacts the lower stomach at least intermittently to produce a satiety signal to the user, giving a feeling of fullness and reducing hunger. The lower stomach element 26 may be combined with a positional element 25 extending into the upper stomach to maintain the device's position for at least intermittent contact with the lower stomach. Alternatively, first and second elements 12, 13 may be symmetrically attached to the positioning element 25, so that the device can orient itself either way in the stomach. The lower stomach, first, or second elements 26, 12, 13 may have a restriction element to slow gastric filling or emptying, to produce a satiety signal. In any of the embodiments, the bariatric device may be adjustable, either manually, automatically or remotely, to optimally size and/or position the device.

26 Claims, 38 Drawing Sheets

(56) References Cited

U.S. PATENT DOCUMENTS

| | | | |
|---|---|---|---|
| 4,925,446 | A | 5/1990 | Garay et al. |
| 5,259,399 | A | 11/1993 | Brown |
| 5,312,343 | A | 5/1994 | Krog et al. |
| 5,820,584 | A | 10/1998 | Crabb |
| 6,264,700 | B1 | 7/2001 | Kilcoyne et al. |
| 6,322,538 | B1 | 11/2001 | Elbert et al. |
| 6,454,785 | B2 | 9/2002 | De Hoyos Garza |
| 6,540,789 | B1 | 4/2003 | Silverman et al. |
| 6,579,301 | B1 | 6/2003 | Bales et al. |
| 6,675,809 | B2 * | 1/2004 | Stack et al. ........... 128/898 |
| 6,733,512 | B2 | 5/2004 | McGhan |
| 6,845,776 | B2 | 1/2005 | Stack et al. |
| 6,981,978 | B2 | 1/2006 | Gannoe |
| 6,981,980 | B2 | 1/2006 | Sampson et al. |
| 6,994,095 | B2 | 2/2006 | Burnett |
| 7,008,419 | B2 | 3/2006 | Shadduck |
| 7,033,384 | B2 | 4/2006 | Gannoe et al. |
| 7,037,344 | B2 | 5/2006 | Kagan et al. |
| 7,056,305 | B2 | 6/2006 | Garza Alvarez |
| 7,090,699 | B2 | 8/2006 | Geitz |
| 7,214,233 | B2 | 5/2007 | Gannoe et al. |
| 7,220,237 | B2 | 5/2007 | Gannoe et al. |
| 7,220,284 | B2 | 5/2007 | Kagan et al. |
| 7,223,277 | B2 | 5/2007 | DeLegge |
| 7,320,696 | B2 | 1/2008 | Gazi et al. |
| 7,347,875 | B2 | 3/2008 | Levine et al. |
| 7,354,454 | B2 | 4/2008 | Stack et al. |
| 7,476,256 | B2 | 1/2009 | Meade et al. |
| 7,510,559 | B2 | 3/2009 | Deem et al. |
| 7,608,114 | B2 | 10/2009 | Levine et al. |
| 7,682,330 | B2 | 3/2010 | Meade et al. |
| 7,695,446 | B2 | 4/2010 | Levine et al. |
| 7,699,863 | B2 | 4/2010 | Marco et al. |
| 7,753,870 | B2 * | 7/2010 | Demarais et al. ........... 604/8 |
| 7,771,382 | B2 | 8/2010 | Levine et al. |
| 7,794,447 | B2 | 9/2010 | Dann et al. |
| 7,815,589 | B2 | 10/2010 | Meade et al. |
| 7,837,643 | B2 | 11/2010 | Levine et al. |
| 7,841,503 | B2 | 11/2010 | Sonnenschein et al. |
| 7,931,693 | B2 | 4/2011 | Binmoeller |
| 7,981,162 | B2 | 7/2011 | Stack et al. |
| 8,029,455 | B2 | 10/2011 | Stack et al. |
| 8,032,223 | B2 | 10/2011 | Imran |
| 2003/0109935 | A1 | 6/2003 | Geitz |
| 2003/0153905 | A1 | 8/2003 | Edwards et al. |
| 2004/0044357 | A1 | 3/2004 | Gannoe et al. |
| 2004/0092892 | A1 | 5/2004 | Kagan et al. |
| 2004/0117031 | A1 | 6/2004 | Stack et al. |
| 2004/0122452 | A1 | 6/2004 | Deem et al. |
| 2004/0122453 | A1 | 6/2004 | Deem et al. |
| 2005/0049718 | A1 | 3/2005 | Dann et al. |
| 2005/0055039 | A1 | 3/2005 | Burnett et al. |
| 2005/0085923 | A1 | 4/2005 | Levine et al. |
| 2005/0096692 | A1 | 5/2005 | Linder et al. |
| 2005/0192614 | A1 | 9/2005 | Binmoeller |
| 2005/0197714 | A1 | 9/2005 | Sayet |
| 2005/0267595 | A1 | 12/2005 | Chen et al. |
| 2005/0267596 | A1 | 12/2005 | Chen et al. |
| 2005/0273060 | A1 | 12/2005 | Levy et al. |
| 2006/0178691 | A1 | 8/2006 | Binmoeller |
| 2006/0252983 | A1 | 11/2006 | Lembo et al. |
| 2007/0010864 | A1 | 1/2007 | Dann et al. |
| 2007/0016262 | A1 | 1/2007 | Gross et al. |
| 2007/0021761 | A1 | 1/2007 | Phillips |
| 2007/0078476 | A1 | 4/2007 | Hull, Sr. et al. |
| 2007/0083224 | A1 | 4/2007 | Hively |
| 2007/0100368 | A1 | 5/2007 | Quijano et al. |
| 2007/0118168 | A1 | 5/2007 | Lointier et al. |
| 2007/0156013 | A1 | 7/2007 | Birk |
| 2007/0173881 | A1 | 7/2007 | Birk et al. |
| 2007/0185374 | A1 * | 8/2007 | Kick et al. |
| 2007/0239284 | A1 | 10/2007 | Skerven et al. |
| 2007/0265598 | A1 | 11/2007 | Karasik |
| 2007/0293716 | A1 | 12/2007 | Baker et al. |
| 2008/0015618 | A1 | 1/2008 | Sonnenschein et al. |
| 2008/0058840 | A1 | 3/2008 | Albrecht et al. |
| 2008/0058887 | A1 | 3/2008 | Griffin et al. |
| 2008/0097513 | A1 | 4/2008 | Kaji et al. |
| 2008/0208241 | A1 | 8/2008 | Weiner et al. |
| 2008/0221595 | A1 | 9/2008 | Surti |
| 2008/0234718 | A1 | 9/2008 | Paganon et al. |
| 2008/0234834 | A1 | 9/2008 | Meade et al. |
| 2008/0243166 | A1 | 10/2008 | Paganon et al. |
| 2008/0249635 | A1 | 10/2008 | Weitzner et al. |
| 2008/0255678 | A1 | 10/2008 | Cully et al. |
| 2008/0262529 | A1 | 10/2008 | Jacques |
| 2009/0012553 | A1 | 1/2009 | Swain et al. |
| 2009/0082644 | A1 | 3/2009 | Li |
| 2009/0093767 | A1 | 4/2009 | Kelleher |
| 2009/0149879 | A1 | 6/2009 | Dillon |
| 2009/0198210 | A1 | 8/2009 | Burnett et al. |
| 2009/0259246 | A1 | 10/2009 | Eskaros et al. |
| 2009/0275973 | A1 | 11/2009 | Chen et al. |
| 2009/0287231 | A1 | 11/2009 | Brooks et al. |
| 2009/0299486 | A1 | 12/2009 | Shohat et al. |
| 2009/0312597 | A1 | 12/2009 | Bar et al. |
| 2010/0030017 | A1 | 2/2010 | Baker et al. |
| 2010/0049224 | A1 | 2/2010 | Vargas |
| 2010/0100115 | A1 | 4/2010 | Soetermans et al. |
| 2010/0121371 | A1 | 5/2010 | Brooks et al. |
| 2010/0168782 | A1 | 7/2010 | Hancock |
| 2010/0249822 | A1 | 9/2010 | Nihalani |
| 2010/0256775 | A1 | 10/2010 | Belhe et al. |
| 2010/0256776 | A1 | 10/2010 | Levine et al. |
| 2010/0305590 | A1 | 12/2010 | Holmes et al. |
| 2010/0331756 | A1 | 12/2010 | Meade et al. |

FOREIGN PATENT DOCUMENTS

| | | |
|---|---|---|
| EP | 1774929 | 4/2007 |
| FR | 2892297 | 4/2007 |
| FR | 2941617 | 8/2010 |
| WO | WO8800027 | 1/1988 |
| WO | WO0032092 | 6/2000 |
| WO | WO2005094257 | 10/2005 |
| WO | WO2005097012 | 10/2005 |
| WO | WO2005110280 | 11/2005 |
| WO | WO2006044640 | 4/2006 |
| WO | WO2006111961 | 10/2006 |
| WO | WO2006118744 | 11/2006 |
| WO | WO2007027812 | 3/2007 |
| WO | WO2007053556 | 5/2007 |
| WO | WO2007076021 | 7/2007 |
| WO | WO2007092390 | 8/2007 |
| WO | WO2007110866 | 10/2007 |
| WO | WO2008101048 | 8/2008 |
| WO | WO2008112894 | 9/2008 |
| WO | WO2008132745 | 11/2008 |
| WO | WO2010042062 | 4/2010 |
| WO | WO2010074712 | 7/2010 |
| WO | WO2010087757 | 8/2010 |
| WO | WO2010117641 | 10/2010 |

* cited by examiner

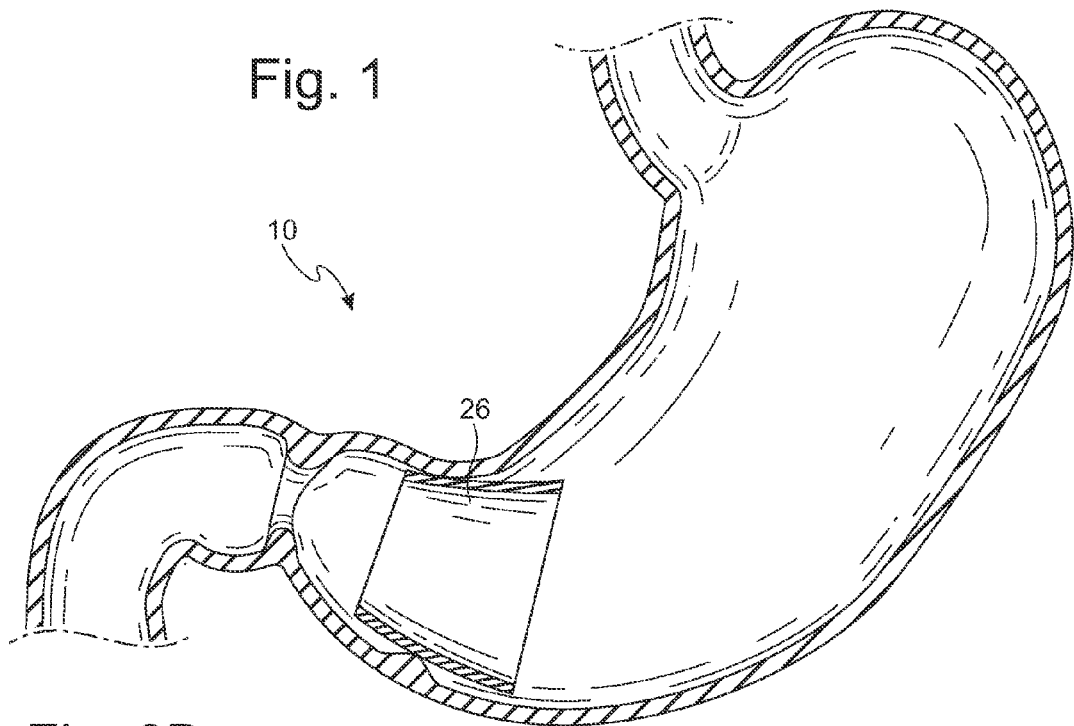
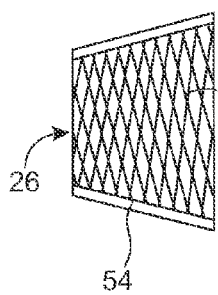
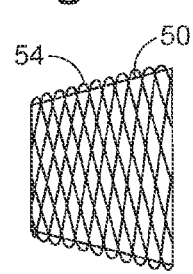
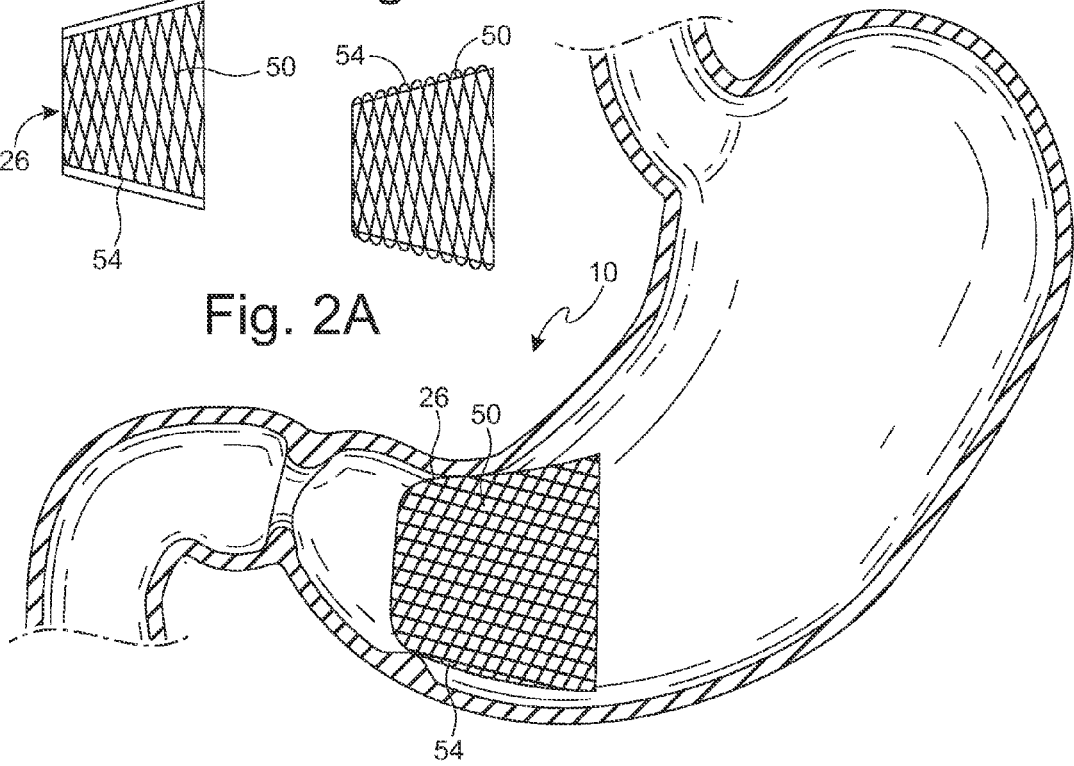

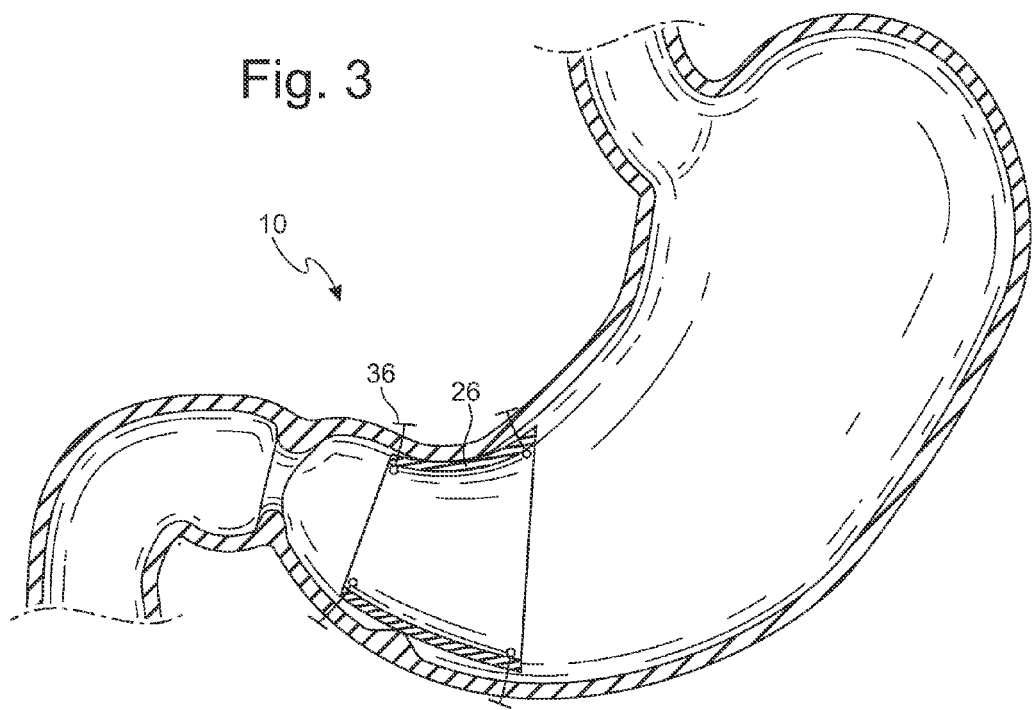
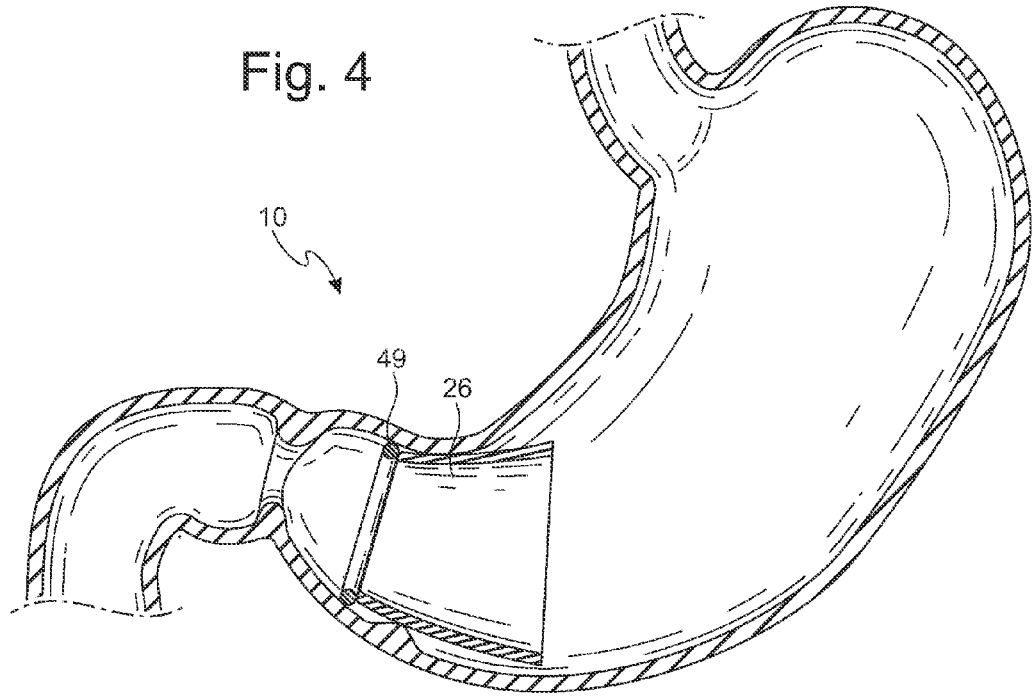

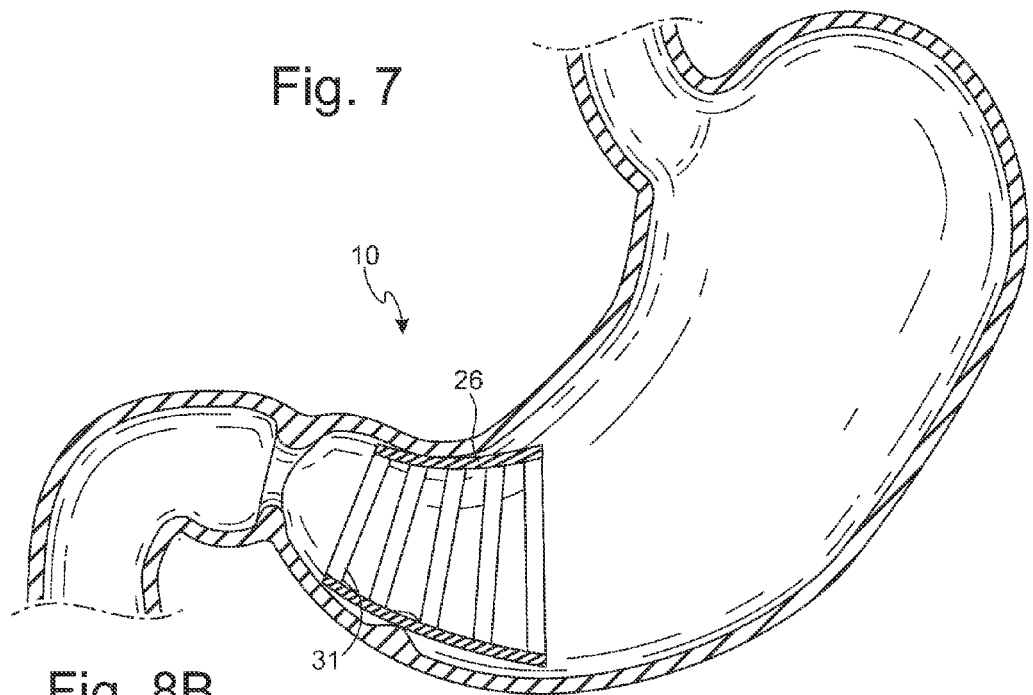
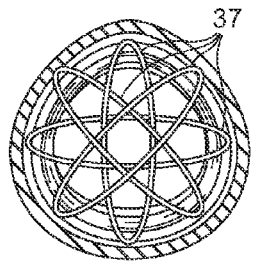
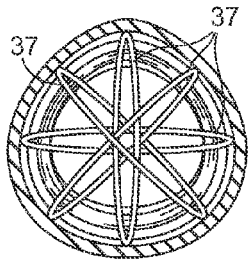
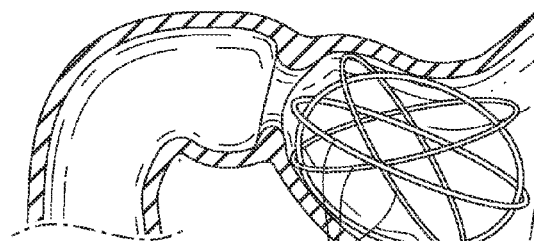

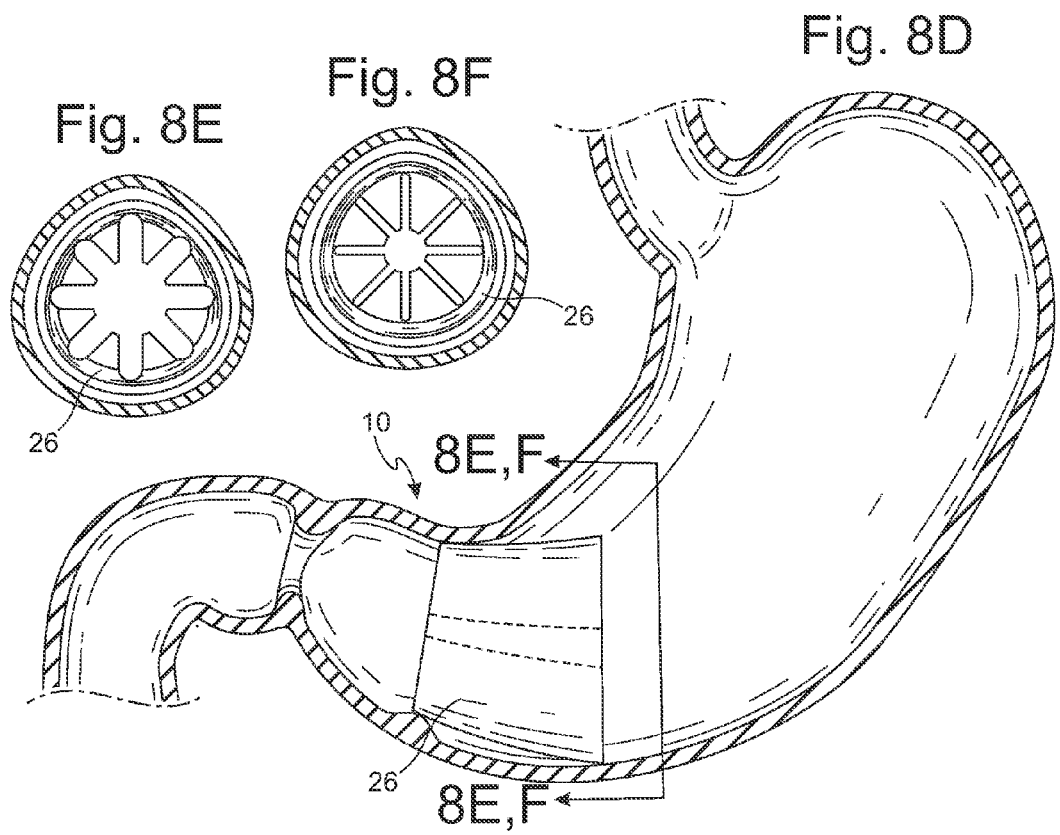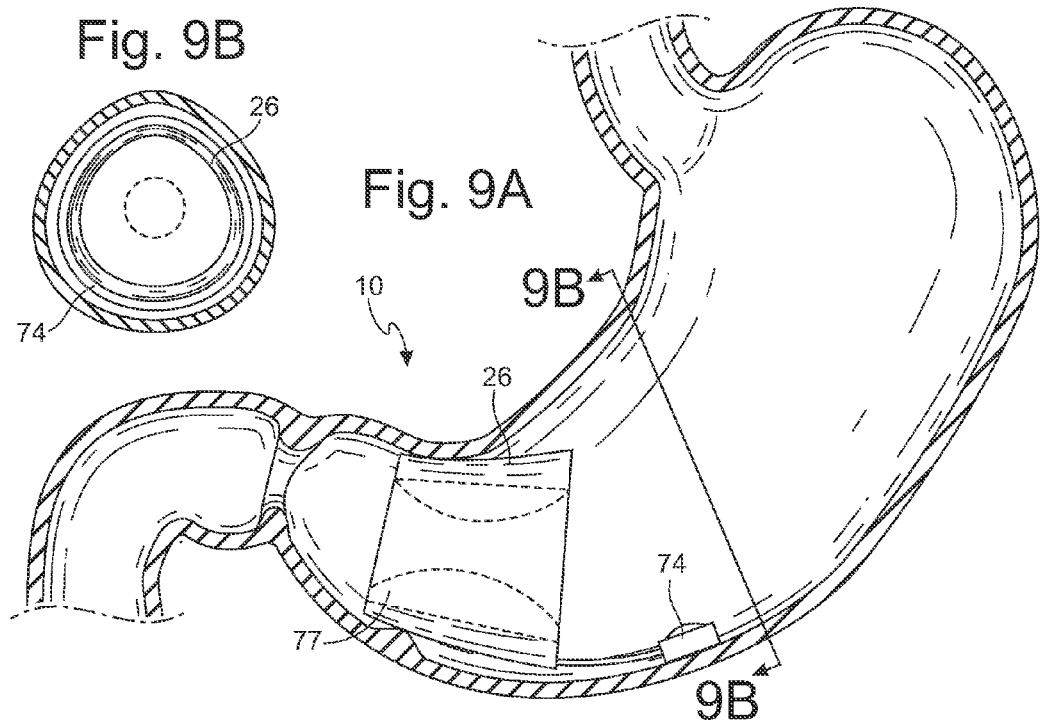

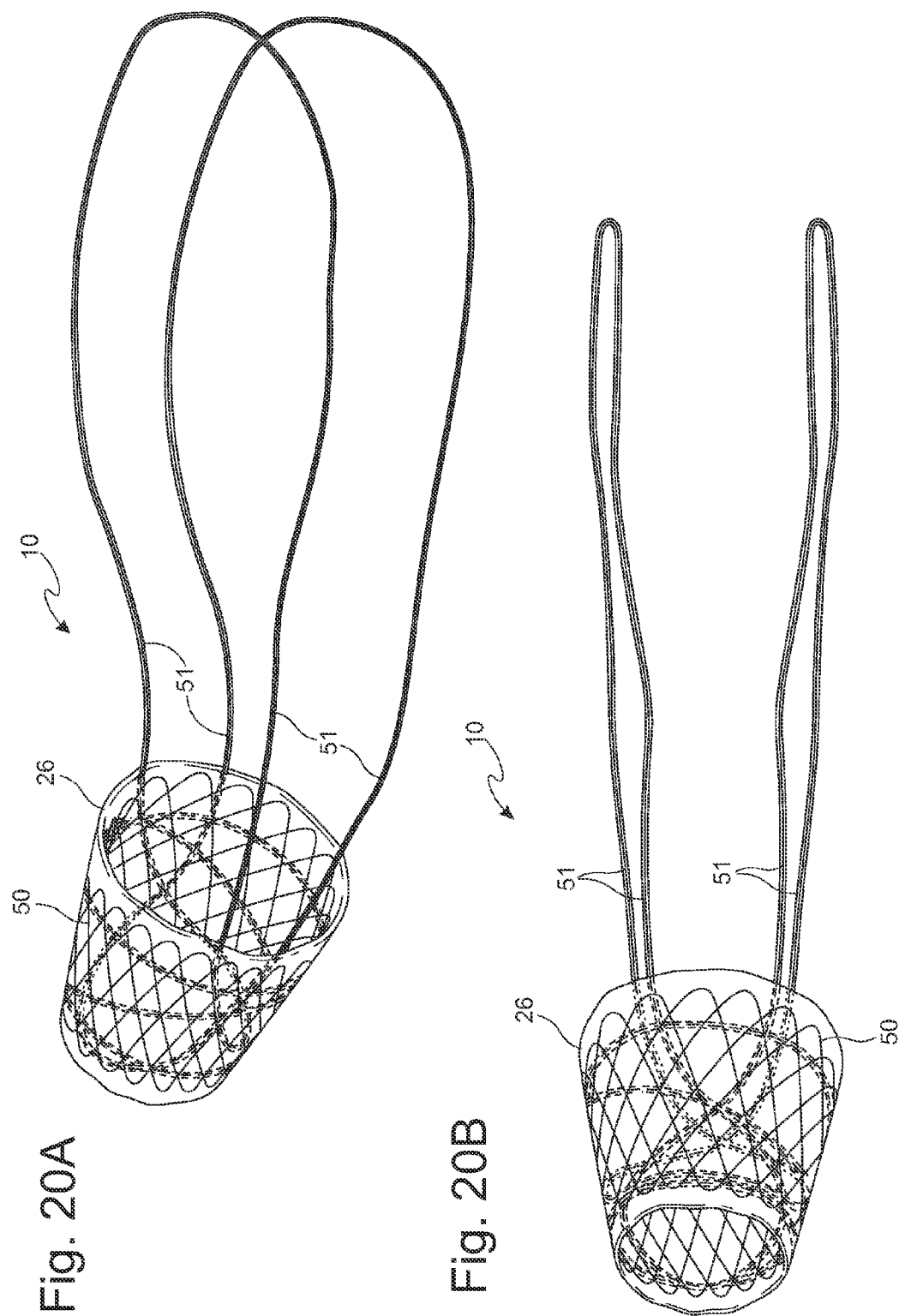

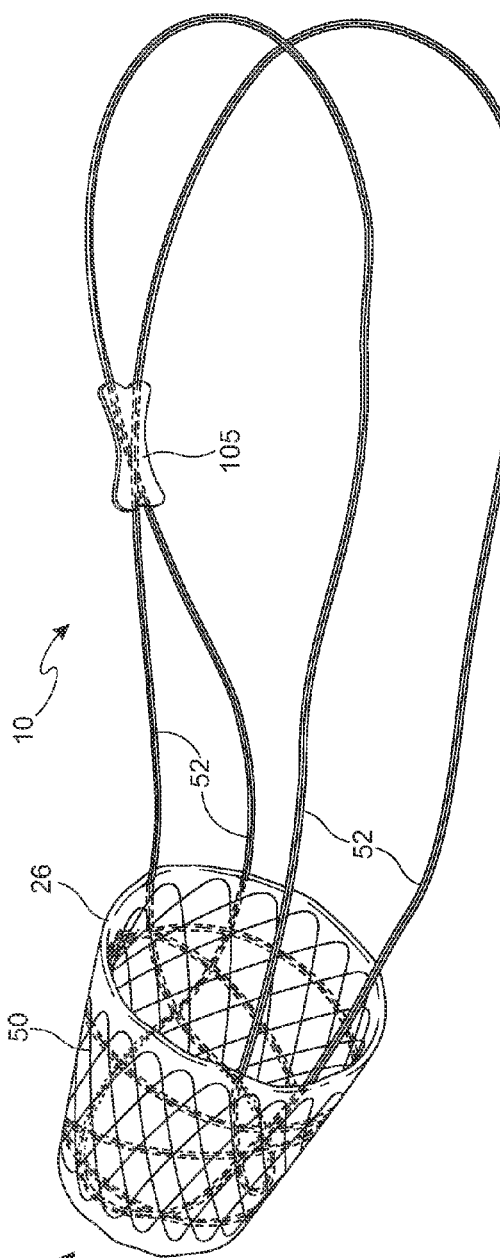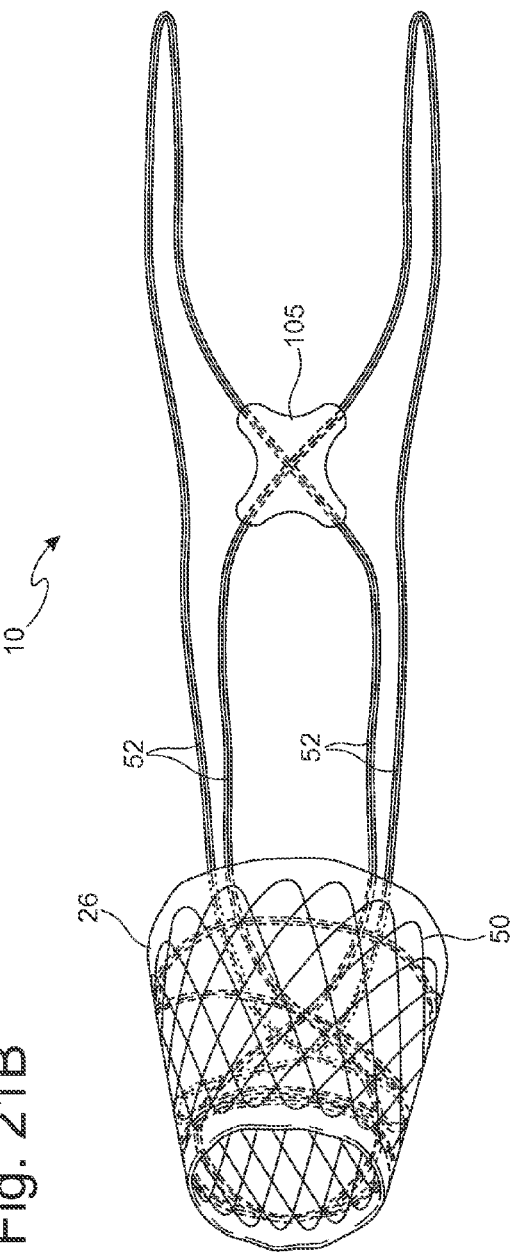

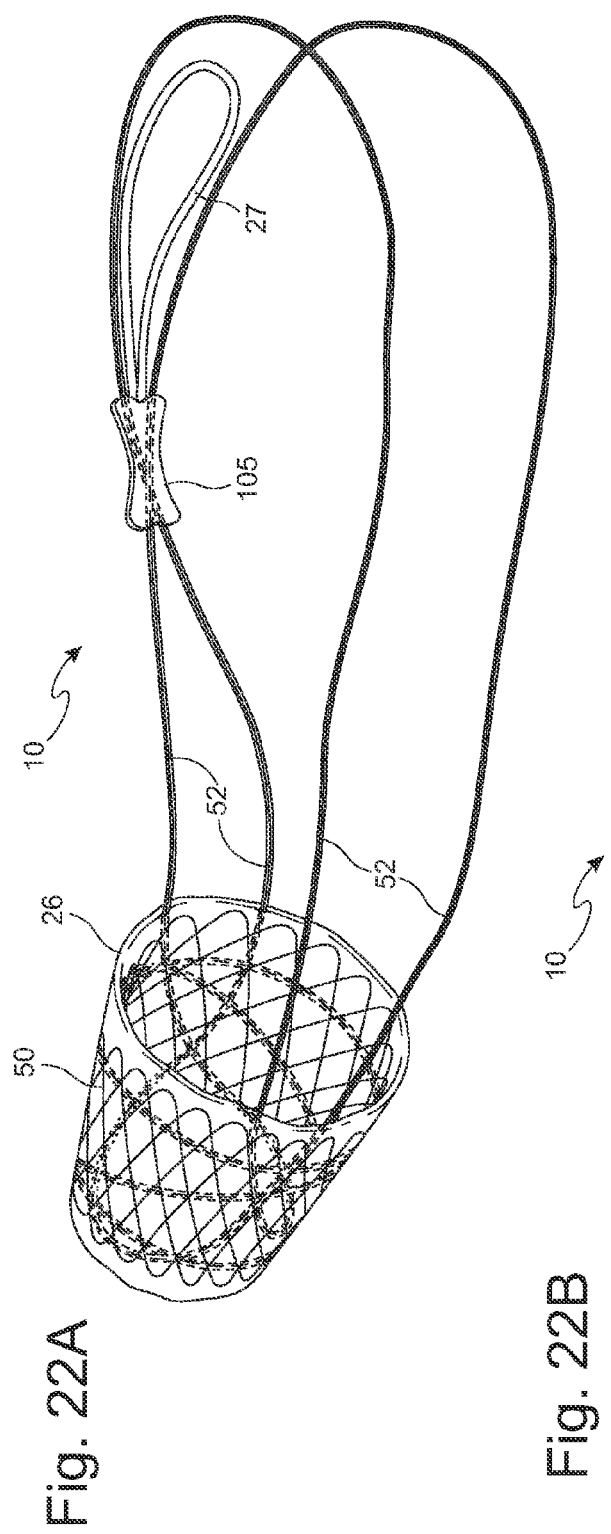
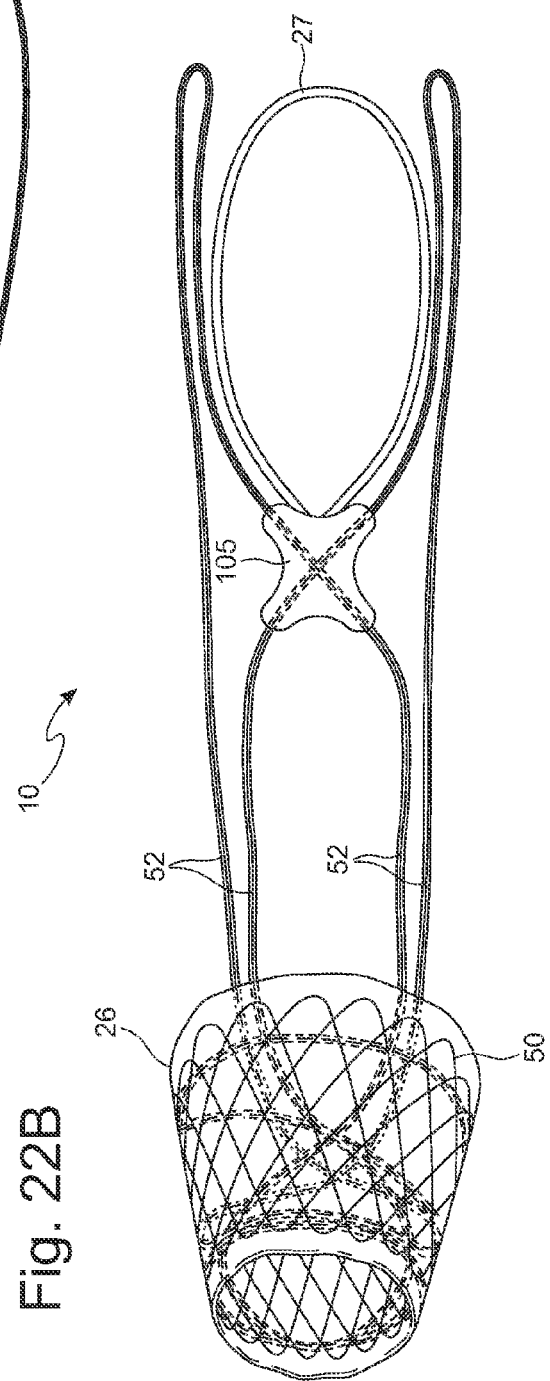
Fig. 22A
Fig. 22B

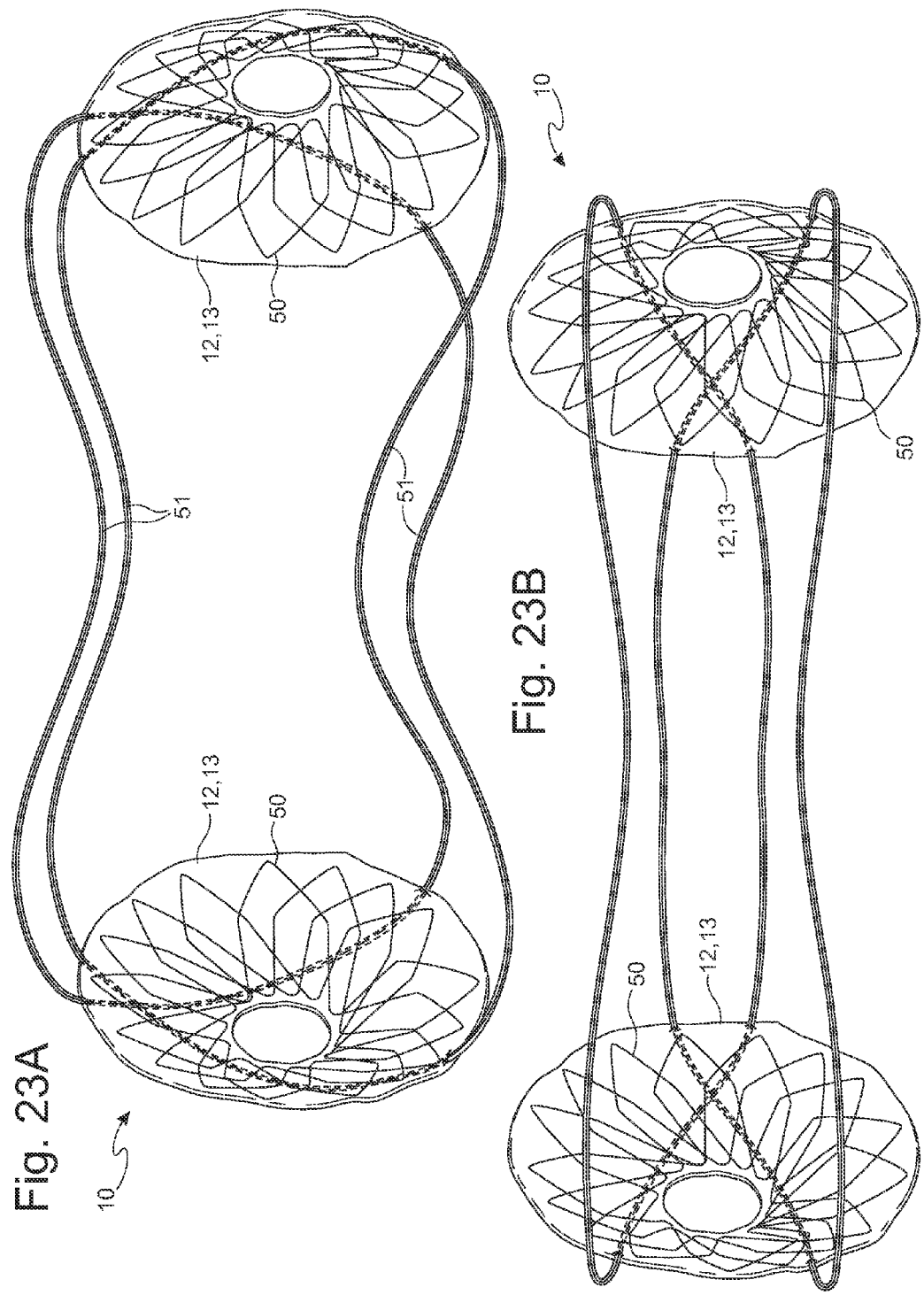

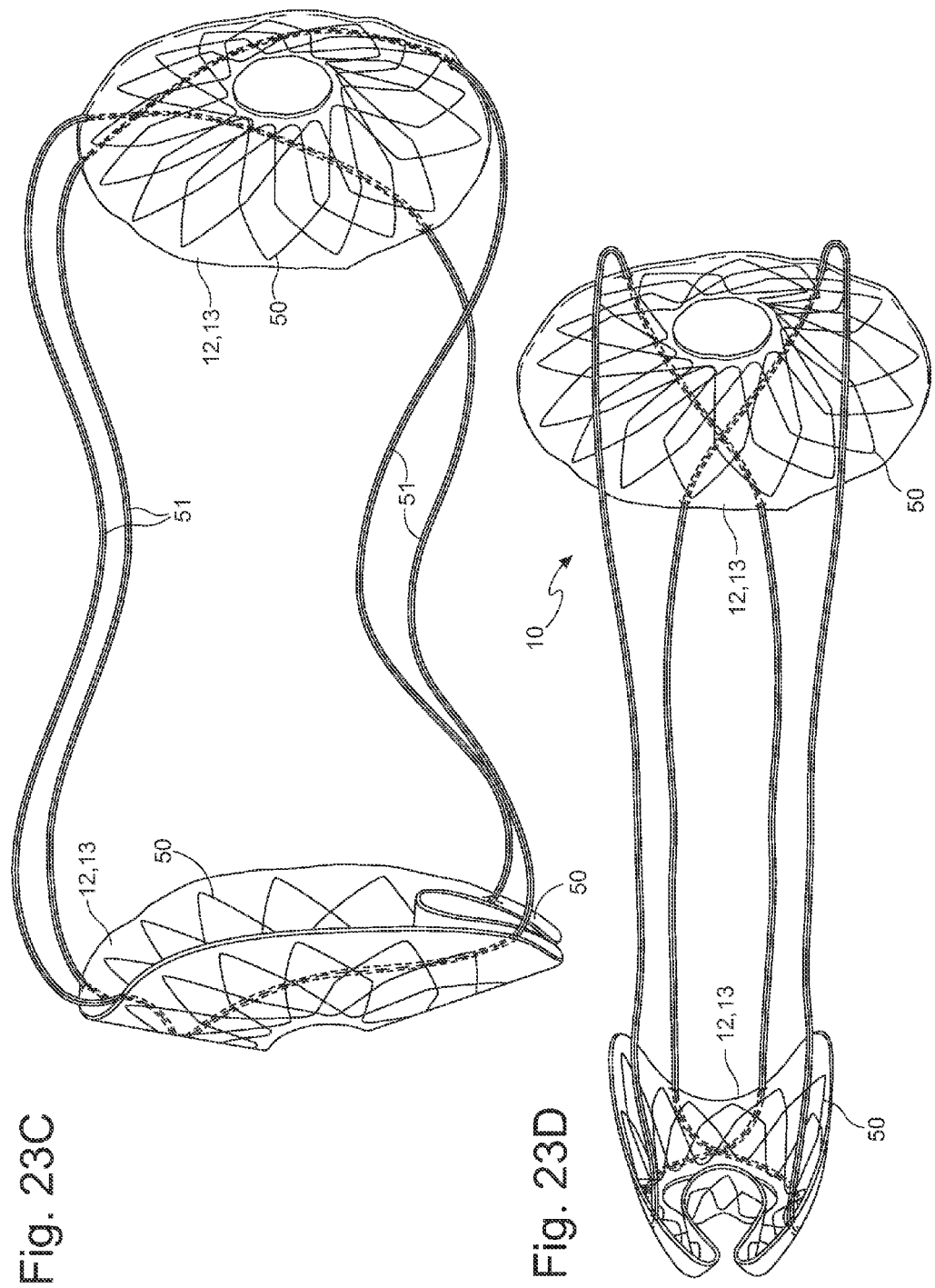

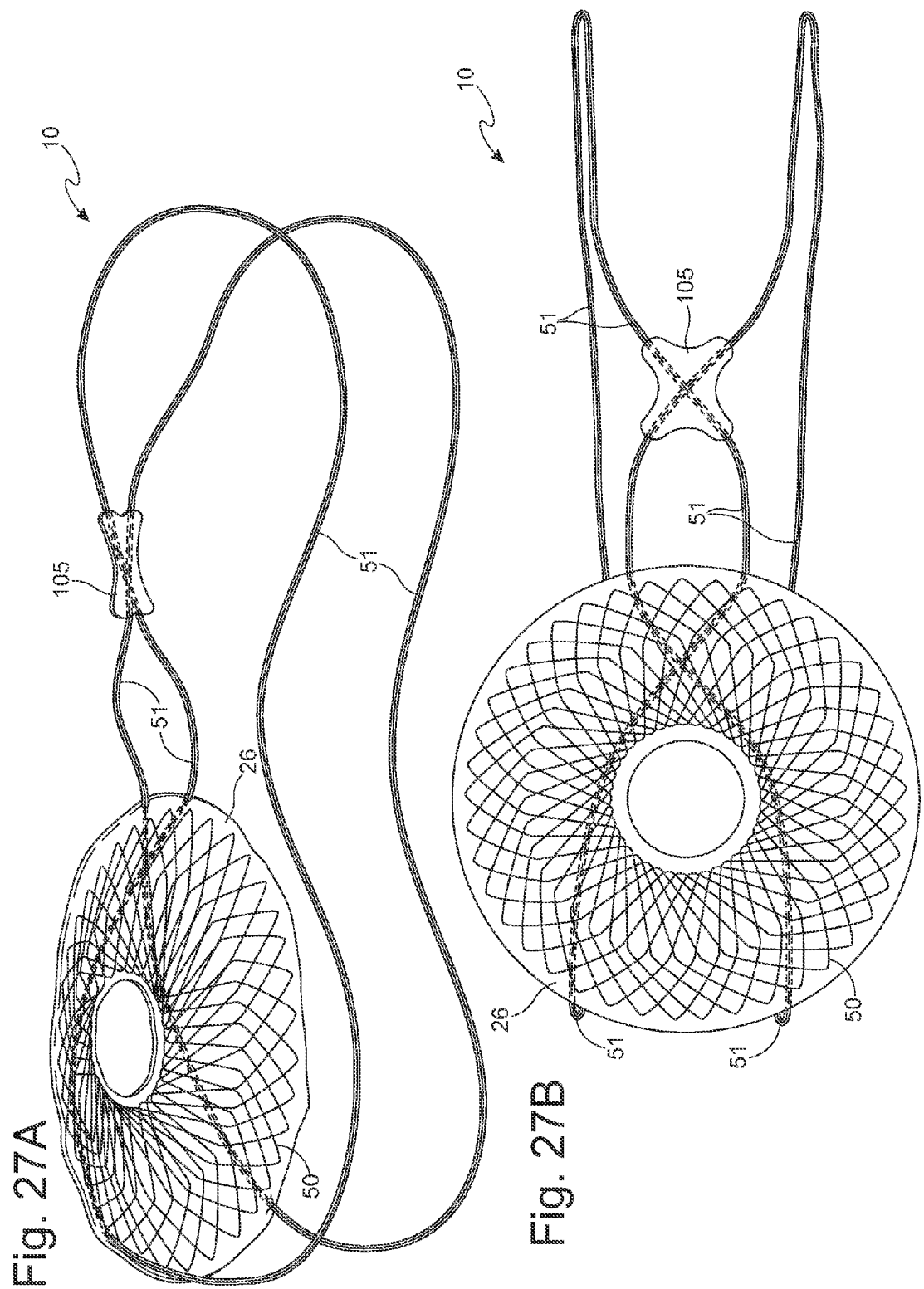

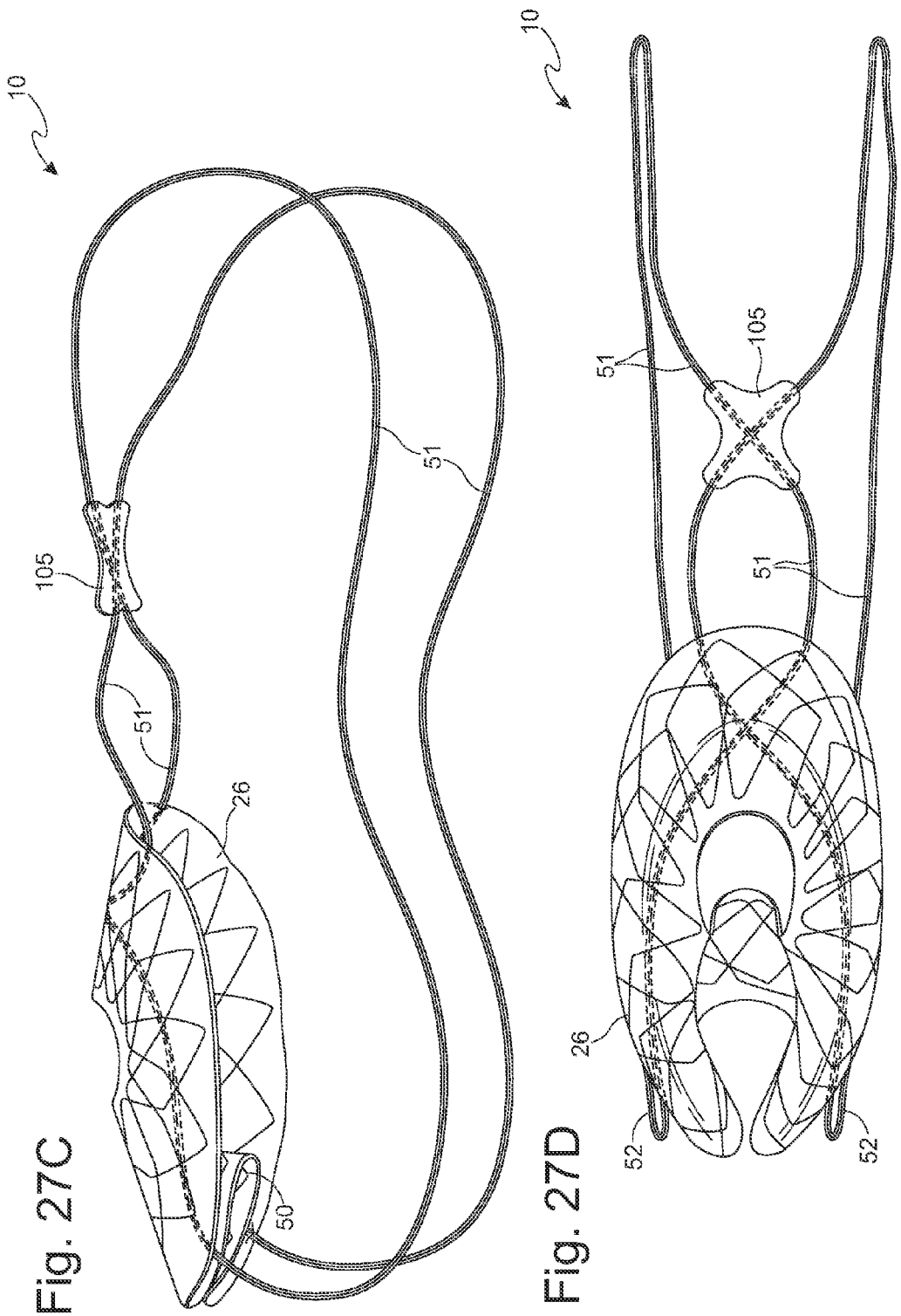

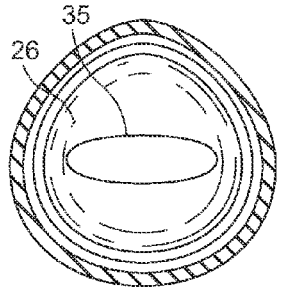
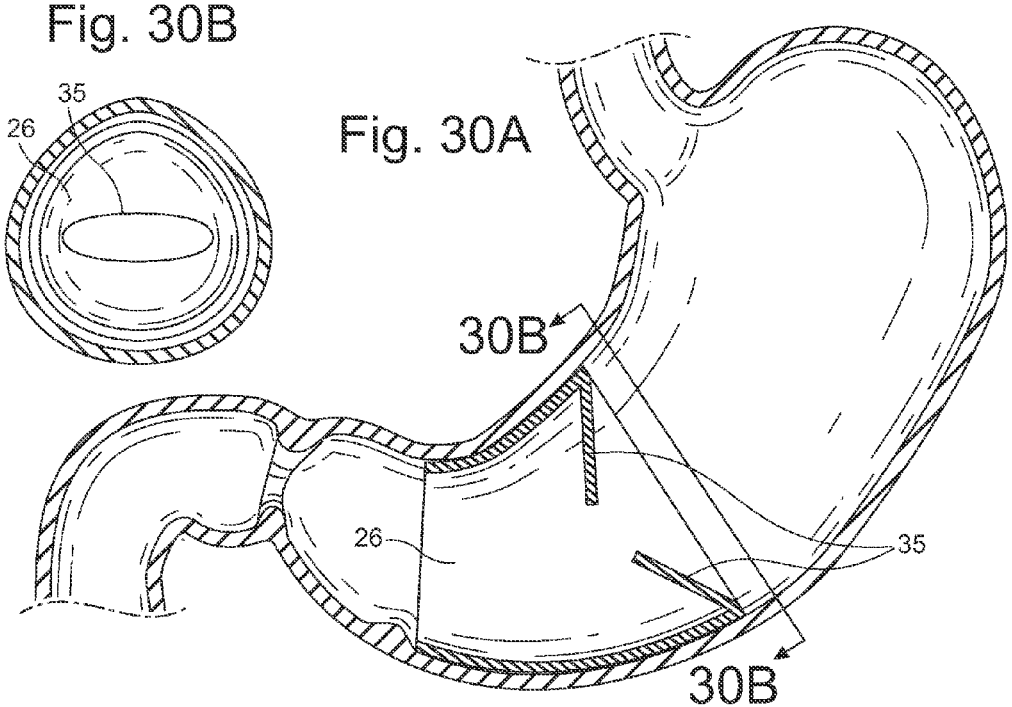
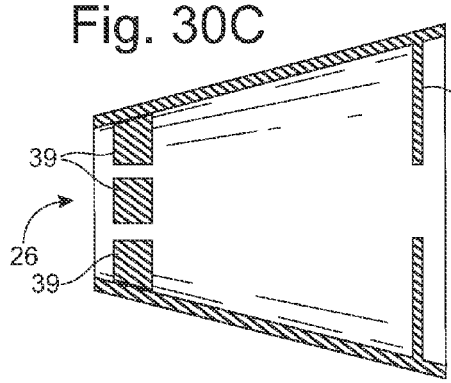
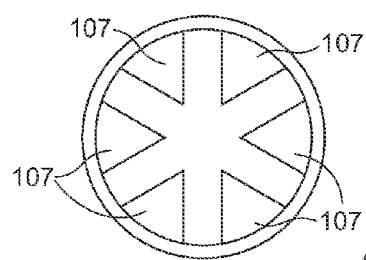
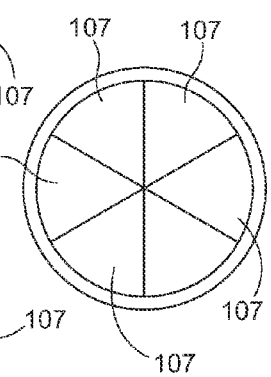
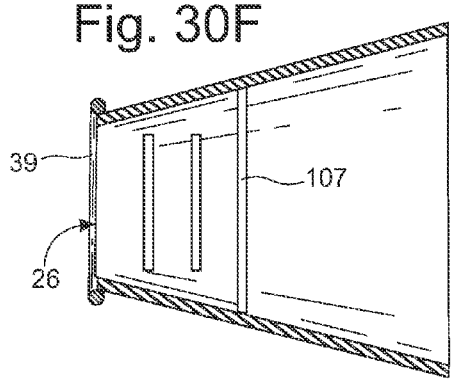
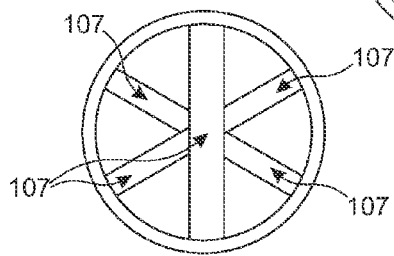

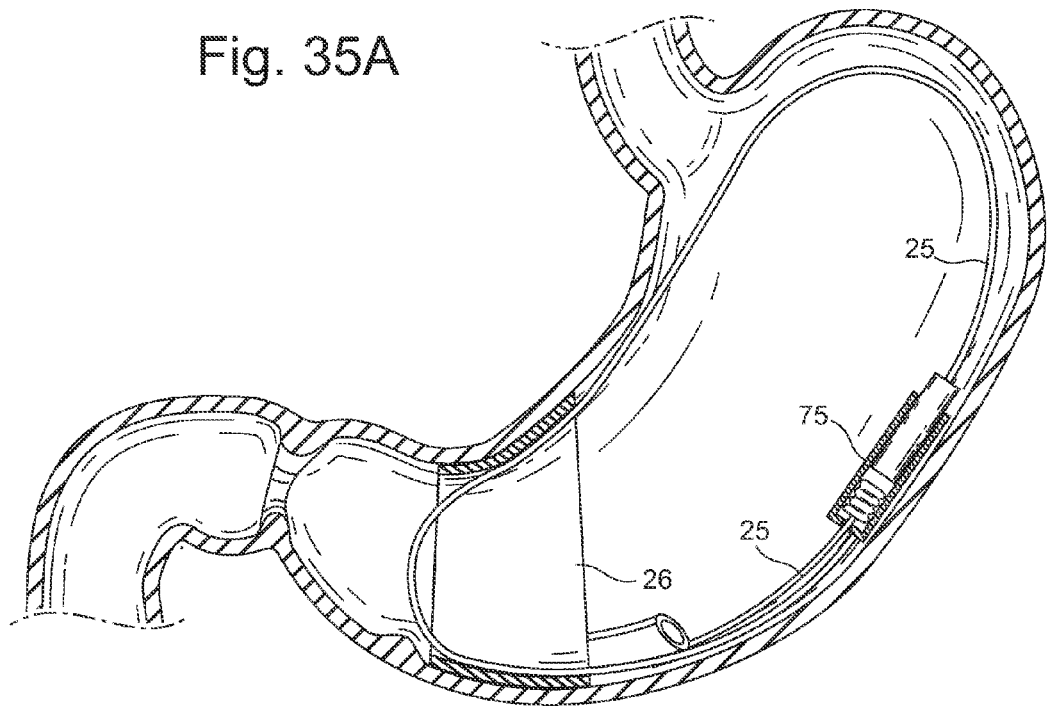
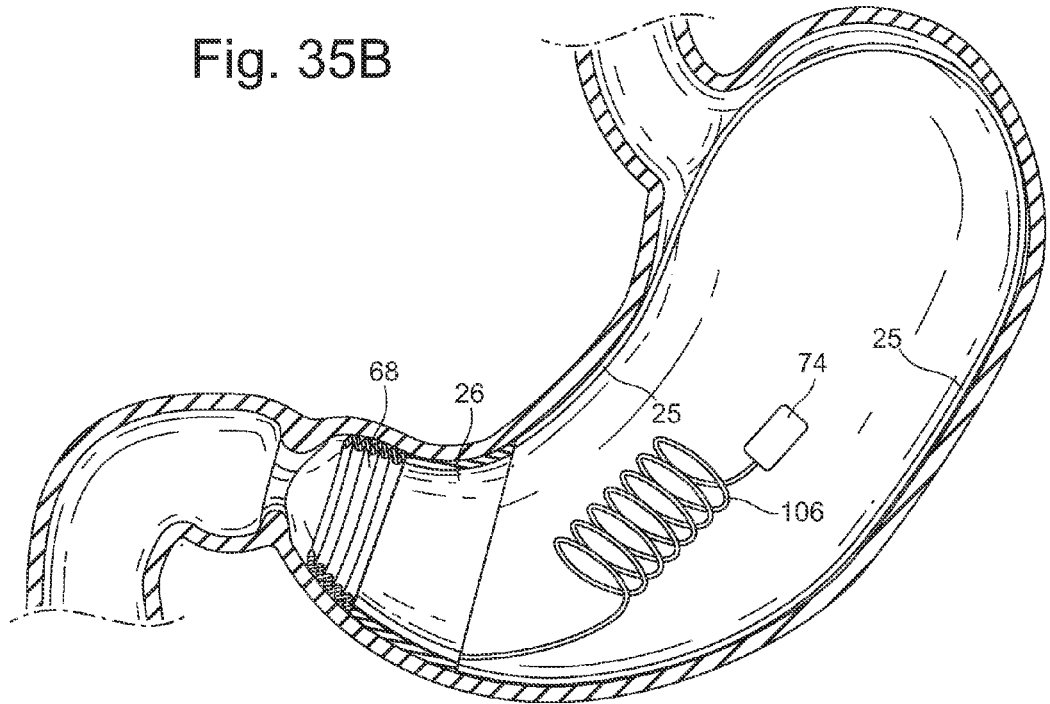

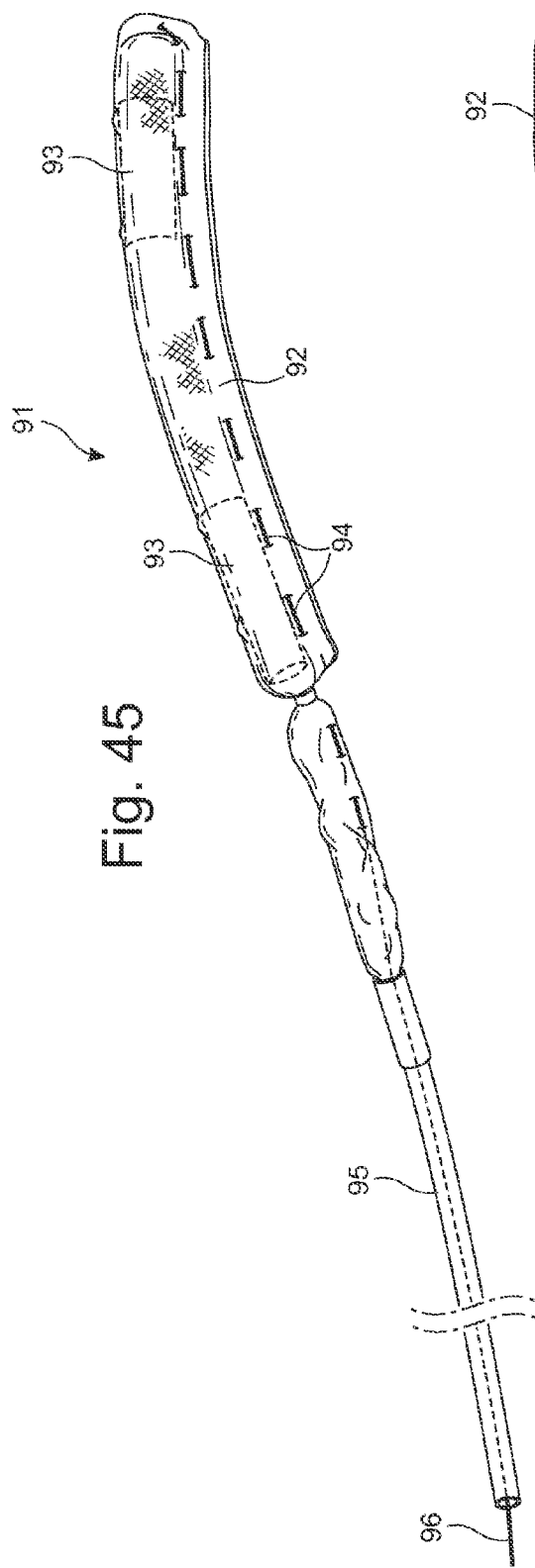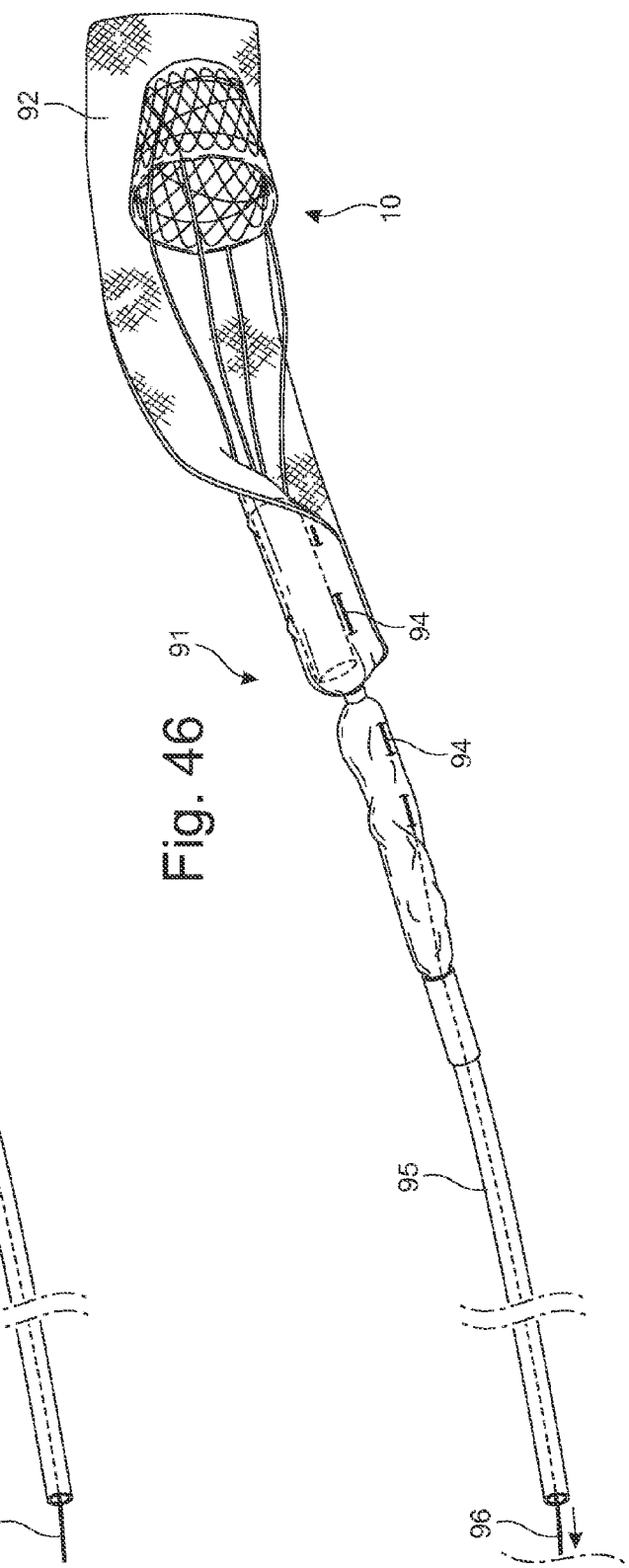

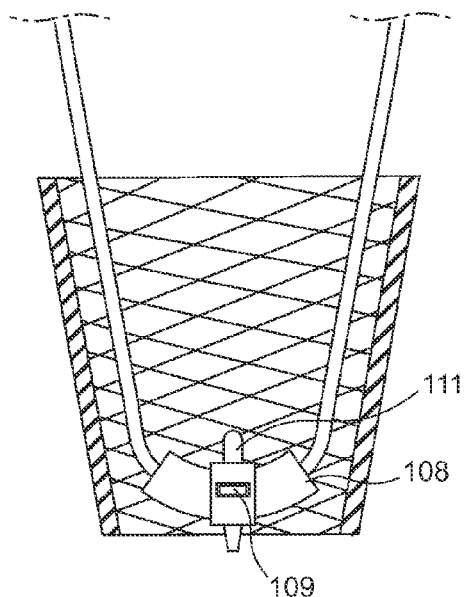
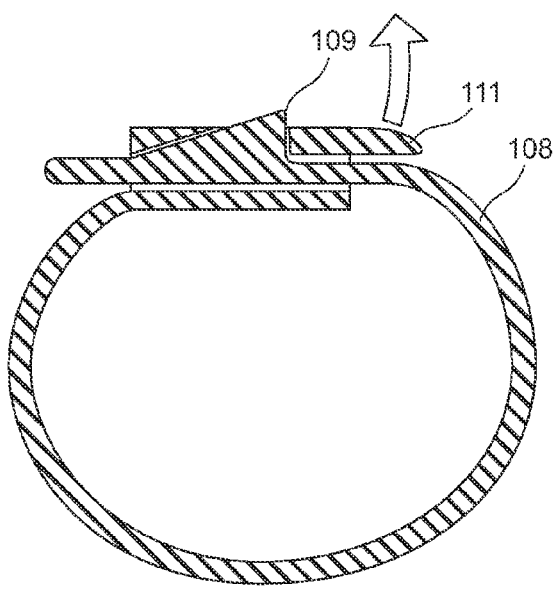
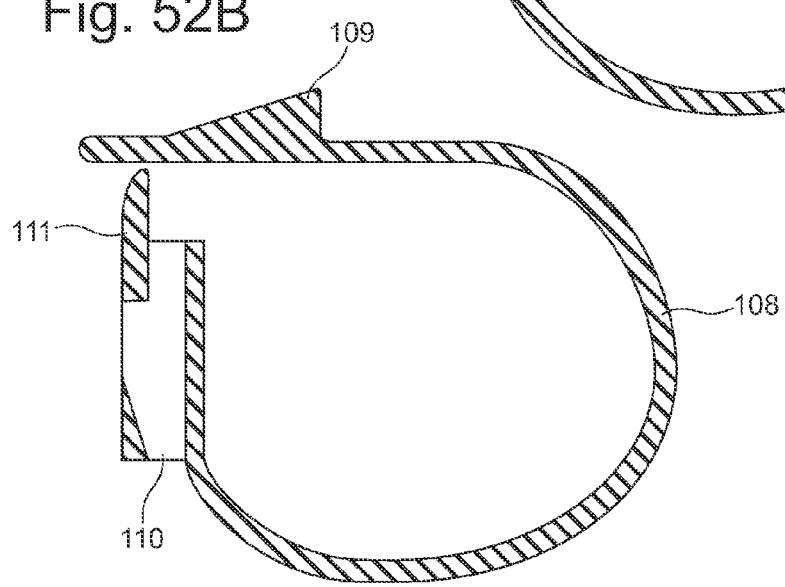

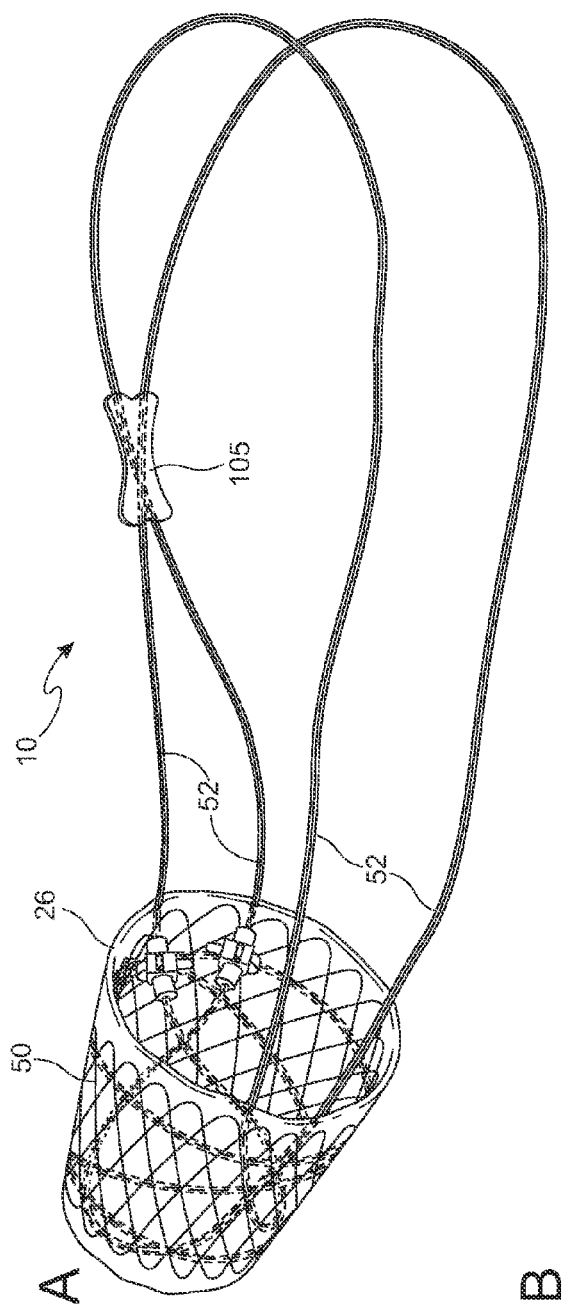
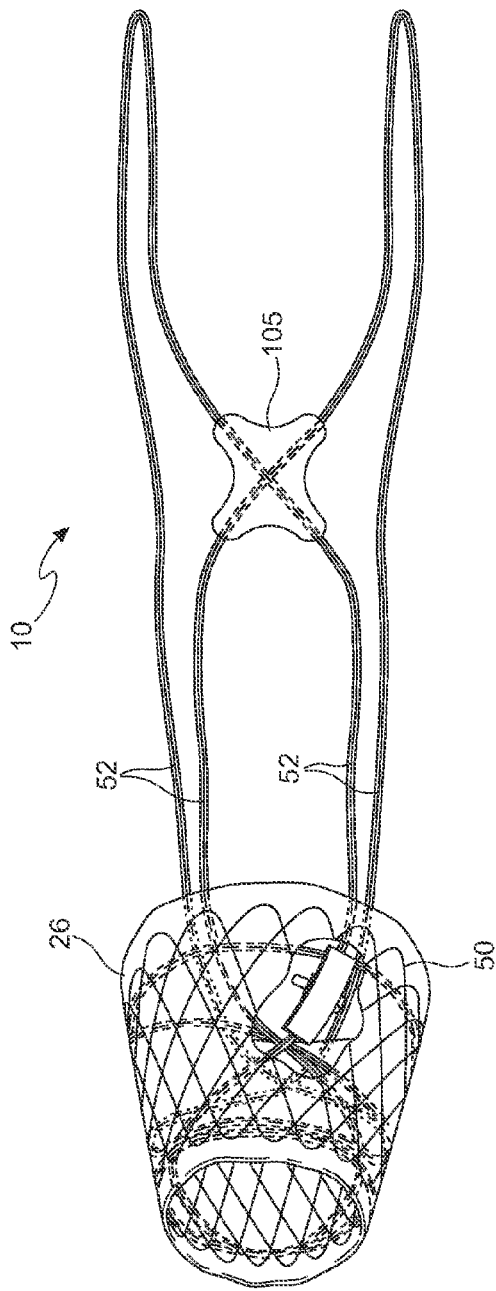
Fig. 53A
Fig. 53B

BARIATRIC DEVICE AND METHOD FOR WEIGHT LOSS

This application is a national phase application under 35 USC §371 of PCT Patent Application No. PCT/US2011/028565, filed Mar. 15, 2011, which claims the benefit of U.S. Provisional Application Nos. 61/314,131, filed Mar. 15, 2010, and 61/407,430, filed Oct. 27, 2010. Applicant hereby incorporates by reference PCT Application PCT/US2010-41774, filed Jul. 13, 2010, in its entirety, as if it were fully set forth herein, and any priority thereto. Applicant further incorporates by reference PCT Application PCT/US2010-053619, filed Oct. 21, 2010, in its entirety, as if it were fully set forth herein, and any priority thereto.

TECHNICAL FIELD

This invention relates to a bariatric device for weight loss, and ancillary items such as sizing, deployment, and removal apparatus.

BACKGROUND

Obesity has been steadily increasing worldwide and poses serious health risks, which if untreated, can become life threatening. There are various methods for reducing weight such as diet, exercise, and medications, but often the weight loss is not sustained. Significant advances have been made in the surgical treatment of obesity. Surgical procedures such as the gastric bypass and gastric banding have produced substantial and lasting weight loss for obese patients. These procedures and products have been shown to significantly reduce health risks over time, and are currently the gold standard for bariatric treatment.

Although surgical intervention has been shown to be successful at managing weight loss, both procedures are invasive and carry the risks of surgery. Gastric bypass is a highly invasive procedure which creates a small pouch by segmenting and/or removing a large portion of the stomach and rerouting the intestines permanently. Gastric bypass and its variations have known complications. Gastric banding is an invasive procedure which creates a small pouch in the upper stomach by wrapping a band around the stomach to segment it from the lower stomach. Although the procedure is reversible, it also carries known complications.

Less invasive or non-invasive devices that are removable and capable of significant weight loss are desirable.

SUMMARY

The bariatric device disclosed herein induces weight loss by engaging the lower stomach and may apply force or pressure to the lower stomach or to interrupt or alter peristalsis to replicate a fed state pattern. The bariatric device could also create resistance to slow the rate of gastric emptying due to a change in peristalsis or due to a feature in the device. The device is intended to engage the lower stomach which could include the pyloric region, the region just above the pyloric region, or both. Preferably, the device will contain a lumen or pathway for chyme to pass through the device and drain through the pylorus and into the duodenum, and not create an obstruction. In other embodiments, the device may contain a valve or feature to delay gastric emptying. Preferably, the device will be generally self seating due to the shape of the device and peristaltic motion of the stomach. Postprandially, the peristaltic waves in the stomach move in antegrade, from the proximal to distal, and these waves may encourage the device to sit lower in the stomach and engage the lower stomach region, but not contact the pylorus. The device could engage the lower stomach and apply linear or radial pressure to alter peristalsis or induce a satiety response. The lower stomach element is sized and constructed of materials of adequate resistance to prevent contact with or migration across the pylorus, or migration into the esophagus. This pressure could range from light pressure to a higher pressure. The pressure could be applied while the stomach is at rest or apply resistance to peristaltic waves. As peristalsis slows or reverses, the device could then toggle out of place into the body of the stomach. Alternatively, the device could be fixed to the stomach. Sutures or attachments could be used to fix the device in place and be of sufficient length to either fix the device closely for little movement, or the fixation could be longer to allow for greater movement but not complete dislodgement in the stomach. The device could also contain weights or a weighted element to encourage the device to seat in the lower stomach. The weights could guide the device lower in the stomach for proper seating and aid in maintaining its position. The device can be straightened, collapsed or compressed to allow for introduction down the esophagus. Once in the stomach, the device could then change into the desired shape inside the stomach and migrate into position in the lower stomach.

A preferred embodiment of the device is primarily comprised of a main lower stomach element. One of the purposes of the lower stomach element would be to apply at least intermittent linear or radial pressure or to contact the lower stomach to alter peristalsis, engage a stretch receptors and/or cause a neurohormonal response to cause a reduction in weight. This pressure would replicate the presence of food to stimulate the stomach neurohormonal response or could cause a change in the peristaltic process. This satiety response may cause gastric emptying to slow. Another purpose of the lower stomach element is also to prevent the device from contacting the pylorus or migrating into the duodenum or small intestine. This lower stomach element would be preferentially placed above and away from the pylorus and could be in constant or intermittent contact with the mid to lower stomach based on movement of the stomach. Depending on the size relative to the stomach, this element may apply radial force, linear force, contact force or pressure to the lower stomach which may also cause a satiety or neurohormonal response.

The lower stomach element could take several different shapes such as a ring, a disk, a cone, frusto-cone, a portion of a cone, portion of frusto-cone, a sphere, an oval, an ovoid, a tear drop, a pyramid, a square, a rectangle, a trapezoid, a wireform, a spiral, portions of any of the above or multiples of any shape or other suitable shapes. The lower stomach element could also be a long curved wire, a curved cylinder of varying diameters, a spiral of a single diameter, a spiral of varying diameter, a ribbon, an I-beam, a tube, a taper, a loop, a combination of these, or other suitable shapes. The lower stomach element could also be an inflatable balloon. This balloon could be spherical, or it could be a torus or a sphere with channels on the side to allow food to pass, or it could be a cone, a portion of a cone or other shape. The bariatric device may be in constant or intermittent contact with the mid to lower stomach based on the device moving in the stomach during peristalsis.

The lower stomach element may contain an additional element that is firm, rigid or of sufficient resistance to aid in preventing migration. This anti-migration element could consist of a ring that attaches to the distal end of device and is large enough in diameter or cross-section and firm enough to prevent the device from passing through to the pylorus. There may be a fringe benefit of this element in that it may activate another neurohormonal response to induce satiety, delayed gastric emptying or another mechanism of weight loss. The anti-migration element could also contain a restrictive element to delay gastric emptying.

In another embodiment, the bariatric device and may engage the mid to lower stomach and contain an element to maintain the general position of the device. This positional element may engage the upper stomach and/or the body of the stomach. One embodiment of the bariatric device disclosed herein is based on applying pressure to or being in contact with the lower stomach and may include a restrictive element. The device can be straightened or compressed to allow for introduction down the esophagus and then change into the desired shape inside the stomach. This device may not require any sutures or fixation and would orient inside the stomach based on the device's geometry or the device may compress due to peristalsis. In some cases, the device could be sutured or fixed to maintain its position. As described above, the device may be constructed of a single element.

In another embodiment, the device may be constructed of 2 main elements:

1) A lower stomach element that engages the lower stomach which includes the pyloric region, pyloric antrum, and/or the region adjacent and proximal to the pyloric region.

2) A positioning element that maintains the relative position of the lower stomach element in the lower stomach.

One of the purposes of the lower stomach element would be to apply at least intermittent linear, radial pressure or contact to the lower stomach to alter peristalsis, engage stretch receptors and/or cause a neurohormonal response to cause a reduction in weight. This pressure would replicate the presence of food to stimulate the stomach neurohormonal response or could cause a change in the peristaltic process. This satiety response may cause gastric emptying to slow. Another purpose of the lower stomach element is also to prevent the device from contacting the pylorus or migrating into the duodenum or small intestine. This lower stomach element would be preferentially placed above and away from the pylorus and could be in constant or intermittent contact with the mid to lower stomach based on movement of the stomach. Depending on the size relative to the stomach, this element may apply radial force, linear force, contact force or pressure to the lower stomach which may also cause a satiety or neurohormonal response.

The lower stomach element could take the form of many different shapes such as a ring, a disk, a cone, frusto-cone, a sphere, an oval, an ovoid, a tear drop, a pyramid, a square, a rectangle, a trapezoid, a wireform, a spiral, a protuberance, multiple protuberances, a portion of any of the above shapes or multiples of any shape or other suitable shapes. It could also be an inflatable balloon or contain an inflatable balloon. This balloon could be spherical, or it could be a torus or a sphere with channels on the side to allow food to pass, or it could be a cone, a portion of a cone or other shapes. The lower stomach element may be in constant or intermittent contact with the lower stomach based on the device moving in the stomach during peristalsis. For the purpose of the claims of this patent, the "lower stomach" includes the pyloric region and the area proximal and adjacent to the pyloric region.

Another function of the lower stomach element is to prevent the device from contacting the pylorus or migrating through the pyloric valve into the duodenum or small intestine. Preferentially, the lower stomach element would stay above and away from the pylorus and could be in constant or intermittent contact with the mid to lower stomach based on movement of the stomach. Depending on the size relative to the stomach, the lower stomach element may apply radial force, linear force, contact force or pressure to the lower stomach, which may also cause a satiety or neurohormonal response or affect the peristaltic process. Due to peristalsis of the stomach, the bariatric device may toggle back and forth in the stomach, which may cause intermittent contact with the upper stomach or fundus and lower stomach regions. The device may also have features to allow the device to flex or contract to accommodate for the motion to allow for constant contact with the upper and lower regions. The lower stomach element may activate stretch receptors or a neurohormonal response to induce satiety or another mechanism of weight loss by contacting or stretching certain portions of the stomach, to alter peristalsis, induce satiety, delay gastric emptying or another mechanism of weight loss. The lower stomach element could also contain a restriction element to reduce the speed of gastric emptying. As used in the claims, reducing the speed of gastric emptying does not include completely occluding or obstructing gastric emptying.

In some cases the device may be generally symmetrical and may contain two elements, a first and a second element, either of which can engage the mid to lower stomach. This general symmetry would allow that in the event that the device was to rotate in the stomach, it could reseat without concern of proper orientation. While one element engages the lower stomach, the other element may contact the upper stomach or fundus. The form and structure of the first and a second element may be the same or may vary to adapt appropriately for their purpose, and there may be structure that is not symmetrical.

Some of the purposes of the positioning element are to provide structure for the device to maintain its relative location, and in some cases to provide tension, pressure, or contact between the lower stomach and the upper stomach to aid in maintaining position. For purposes of the claims for this patent, the upper stomach may include the cardia, the fundus and the body of the stomach. The positioning element could take several different forms such as a long curved wire, a curved cylinder of varying diameters, a spiral of a single diameter, a spiral of varying diameter, a ribbon, an I-beam, a tube, a woven structure, a taper, a loop, a curved loop or other form or combination of any of the above. Similarly, the positioning element could comprise multiple members to improve its structural integrity and positioning within the stomach. The positioning element could be generally curved to match the greater curve, lesser curve, anterior or posterior walls of the stomach, or not follow the stomach contours by being straight, round, oblong, spherical or a combination of any of the above. The positioning element could also be an inflatable balloon or incorporate an inflatable balloon.

After eating or drinking, the stomach goes through peristalsis to grind up the consumed food, and to propel the contents through the pylorus into the duodenum. Peristalsis causes the stomach to constantly change shape in length and diameter. Due to this constant motion, it is anticipated that this embodiment will move within the stomach. The positioning element may slide back and forth along the greater curve, the lesser curve or along the side walls of the stomach. The positioning element may intermittently engage the upper stomach, but be of a large enough size to prevent passage into the esophagus. The positioning element may include elements that are compressible to allow them to pass from a larger portion of the stomach into a smaller portion of the stomach such as from the fundus to the body, while exerting pressure or intermittent pressure on the lower stomach element. Alternatively, the positioning element could have limited compressibility to maintain its position within the stomach.

The lower stomach and/or positioning elements could be self expanding or incorporate a portion that is self expanding. Self expansion would allow the element or a portion of the element to be compressible, but also allow it to expand back into its original shape to maintain its function and position within the stomach, as well as the function and position of the other element(s). Self expansion would allow the elements to compress for placement down the esophagus, and then expand to its original shape in the stomach. This will also allow the element to accommodate peristalsis once the device is in the stomach, but allow the device to be large enough to prevent it from migrating across the pylorus. This self expansion construction of the positioning element may impart an outwardly biasing force on the lower stomach element.

In any of the embodiments disclosed herein, the device may be straightened or collapsed for insertion down the esophagus, and then reformed to the desired shape in the stomach. At least a portion of the device could be made of shape memory alloys or super elastic alloys such as Nitinol (nickel titanium), low density polyethylene or polymers to allow for it to compress or flex and then rebound into shape in the stomach. The device could also be made of rigid materials in the form of linkages that allow for straightening and then locking in of difference shape inside the stomach. For placement of the device into the stomach, a flexible polymer tube, such as a large diameter overtube or orogastric tube could be placed down the esophagus to protect the esophagus and stomach. The device could then be straightened and placed into the tube for delivery into the stomach, and then would regain its proper shape in the stomach once it exits the tube. Another variation for placement would be a custom delivery catheter to compress the device during placement and then allow the device to deploy out of the catheter once in the stomach.

The bariatric device could be made of many different materials. Elements of the device could be made with materials with spring properties that have adequate strength to hold their shape after reforming, and/or impart an outwardly biasing force. Elements could also be made of materials that are not flexible or have limited flexibility. For a device that is made of inflexible or limited flexible materials, the device could contain design elements to accommodate peristalsis or the device could toggle within the stomach. The device could also be made of a combination of flexible, limited flexibility and inflexible materials. The materials would also need to be acid resistant to withstand the acidic environment of the stomach. Elements of the device could be made of Nitinol, shape memory plastics, shape memory gels, stainless steel, super alloys, titanium, silicone, elastomers, teflons, polyurethanes, polynorborenes, styrene butadiene co-polymers, cross-linked polyethylenes, cross-linked polycyclooctenes, polyethers, polyacrylates, polyamides, polysiloxanes, polyether amides, polyether esters, and urethane-butadiene co-polymers, other polymers, or combinations of the above, or other suitable materials. Where Nitinol is used, it is preferred to passivate the material to improve the acid resistance. For good distribution of stress to the stomach wall or to reduce contact friction, the device could be coated with another material or could be placed into a sleeve of acid resistant materials such as teflons, PTFE, ePTFE, FEP, silicone, elastomers or other polymers. This would allow for a small wire to be encased in a thicker sleeve of acid resistant materials to allow for a better distribution of force across a larger surface area.

The device could take many forms after it reshapes.

BRIEF DESCRIPTION OF DRAWINGS

FIG. 1 depicts a cross-sectional side view of a single element embodiment the bariatric device of the present invention located within a cross-section of a stomach.

FIG. 2A depicts a side view of a self expanding single element embodiment the bariatric device of the present invention located within a cross-section of a stomach.

FIG. 2B depicts a side view of a self expanding single element embodiment the bariatric device of the present invention.

FIG. 2C depicts a variation of a side view of a self expanding single element.

FIG. 3 depicts a cross-sectional side view of an embodiment of the bariatric device with fixation elements of the present invention located within a cross-section of a stomach.

FIG. 4 depicts a cross-sectional side view of an embodiment of the bariatric device of the present invention, located within a cross-section of a stomach.

FIG. 7 depicts a cross-sectional side view of an embodiment of the bariatric device of the present invention, located within a cross-section of a stomach.

FIG. 8A depicts a side view of an embodiment of the bariatric device of the present invention, located within a cross-section of a stomach.

FIG. 8B depicts a back view of the embodiment from FIG. 8A.

FIG. 8C depicts a variation of the back view of the embodiment from FIG. 8A.

FIG. 8D depicts a side view of an embodiment of the bariatric device of the present invention, located within a cross-section of a stomach.

FIG. 8E depicts a back view of the embodiment from FIG. 8D.

FIG. 8F depicts a variation of the back view of the embodiment from FIG. 8D.

FIG. 9A depicts a side view of an embodiment of the bariatric device of the present invention, located within a cross-section of a stomach.

FIG. 9B depicts a back view of a variation of embodiment from FIG. 9A.

FIG. 20A depicts an underside perspective view of an embodiment of the bariatric device of the present invention.

FIG. 20B depicts a front view of an embodiment of the bariatric device of the present invention.

FIG. 21A depicts an underside perspective view of an embodiment of the bariatric device of the present invention.

FIG. 21B depicts a front view of an embodiment of the bariatric device of the present invention.

FIG. 22A depicts an underside perspective view of an embodiment of the bariatric device of the present invention.

FIG. 22B depicts a front view of an embodiment of the bariatric device of the present invention.

FIG. 23A depicts an underside perspective view of an embodiment of the bariatric device of the present invention.

FIG. 23B depicts a front view of an embodiment of the bariatric device of the present invention.

FIG. 23C depicts an underside perspective view of an embodiment of FIG. 23A in a folded, compressed state.

FIG. 23D depicts a front view of an embodiment of the bariatric device of FIG. 23A in a folded, compressed state.

FIG. 27A depicts an underside perspective view of an embodiment of the bariatric device of the present invention.

FIG. 27B depicts a front view of an embodiment of the bariatric device of the present invention.

FIG. 27C depicts an underside perspective view of an embodiment of FIG. 27A in a folded, compressed state.

FIG. 27D depicts a front view of an embodiment of the bariatric device of FIG. 27A in a folded, compressed state.

FIG. 30A depicts a cross-sectional side view of an embodiment of the present invention, located within a cross-section of a stomach.

FIG. 30B depicts a back view of a lower stomach element from FIG. 30A.

FIG. 30C depicts a cross-sectional side view of a variation of the lower stomach element from FIG. 30A.

FIG. 30D depicts a back view of the lower stomach element from FIG. 30C.

FIG. 30E depicts a back view of a variation of the lower stomach element from FIG. 30D.

FIG. 30F depicts a cross-sectional side view of a variation of the lower stomach element from FIG. 30A.

FIG. 30G depicts a back view of the lower stomach element from FIG. 30F.

FIG. 35A depicts a cross-sectional side view of an embodiment of the bariatric device of the present invention, located within a cross-section of a stomach.

FIG. 35B depicts a cross-sectional side view of an embodiment of the bariatric device of the present invention, located within a cross-section of a stomach

FIG. 45 depicts a side view of a delivery sheath containing a medical device.

FIG. 46 depicts a side view of the delivery sheath shown in FIG. 45, partially opened to show an expanded medical device.

FIG. 51 depicts a side view of a modular clip mechanism of an embodiment of the present invention.

FIG. 52A depicts a side cross-section view of a modular clip in a closed position of the embodiment of FIG. 51.

FIG. 52B depicts a side cross-section view of a modular clip in an open position of the embodiment of FIG. 51.

FIG. 53A depicts an underside perspective view of an embodiment of the bariatric device of the present invention with modular clips.

FIG. 53B depicts a front view of an embodiment of the bariatric device of the present invention with modular clips.

DETAILED DESCRIPTION OF THE INVENTION

Figure 5B:
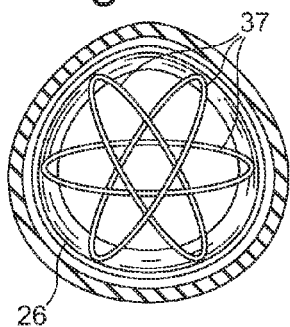
FIG. 5B depicts a back view of the embodiment from FIG. 5A.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The most basic embodiment of the bariatric device 10 is a single element design that may have a single cone with a lumen that can be collapsed and placed down the esophagus into the lower stomach. For the purposes of the claims, a lumen is defined as an open passageway through the device with a proximal opening and a distal opening, which may be tapered, cylindrical or other shapes. This device could be thin walled or thicker walled. Due to the conical shape, the bariatric device 10 would be self seating in lower stomach. The device would need to be of sufficient radial resistance to prevent collapse and migration through the pylorus. See FIG. 1. The device would be free to push out of the way to allow it to move into the upper stomach as needed, and to engage stretch receptors or to alter peristalsis. This device could be made from silicone, an elastomer, Nitinol, another acid resistant polymer or a combination of any of the above.

Another variation of the bariatric device 10 incorporates a self-expanding feature. FIGS. 2A, 2B and 2C show an alternative of the design with a self expanding feature which incorporates a Nitinol wire mesh or wireform array 50. The device 10 could be self expanding or have a portion that is self expanding to allow the device to flex with peristalsis, but maintain tension to spring open to maintain its function and position within the stomach while reducing the potential for stomach irritation. The device could also be constructed of a combination of materials that allow the device to toggle out of position and reseat. The self expanding portion could be made of Nitinol, silicone, polyurethane, PTFE, other flouropolymers, other suitable materials or combinations of any of the above. FIG. 2A shows a Nitinol wire mesh pattern 50 applied to a conical shape to create a conical shell with lumen. FIG. 2A also shows how the distal end of the device could have a rounded shaped or a chamfer as in FIG. 2B. The Nitinol wire mesh 50 could be arranged in many different patterns to allow for the appropriate amount of self expansion while allowing the element to compress during peristalsis. The array pattern could include circular arrays, angular arrays, or other suitable configurations. The array could be designed to encourage more expansion in one area than in another to further improve the function of the device. In this embodiment, the Nitinol mesh 50 may be exposed for direct contact with the stomach as a contact member 54 or it could be covered or sealed in another material, such as silicone, PTFE, polyurethane or other suitable materials to seal the outside or to add additional structure. The wire array could be arranged and formed to add a wavy pattern to increase the profile of the wire above the element's nominal surface, which in this case is shown as a cone with the wire protruding above the cone's surface in FIG. 2B. This arrangement would allow the wire to act as a macro texture to grip the stomach surface to reduce sliding or it could provide a macro texture for tissue ingrowths. The Nitinol may be treated with a surface finish, passivation or coating to improve its acid resistance within the stomach. FIG. 2C shows the lower stomach element encased in silicone or other material to create a smooth surface for contact.

To constrain the location and position of the device, the device could be fixed in place with one or more fixation elements 36. The fixation element could be standard sutures, a T-bar type connection, tacks or fixation elements that change in profile from narrow to wide to facilitate an endoscopic procedure. The fixation would constrain the location of the device to induce a continuous or more present satiety signal. See FIG. 3. These fixation elements 36 could be placed endoscopically from inside the stomach and pierce through the stomach will with a self anchoring design such as a t-bar or other device. This would allow the device 10 to be placed with an endoscopic procedure. The device 10 could also have a texture, mesh, surface pattern, protuberances, protruding elements or surface finish on the outer surface to allow for gripping mucosa of the stomach and holding its position over a time period.

The device 10 could also contain an additional anti-migration element that is firmer, more rigid or of sufficient resistance to prevent migration of the device through the pylorus. This anti-migration element 49 could be a firm or rigid ring that attaches to the end of the device or it could be another shape to better suit the form of the device 10. See FIG. 4. This anti-migration element 49 would need to have a sufficient firmness, resistance and/or width to prevent the device from passing across the pylorus. The device 10 could be optimized to provide adequate resistance against the stomach to accommodate peristalsis, but the firmness of the anti-migration element 49 prevents the possibility of migration. This anti-migration element could also be a reverse cone or other shapes to aid in preventing the device from passing. The anti-migration element 49 could be made of linkages that articulate and straighten for placement and then lock into shape after placement. Similarly, the anti-migration element could be a cut ring that is allowed to overlap and flex for placement but then lock into a ring shape after placement. The anti-migration element 49 could located anywhere on the device.

Figure 5A:
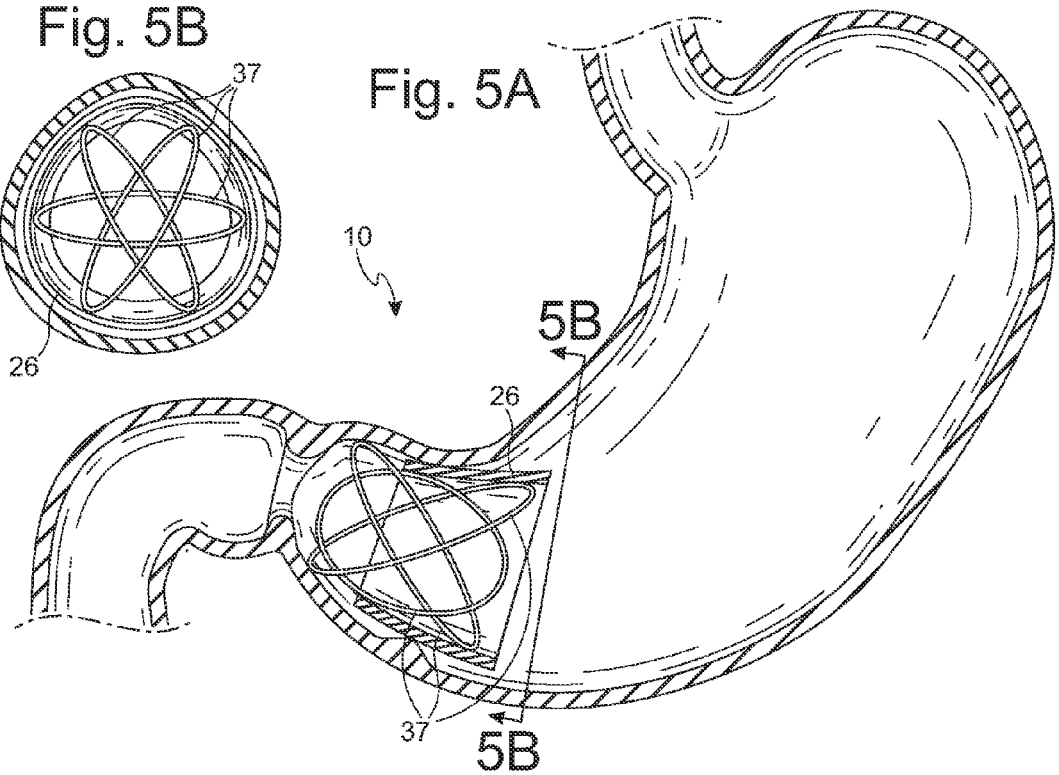
FIG. 5A depicts a side view of an embodiment of the bariatric device of the present invention, located within a cross-section of a stomach.

Another embodiment of the single element design could incorporate formed wires or loops 37 that reside inside the main lower stomach element 26. See FIG. 5A-5B. These formed wires or loops 37 could be rings or ovals or other shapes that are attached to the lower stomach element 26, but extend beyond the distal or proximal end to create a larger profile to prevent migration as an anti-migration element 49, and could apply additional radial resistance for generating satiety signals. These formed wires or loops 37 could be curved Nitinol wire or other material of a variety of diameters to increase their resistance to collapsing inside the stomach during peristalsis. These loops 37 may bend, but then reshape to accommodate peristalsis. These loops may also create a pattern to provide some resistance to gastric emptying. The loops could be made from wire, tubing or other materials.

Figure 6:
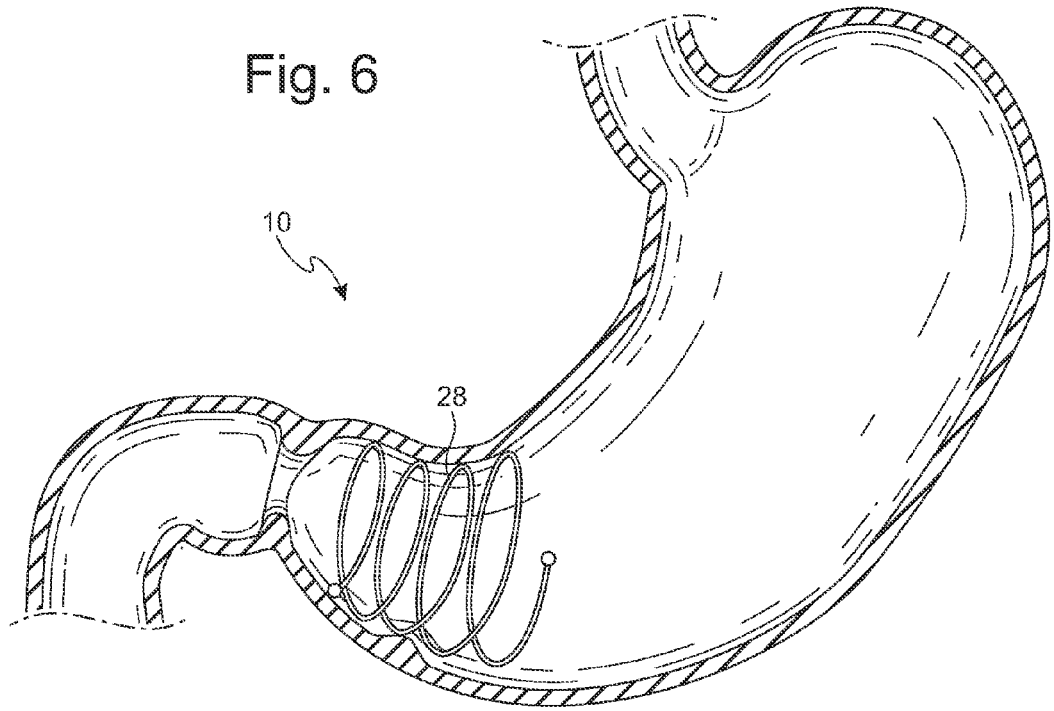
FIG. 6 depicts a side view of an embodiment of the bariatric device of the present invention, located within a cross-section of a stomach.

The device 10 could also take the form of a spiral 28. See FIG. 6. In one such embodiment, a piece of Nitinol wire is shape set in a tapered spiral that can be pulled under tension into a generally narrow, straight form. When tension to stretch the device is released, it may coil into a spiral as in FIG. 6. The device could also take the shape of multiple rings, a combination of both or other. The device 10 could be sutured or fixed into place, or it could contact the mid to lower stomach intermittently for a temporary effect.

In another variation, the device 10 could have multiple connected rings 31. These rings could be continuous or an open ring in a locked position prior to placement down the esophagus. The open rings could also be open during placement and then locked once inside the stomach. See FIG. 7. These rings 31 could be collapsed or compressed enough to fit within a placement tube for placement down the esophagus. The rings could have a round cross-section, or it could be flat, oval, wavy, convoluted or knobby to add pressure points to stimulate the lower stomach during peristalsis while reducing the potential for overstressing a certain area. These rings could be connected by a variety of means such as coating of silicone, wireform, links, an elastomer, a polymer, PTFE, ePTFE, other or a combination of any of the above. The device need not be fixed in place, but could be sutured into place if needed. This device could have separate ring with openings in between the rings to allow food and fluid to pass in between or the rings could have a covering or be encased to close the open holes. In another variation where the openings between the rings are open, the distal end of the device could be covered with solid surface so there is no lumen and food must passes through the openings between the rings to slow gastric emptying.

In another variation, a single element embodiment of the device 10 could be constructed by multiple loops 37 to create a wireform or structure with a shape such as an ovoid, sphere, taper or other. The form could also be created by a continuous piece of material that is woven or molded into different shapes to create the lower stomach element 26. See FIGS. 8A-8C. The structure could be collapsed or compressed under force for placement down the esophagus, but then reform into shape once in the stomach. This would create a structure that could engage the distal stomach, but be of sufficient diameter or profile to prevent migration. This wireform or structure would open enough to allow chyme to pass through to the pylorus and intestines, or could contain a restrictive feature to delay gastric emptying. When the loops or structure is configured, it will comprise multiple openings. During peristalsis, the device may be under compression. This compression could cause the openings to narrow or reduce in size and create a restriction or convoluted path to delay gastric emptying.

In another variation, the restriction could be a molded feature or rib feature such as is shown in a side view in FIG. 8D. In the back side view, FIG. 8E shows where a star pattern or other pattern could be formed in the device to create an opening when the stomach is at rest, but compress to create a greater restriction during peristalsis as shown in FIG. 8F. This restriction could be molded into a variety of patterns with a variety of cross-sectional shapes varying from complete closure to mild restriction. Although the figure shows eight ribs each with a trapezoid shape, the ribs could be a different shape such as rectangular and there could be one or more. The ribs also act as a mechanical block to prevent the device from over collapsing to prevent it from contacting or passing through the pylorus This restriction feature could extend the full length of the device as shown in FIG. 8D or it could only extend a portion of the length of the device. The bariatric device could be made from silicone, Nitinol, another suitable elastomer or material, or any combination thereof.

Figure 9C:
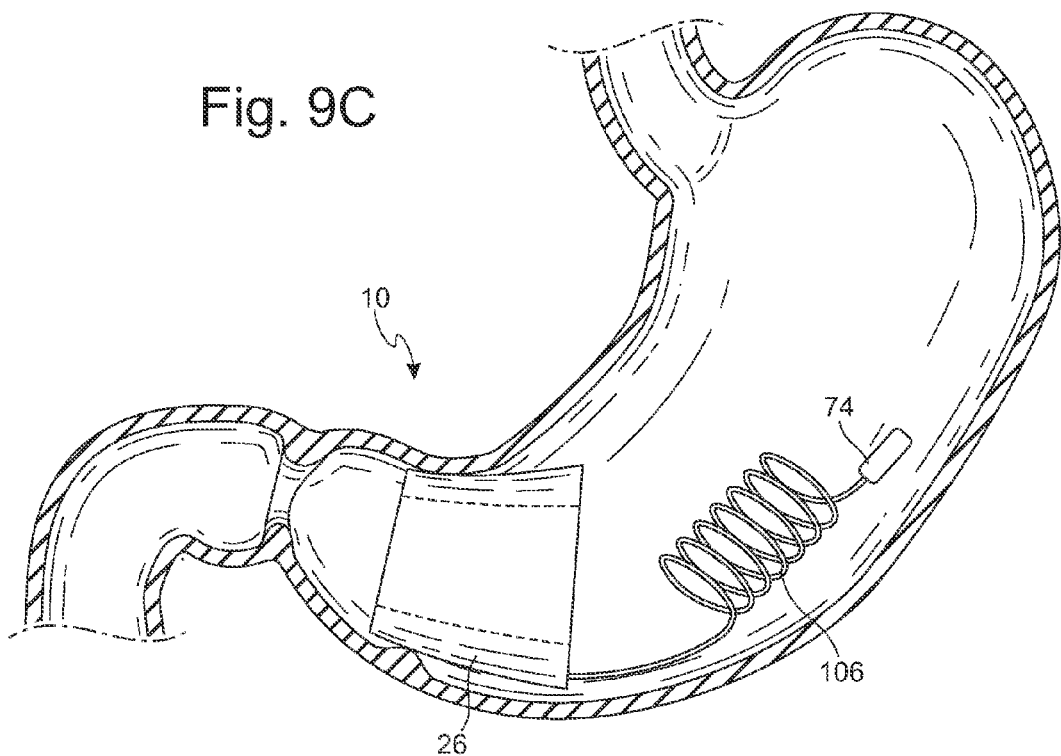
FIG. 9C depicts a side view of a variation of the bariatric device of FIG. 9A located within a cross-section of a stomach.

Another variation of this device would be to have an inflatable body 77 in a portion of the device, or along the whole device. See FIGS. 9A and 9B. This figure shows a thin walled inflatable balloon in a conical shape with a lumen. There could be several ways to inflate the device through an inflation element 74 including an injection port with a self-sealing septum that could be punctured by a needle to inject saline. The port could be attached directly to the device or connected by tubing as shown in FIG. 9A. Similarly, the device could have an inflation element 74 in the form of a self sealing septum that covers a surface of the inflatable body that would allow a needle to puncture this surface to inject saline directly into the inflatable body 77 using a gastroscopic instrument. FIG. 9B depicts a variation where the full back surface of the device is a self sealing surface that could be punctured for saline injection. The self sealing surface could be placed on any accessible surface such as the inner diameter of the lumen or other location. An inflatable body 77 would allow the bariatric device 10 to have radial expansion to vary the pressure placed against the stomach or to vary the inner diameter to create a restriction along the inside diameter. FIG. 9B shows a dashed to represent how the inside diameter could be reduced by an inflation element. Conversely, the outside diameter could be increase by a similar inflation element to increase the outer diameter. FIG. 9C, shows a variation of the inflation element where the valve 74 is attached to the lower stomach element by a retractable inflation tube 106. The retractable inflation tube 106 may be constructed of a coiled tube, which may be may be contained in a housing or free floating. Alternatively, the retractable inflation tube 106 may be attached to a separate leash or tether. The valve 74 can be grasped inside the stomach using a standard grasper or snare, and then pulled up the esophagus for access outside the body while maintaining the device inside the stomach. The inflation element 74 may be a slit valve that can be accessed by a blunt needle or small diameter instrument to push through the valve to allow fluid to be added or removed. After the appropriate volume of fluid has been added, the retractable inflation tube 106 can then be placed back into the stomach. Preferably, the retractable inflation tube 106 would be designed so that it would not contact or pass through the pylorus The inflatable body 77 could be made of all silicone or it could have a self expanding Nitinol mesh pattern along the outer or inner surface to provide additional structure as needed, or a combination of both or other.

Figure 10:
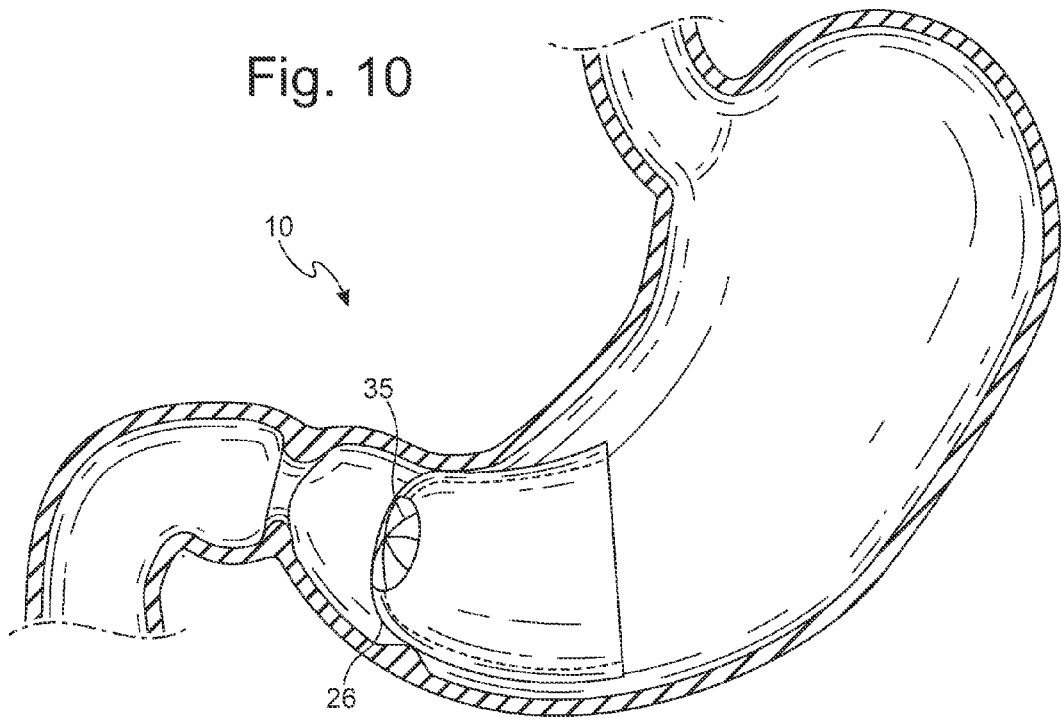
FIG. 10 depicts a side view of an embodiment of the bariatric device of the present invention, located within a cross-section of a stomach.

Another variation of the single element embodiment of the device 10 comprises a distal, proximal or middle surface that is closed, but with a restriction element in the form of a valve 35 that opens under pressure during peristalsis to open to allow for drainage of food through the pylorus into the duodenum. Another feature of this device would be increase the pressure inside the stomach as the stomach is trying to empty itself. The lower stomach would contract to attempt to empty the stomach to pass food through the valve, and this increase pressure would be applied to the upper stomach. This increased pressure would engage stretch receptors throughout the stomach including those located in the upper stomach or cardia to induce a neurohormonal response throughout the stomach and not just in a localized area due to direct contact of the device 10. This process would apply towards any restriction element. FIG. 10 shows an example of where the distal surface includes a valve to slow gastric emptying. This distal surface could be hemispherical, radiused, flat, chamfered, conical or other suitable shapes. The valve 35 could be a thin walled element and could be constructed from a silicone, a polymer, an elastomer, Nitinol, wire, other suitable material or a combination of any of the above. The valve 35 would allow for food to exit the stomach at a reduced rate, but would not obstruct flow from the stomach. In this case, the device could apply pressure to the lower stomach, but could also reduce the rate of gastric emptying. The valve could be located at the proximal side of the device 10 or in between the distal or proximal portions. Although the FIG. 10 shows an option location where the bariatric device 10 could sit in the stomach, the device 10 could be sized and shaped to sit higher in the stomach such as higher in the antrum or above the antrum or in both.

Figure 11:
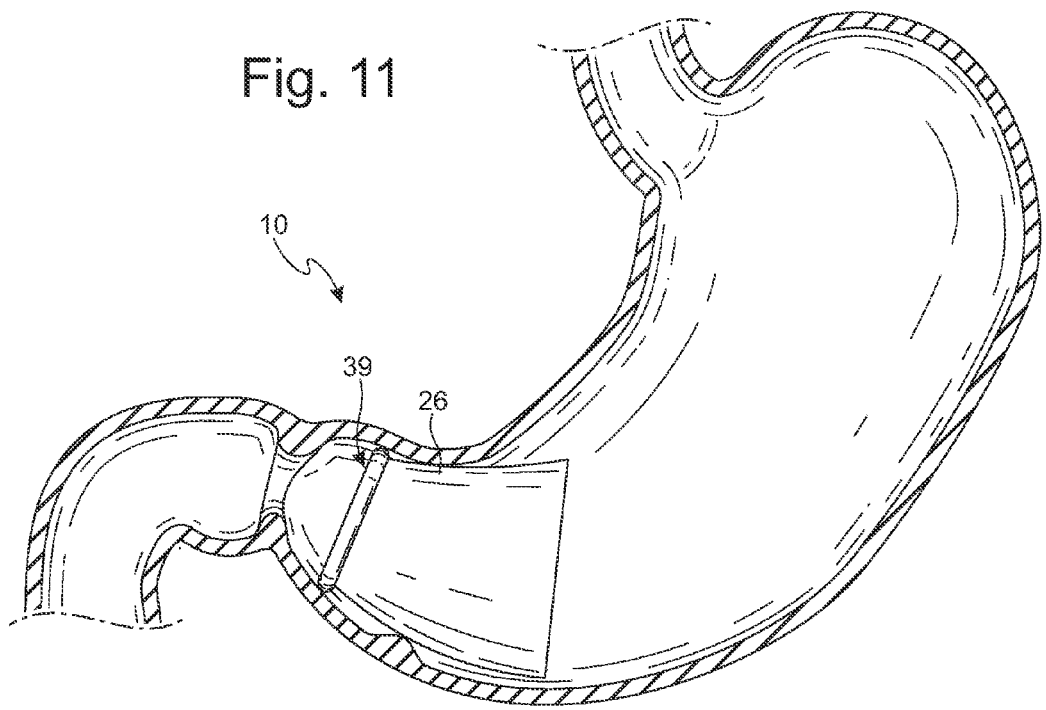
FIG. 11 depicts a side view of an embodiment of the bariatric device of the present invention, located within a cross-section of a stomach.

Another variation of the single element embodiment of the device 10 adds a weighted element 39 to the distal portion of the device 10 to guide the device into position in the lower stomach, but without migrating past the pylorus. See FIG. 11. The weight 39 could be a circular ring, an arrowhead, a cone, a sphere, or multiple weight elements or other shape to best accommodate the lower stomach. The weight 35 may be attached inside the lower stomach element 26 or could be attached to the end of the lower stomach element 26. The weight 35 may be coated with silicone, a polymer, or other acid resistant materials to protect the weight 35 in the stomach environment as needed.

Another variation of the device 10 would be a two element design with a positional element 25 added to the lower stomach element 26 to maintain the relative position of the device within the lower stomach. See FIG. 12. This positional feature could be added to any of the previously described lower stomach elements 26. This positional element 25 could be made from wire, flat ribbon, tubing, a molded feature or other form that general conformed to the shape of the stomach or a portion of the stomach to maintain the general location of the bariatric device 10. The positional element 25 shape could generally follow the greater curve 17, lesser curve 16, anterior wall or posterior sidewalls 20 of the stomach, be straight or any combination of the above. During peristalsis, this positional element 25 could compress or flex as needed to accommodate peristalsis, but provide resistance to maintain the general position of the device in the lower stomach. The positional element 25 could also be made up of multiple members to improve the structural integrity of the device.

Figure 12:
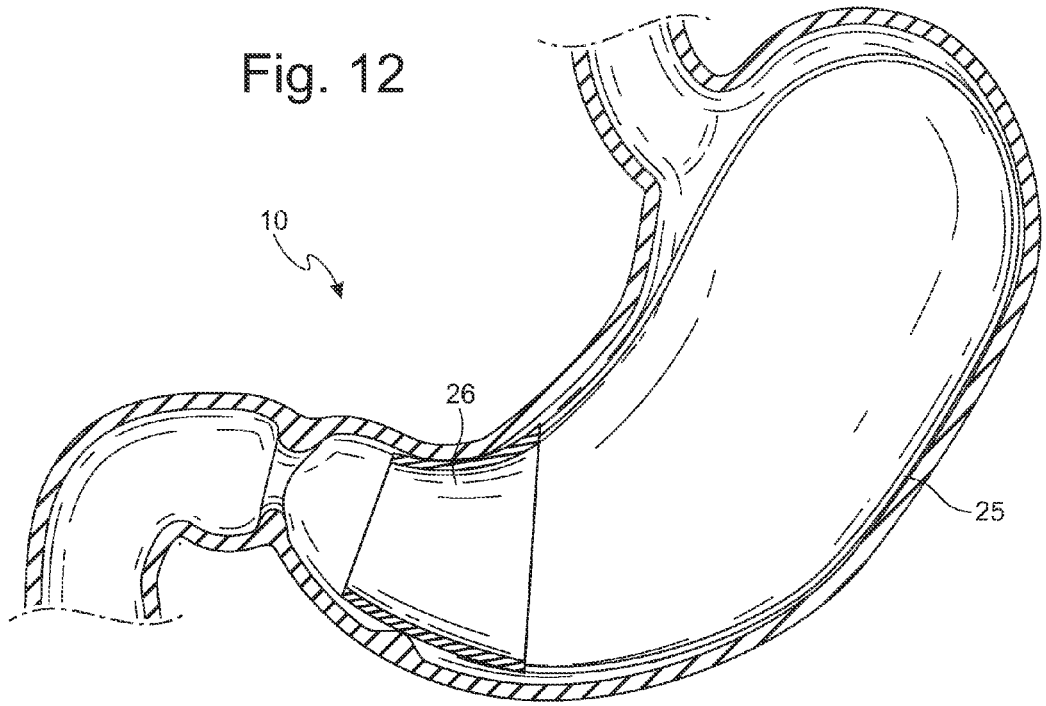
FIG. 12 depicts a cross-sectional side view of a 2 element embodiment of the present invention of a bariatric device, located within a cross-section of al stomach
Figure 13A:
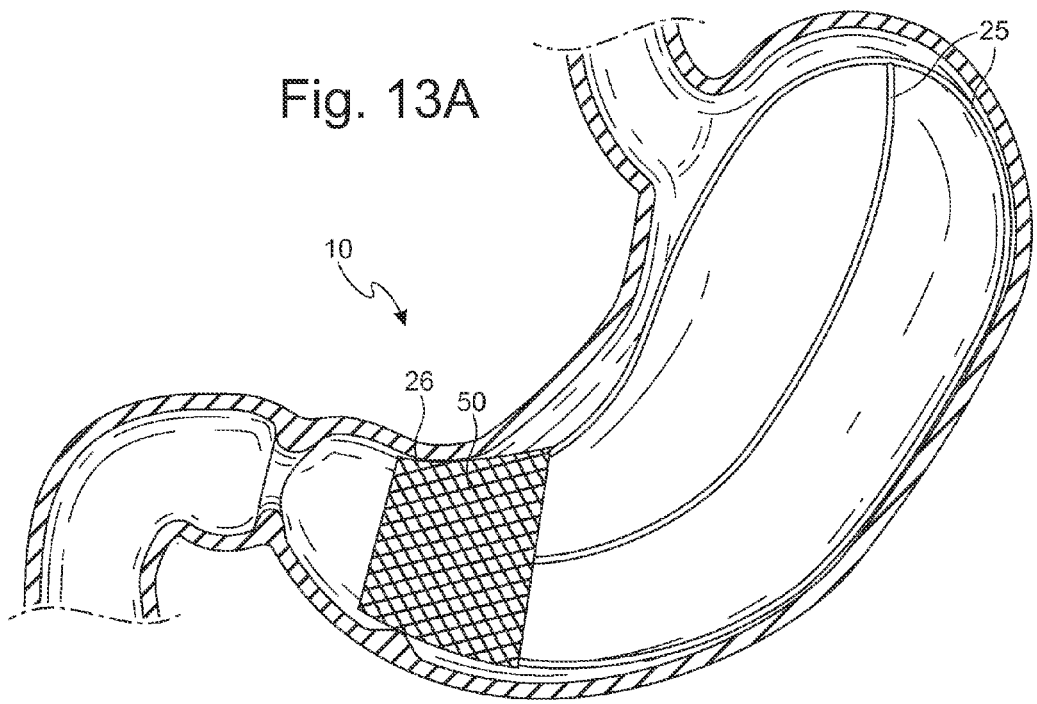
FIG. 13A depicts a side view of an embodiment of the bariatric device of the present invention, located within a cross-section of a stomach.

FIG. 12 shows a positional element 25 with a single member in a curved shape while FIG. 13A shows a positional element 25 with two curved members positioned at 90 degrees to one another. Alternatively, there could be 3 or more members formed in curved shapes to form the positional element 25. The positional elements 25 could also be full loops 51 in a curved shape or a combination of loops and curved or other shapes. These positional elements 25 could be made of Nitinol, metal, silicone, EPTFE, PTFE, elastomers, polymers or other suitable materials. These positional elements 25 preferably are flexible enough to collapse for placement down the esophagus and then spring back into shape once in the stomach, but could be made from inflexible materials that form into their final shape by linkages or other means. The positional element members could be other shapes such as a spiral, spring or other shape to accommodate peristalsis but maintain general position of the device. The positional element could also contain curves or bends that form living hinges to allow the device to accommodate peristalsis, but maintain the general position of the device. These positional element members could also be flexible to allow the positional element 25 to conform to the stomach during peristalsis.

Figure 13B:
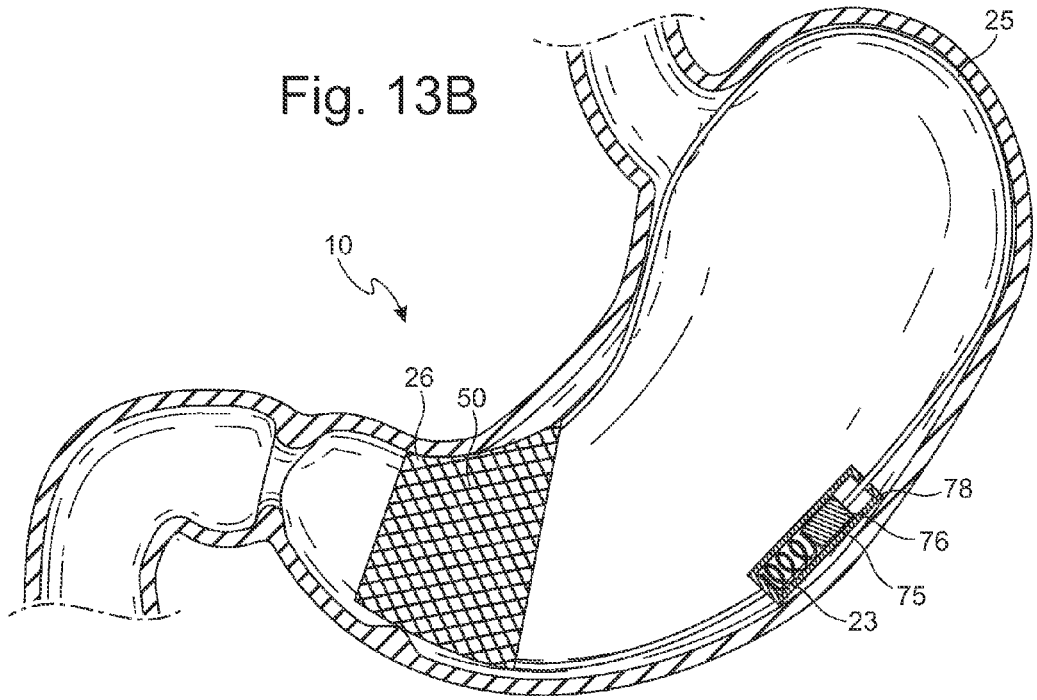
FIG. 13B depicts a cross-sectional side view of an embodiment of the bariatric device of the present invention with an expansion joint, located within a cross-section of a stomach.

The positional element 25 could be made of multiple members that would allow them to translate, articulate or rotate to accommodate for peristalsis. FIG. 13B depicts an embodiment where the positional element 25 has an expansion joint 75 that can translate to accommodate for peristalsis. The positional element 25 contains a proximal member connected to a piston or pin 76 that can slide inside of a cylinder 78 connected to the distal positional member. The cylinder contains a spring 23 to maintain outward pressure on the positional element assembly. As peristalsis occurs, the assembly may compress the spring 23 to reduce the overall length or profile of the positional element 25. As peristalsis relaxes, the spring 23 would provide enough counterforce to return the assembly to its uncompressed state. Such construction would provide an assembly that is self adjusting in length to accommodate for peristalsis. In this case the positional element members may be made of materials that are rigid or firm, but could also be made of materials with flexibility. Although this figure only shows one expansion joint 75, the device could contain more than one. Similarly, this device could also be constructed with the positional element constructed of 2 members, where one member is constructed of a tube and the other member is constructed of a rod, and they articulate relative to one another. This assembly could also contain a spring to maintain a specific spring load.

Figure 14:
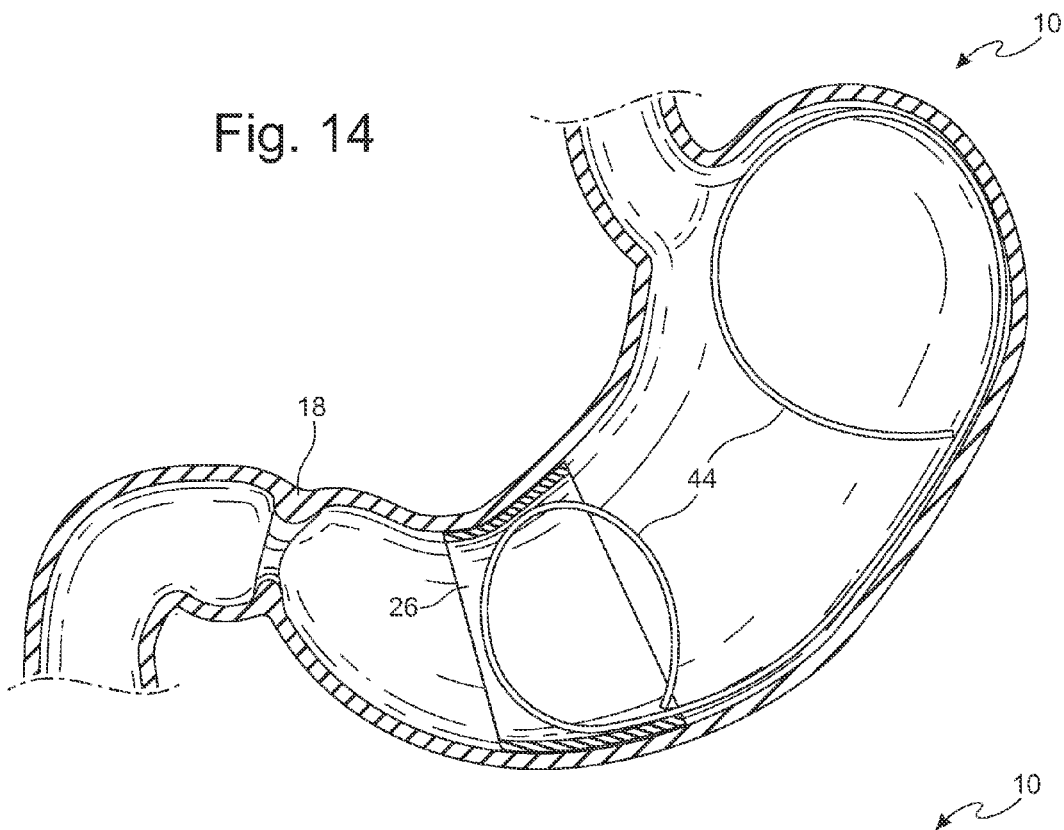
FIG. 14 depicts a cross-sectional side view of an embodiment of the bariatric device of the present invention, located within a cross-section of a stomach.
Figure 15:
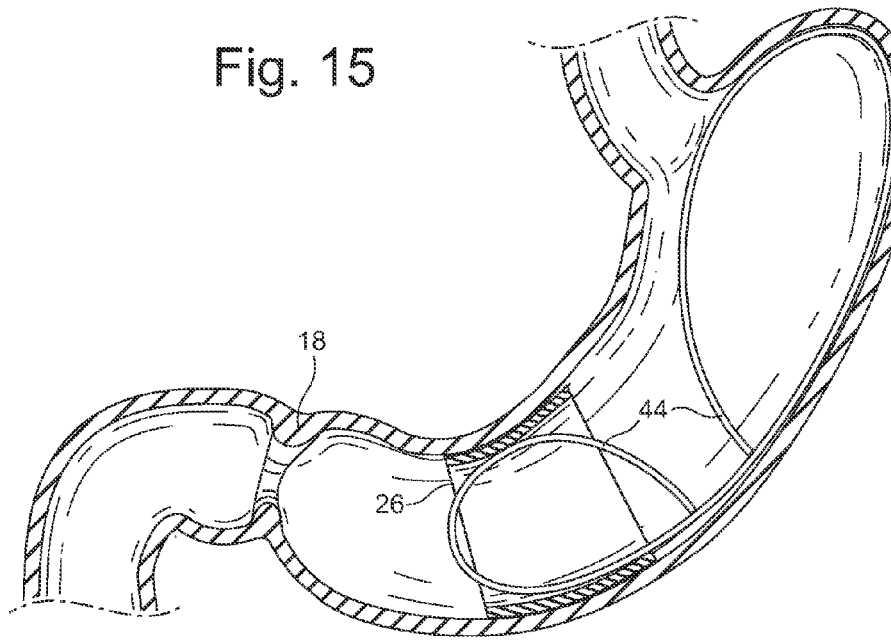
FIG. 15 depicts a cross-sectional side view of the embodiment of FIG. 14, located within a cross-section of a stomach that is undergoing contraction due to peristalsis.
Figure 16:
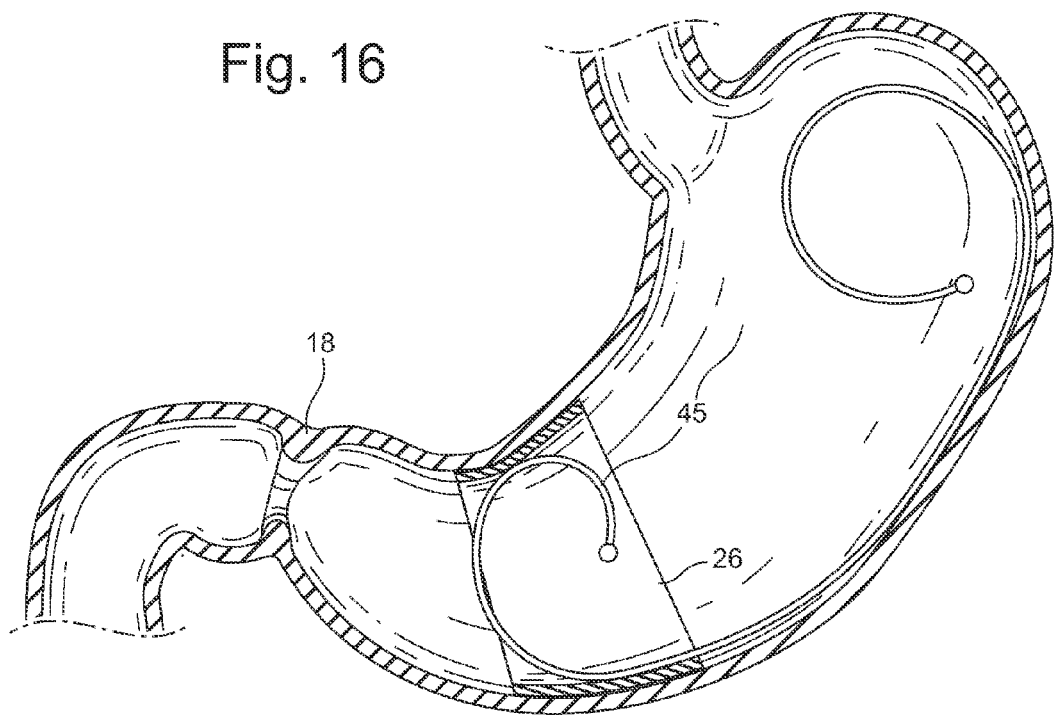
FIG. 16 depicts a cross-sectional side view of an embodiment of the bariatric device of the present invention, located within a cross-section of a stomach.
Figure 17:
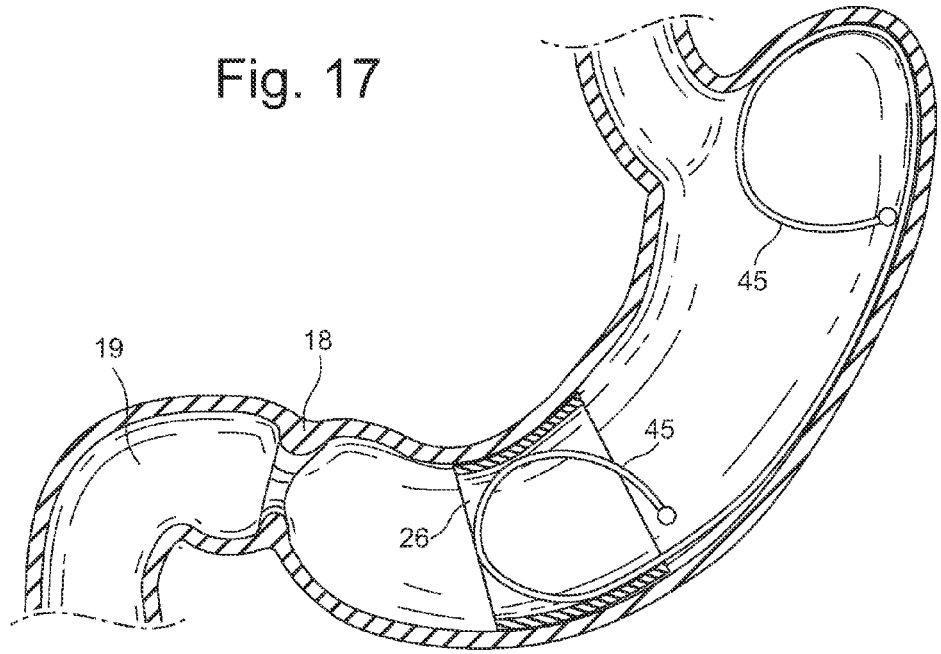
FIG. 17 depicts a cross-sectional side view of the embodiment of FIG. 16, located within a cross-section of a stomach that is undergoing contraction due to peristalsis.

Another variation of two element embodiment of the bariatric device 10 may have a single piece of shape set Nitinol wire 44 as the positional element 25, which can be pulled under tension into a generally narrow and straight form, to allow for insertion of the device 10 through the esophagus. This wire 44 may be connected with the lower stomach element 26. See FIG. 14. In such an embodiment, the positional element is connected with the lower stomach element 26, shown in FIG. 14 as a steep frusto-cone. FIGS. 14 and 15 depict an alternate embodiment of the design to adapt to stomach profile changes. FIG. 14 depicts the lower stomach element 26 engaging the lower stomach region while the positioning element 25 comprises two closed loops 44 of highly resilient material at each end, which can compress and flex to accommodate peristalsis within the stomach. FIG. 14 shows that the positioning element 25 has a closed loop at the proximal and distal ends where the distal loop connects to the lower stomach element 26. FIG. 15 shows these loops compressing during peristalsis to allow the device to maintain its relative position in the stomach and preventing it from migrating past the pylorus. Depending on the size of the stomach, the shape set wire 44 may impart an outwardly biasing force to the proximal and distal elements of the bariatric device 10, which may vary during peristalsis or could toggle to intermittently contact the upper and lower stomach without applying an outwardly biasing force. FIGS. 16 and 17 depict another variation of this embodiment where the loops 45 are open and allowed to flex until closed. Another embodiment has closed loops, but includes a mechanical stop inside the loop next to where the loop is closed to set a maximum amount that the device can flex.

Figure 18A:
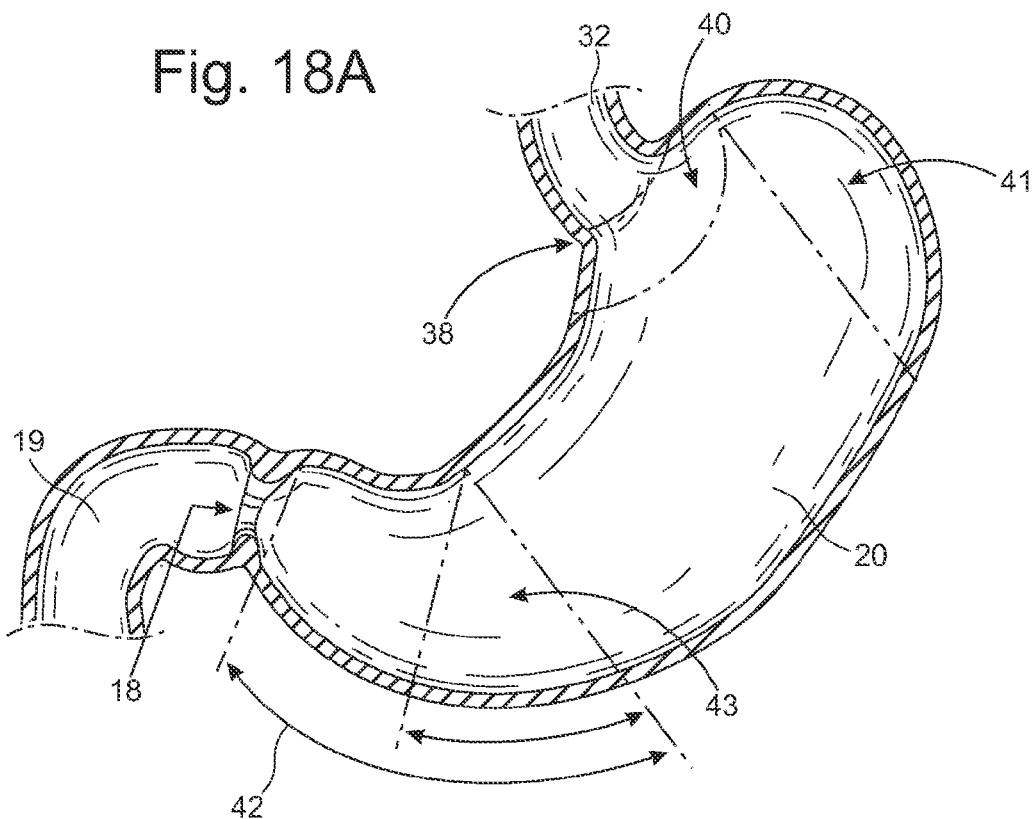
FIG. 18A depicts a side view of a cross-section of a stomach, identifying anatomical features.
Figure 18B:
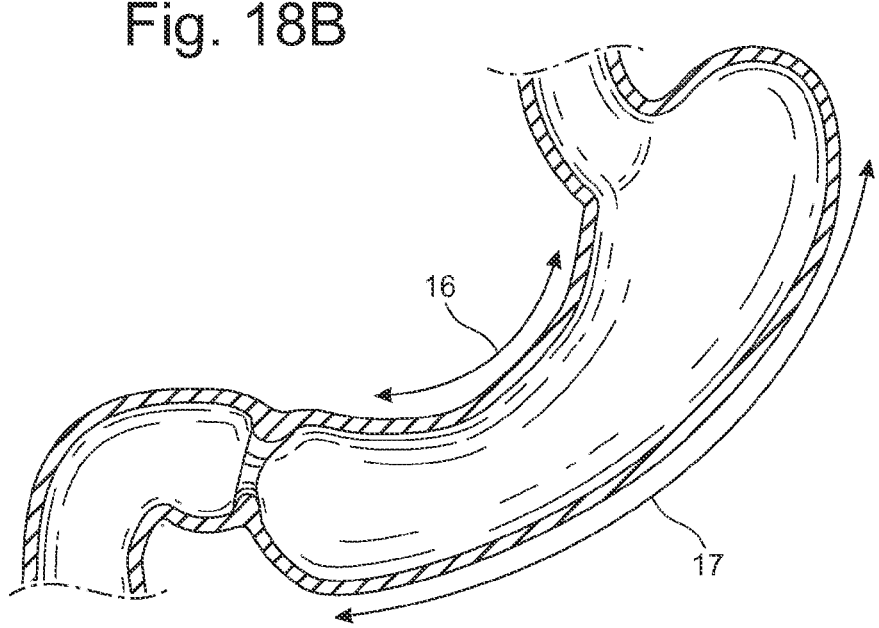
FIG. 18B depicts a side view of a cross-section of a stomach showing its approximate shape when undergoing contractions due to peristalsis.

In any of the embodiments discussed herein, the positioning element 25 may be constructed of materials or sized to contact the upper and lower stomach at the same time or may toggle to intermittently contact the upper or lower stomach. As mentioned above, the stomach experiences peristaltic waves when something is swallowed. FIG. 18A depicts a stomach cross-section showing the Z line and gastroesophageal ("GE") junction 38, the cardia or cardiac region 40, the fundus 41, the pyloric region 42 which includes the pyloric antrum 43, the pylorus 18, the stomach side walls 20, and the duodenum 19. FIG. 18B depicts the stomach's lesser curve 16 and greater curve 17. The pylorus is the muscular passageway that passes from the stomach to the intestines, and includes the pyloric valve.

FIGS. 18A and 18B respectively show a representation of the stomach profile when the stomach is at rest and when the stomach is fully contracted during peristalsis and the change in stomach diameter and length. Due to the change in stomach profile, it may be advantageous to have a design that can flex or accommodate the change in stomach profile to allow the design to slide, translate or flex as needed, but maintain the relative position of the lower stomach element 26.

Figure 19B:
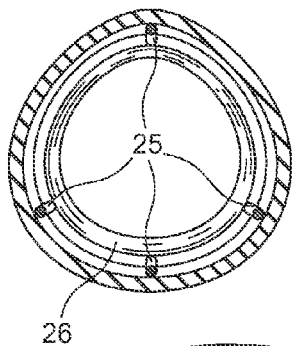
FIG. 19B depicts a back view of the lower stomach element of FIG. 19A.
Figure 19A:
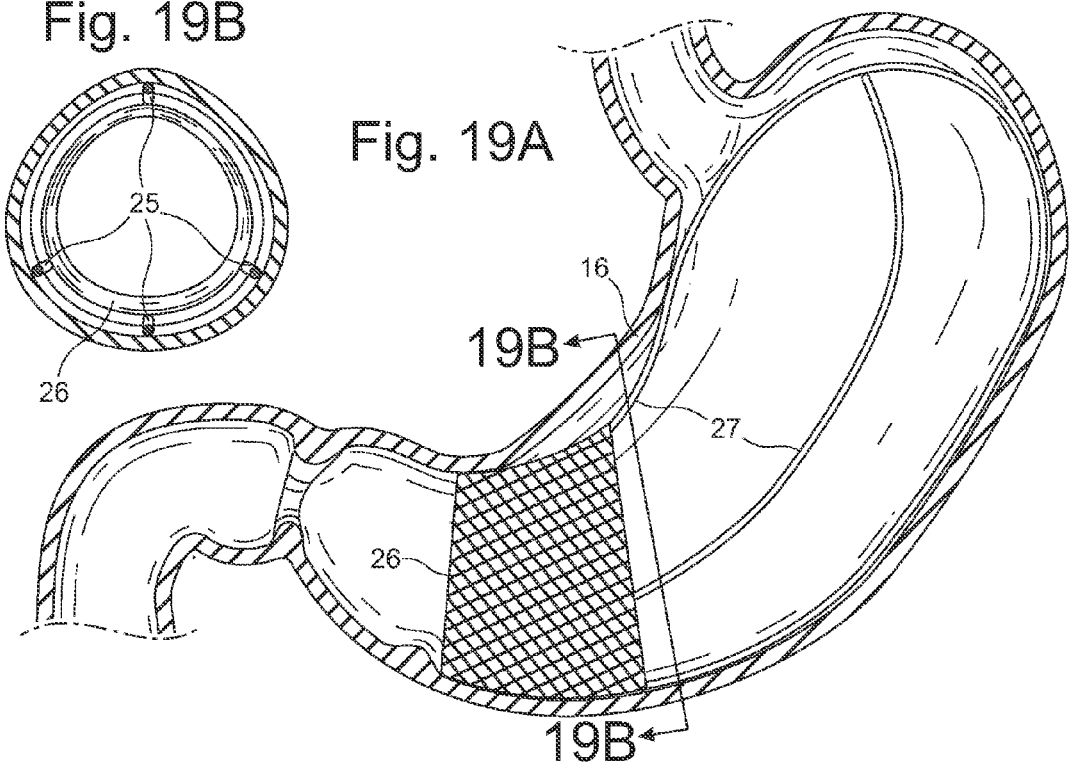
FIG. 19A depicts a side view of an embodiment of the bariatric device of the present invention, located within a cross-section of a stomach.

In the two-element design shown in FIGS. 19A and 19B, the positioning element 25 attached to the lower stomach element 26 could follow the natural curve of the stomach to match the greater or lesser curve of the stomach 17, 16, or could have both. This would aid in the seating of the device 10 in the stomach after placement. The positioning element 25 could have one or more positioning members 27 connecting to the lower stomach elements 26. However, these members should have enough flexibility or have an accommodating feature to allow for natural peristalsis to occur, natural sphincter function to occur and to not cause erosion or irritation of the stomach wall or significant migration into the esophagus 32 or duodenum 19. There could also be struts or supports that help to support the geometric shape of the lower stomach element to the positioning element 25. The positioning element 25 could also be a spiral or multiple spirals to create a flexible structure or portions that are spirals. The positioning element 25 could also be bisected into two members that stack, telescope, translate or articulate to accommodate peristalsis. FIG. 13B depicts an embodiment with this translating feature as an expansion joint 75. The positioning element 25 could also have a joint such as a ball and socket type joint or may be connected by magnets or by mechanical means. The positioning element 25 may be made up of two or more members 27, as shown in FIGS. 19A and 19B. As shown in the drawing, the lower stomach element 26 contacts the lower stomach or pyloric region 42. The positioning element 25 has four members 27, which are shown as curved wires, ribbons or tubes. One member 27 curves to match the lesser curve 16 and greater curve 17, while two other members 27 curve to match anterior and posterior sidewalls 20 between the lesser and greater curves 16, 17, and curve to contact the anterior and proximal surfaces of the stomach to maintain its position even during peristalsis. These members 27 could be connected to each other and the lower stomach element 26 in a variety of ways.

Figure 19C:
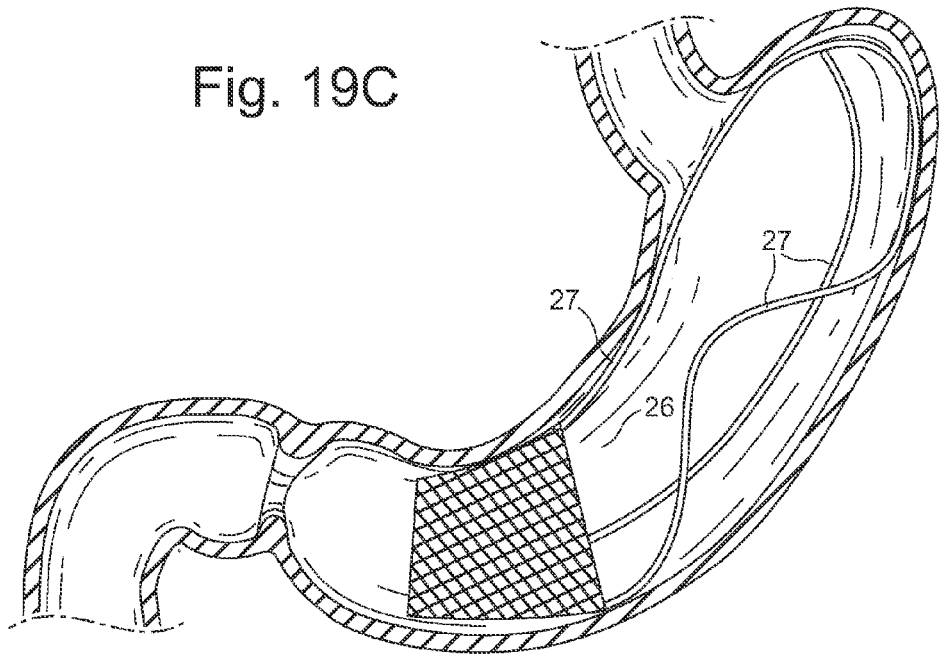
FIG. 19C depicts a side view of the embodiment of FIG. 19A, located within a cross-section of a stomach that is undergoing contraction due to peristalsis.

In another embodiment, peristaltic motion may cause the device 10 to move inside the stomach and could cause the lower stomach element 26 to slide from the relative locations. See FIG. 19C. During peristalsis, the greater curve 17 will shorten, and the member 27 that matches the greater curve could have a living hinge that could flex inward to a convex form. After the peristaltic action is complete, the hinge in member 27 may spring back to its original concave form. Using these concepts, additional members 27 for the positioning element 25 may be used beyond the three and four members 27 described here, and could be located in a variety of locations along the midline, lesser curve 16 or greater curve 17 or any combination.

In yet another set of embodiments, the bariatric device 10 may be self expanding. FIGS. 20A and 20B depict an alternative embodiment the positioning element is formed from 2 complete loops 51 arranged in separate planes, although the planes may be generally parallel. The loops 51 and the lower stomach element 26 may be self expanding. These elements could be self expanding or have a portion that is self expanding to allow the device 10 to flex with peristalsis, but maintain tension to spring open to apply pressure or contact and position within the stomach. The self expanding portion could be made of Nitinol, silicone, polyurethane, Teflons, stainless steel, super alloys, or other suitable materials or combinations of suitable materials. FIGS. 20A and 20B show a Nitinol wire mesh pattern 50 applied to a frusto-conical shape to create a shell. The Nitinol wire may act as a stiffening member within the lower stomach element 26, or within the first second elements 12, 13, discussed below. The Nitinol wire could be arranged in many different patterns to allow for the appropriate amount of self expansion while allowing the element to compress during peristalsis, but provide enough resistance to prevent it from migrating through the pylorus. The wire array pattern could include circular arrays, angular arrays, linear arrays, or other suitable arrays. The pattern could be woven or a continuous spiral. The Nitinol wire mesh array may be coated with silicone to create a smooth soft interface to the stomach. This coating may also limit the amount that the mesh pattern can compress to prevent the device from over compressing and passing through the pylorus.

The self expanding function may also assist in deployment by allowing the device 10 to compress and then regain its shape. A preferred method of deployment is to compress the bariatric device 10 into a long narrow shape, which is then placed in a deployment tube, sheath or catheter. The collapsed and encased device 10 is then guided down the patient's esophagus 32 and into the stomach, where the bariatric device 10 is released from the deployment tube or catheter. Once released, the device 10 would expand to its original operational shape. The stiffening member, such as Nitinol wire, may provide adequate stiffness to expand the elements into their operational shape, and maintain that general shape during operation, while allowing flexibility to accommodate peristalsis.

The positioning element may be constructed from 2 full loops 51 or 2 loops connected together to create a "FIG. 8" structure 52. The loops could be contoured to generally follow the curves of the stomach, and could be connected to the lower stomach element 26 in a variety of locations. The loops could be oriented to intersect at a variety of locations to provide different configurations with varying structural resistance and flexure points. For example, FIGS. 20A and 20B depict a bariatric device 10 where there are two separate closed loops 51, which cross in the lower stomach element 26 so that the wires do not obstruct the distal opening of the lower stomach element 26. The loops 51 are then aligned in a parallel pattern. Such configuration could allow for more uniform curved contact of the loops to the stomach.

In another embodiment, the two loops 52 are connected in a "FIG. 8" pattern where the loops are 52 crossed in the lower stomach element 26 and do not obstruct the distal opening of the lower stomach element 26. See FIGS. 21A and 21B. The loops 52 cross again outside of the lower stomach element 26 which causes the loops to create a structure which is biased to flare open. Such construction could aid the positioning in the upper stomach region. Where the positioning element loops cross, they may be joined together by a means of fixation to hold them together. These could be held together by adhesive or a separate joint connection 105. The shape of the joint connection could follow the shape of the positioning element or it could be a portion of a frusto-cone or other shape. The joint connection 105 could be placed in a variety of locations either along the lesser or greater curves 16, 17 or near the gastroesophageal junction. Alternatively, rather than crossing to form the FIG.-8, the loops 52 could be coupled together and be shape set so that they merely meet, then separate without actually crossing.

In another embodiment, the bariatric device 10 could also contain additional stiffening ribs 27 to better position the device in the upper stomach or to maintain the structure of the positional element 25 such as maintaining a distance between the positional elements to create a three dimensional structure that does not act in one plane. FIGS. 22A and 22B depict stiffening ribs 27 applied to the positioning element 25 (actually attached to the joint connection 105) to maintain the position of the device within the stomach by applying a member to contact the cardiac region of the stomach near the angle of His to better accommodate the fundic area. The stiffening ribs 27 could take the form of many different shapes such as a ring, a disk, a cone, frusto-cone, a sphere, an oval, an ovoid, a tear drop, a pyramid, a square, a rectangle, a trapezoid, a wireform, a spiral, a protuberance, multiple protuberances, a portion of any of the above shapes or multiples of any shape or other suitable shapes. The stiffening ribs 27 could also comprise an inflatable balloon or contain an inflatable balloon. The stiffening ribs 27 could contain features for adjustability to better fit the upper stomach and to maintain the general position of the lower stomach element. The stiffening ribs 27 could be in constant or intermittent contact with the upper stomach.

Figure 24:
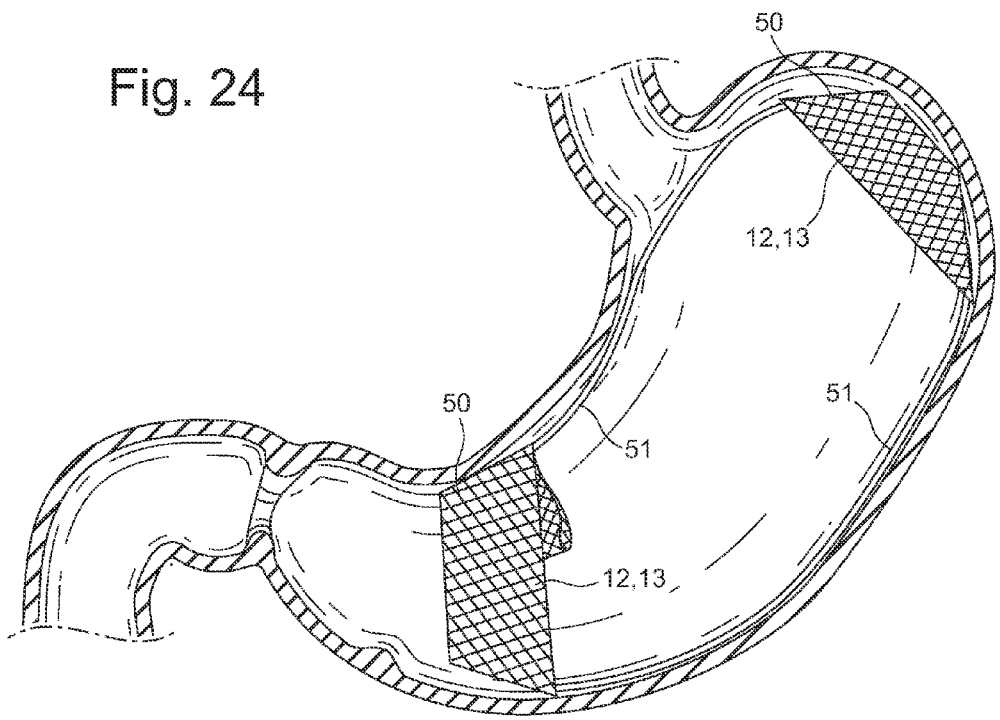
FIG. 24 depicts a side view of an embodiment of FIG. 23A in a folded, compressed state, located within a cross-section of a stomach.

In another embodiment, the device may contain a first element 12 and a second element, 13, either of which could engage the lower stomach and may have substantially the same shape. See FIGS. 23A, 23B, 23C, 23D and 24. These figures depict a device where the first and second elements 12, 13 are self-expanding flattened frusto-cones. In this embodiment, the first and second elements 12, 13, are comprised of members having a generally continuous broad curved or conical surface, as opposed to just one or more wires or a narrow structure in single plane. As used in the claims, the term broad surface refers to this type of surface, which may include the surfaces of cones, spheres, cylinders, and other curved surfaces. Such a broad surface may allow for increase surface area contact to apply light pressure against the stomach to engage stretch receptors, alter peristalsis and/or induce a neurohormonal response. Since the first and second elements 12, 13 are substantially the same shape, the device is symmetrically arranged on the positioning element 25 and can be placed in either orientation inside the stomach. In another variation, the device 10 may not be symmetrically arranged. In the symmetrical embodiment, the device 10 could migrate out of position and/or rotate, and then re-seat with peristalsis without concern of regaining the proper orientation. As shown in FIGS. 23C, 23D, and 24, when the flattened frusto-cone is placed or migrated into the lower stomach it may fold to create a wavy, convoluted structure. Because the structure is wide, the device may sit higher in the stomach, in the mid to lower stomach region as shown in FIG. 24. As used in the claims, the "mid stomach" includes the areas adjacent and proximal lower stomach 42. During peristalsis, the device 10 may move in the stomach, but may come to rest near the proximal antrum when the stomach is at rest or it may sit lower. Similarly, the positioning elements 51 used in this embodiment have the same profile for the proximal and distal portions which have a wide profile and may prevent the distal of the first or second elements from contacting the pylorus, and may position the device to sit away from the pylorus. This folded structure may act as a restriction element, creating a tortuous path or a valve for chyme to pass through prior to passing through to the area adjacent to the pylorus and through the pyloric valve. The restriction element may aid in slowing gastric emptying. Although the figures show a device with a flattened frusto-cone, many other shapes may be used. These shapes could be could be a ring, a disk, a sphere, a portion of a sphere, an oval, an ovoid, a tear drop, a pyramid, a square, a rectangle, a trapezoid, a wireform, a spiral, a preformed wavy shape, protuberances, portions of the above shapes, multiples of any of the above or other suitable shapes. It could also be any other shapes previously described. These shapes could fold and change form once placed into the stomach to perform a different function such as slowing gastric emptying by creating a tortuous path. Similarly, the element could be pre-formed with folds or waves or living hinges. Given that the first and second elements 12, 13 may have the same shape in certain embodiments, and/or may be interchangeable in position within the stomach, the claims may refer to them as a first element and a second element.

Figure 25:
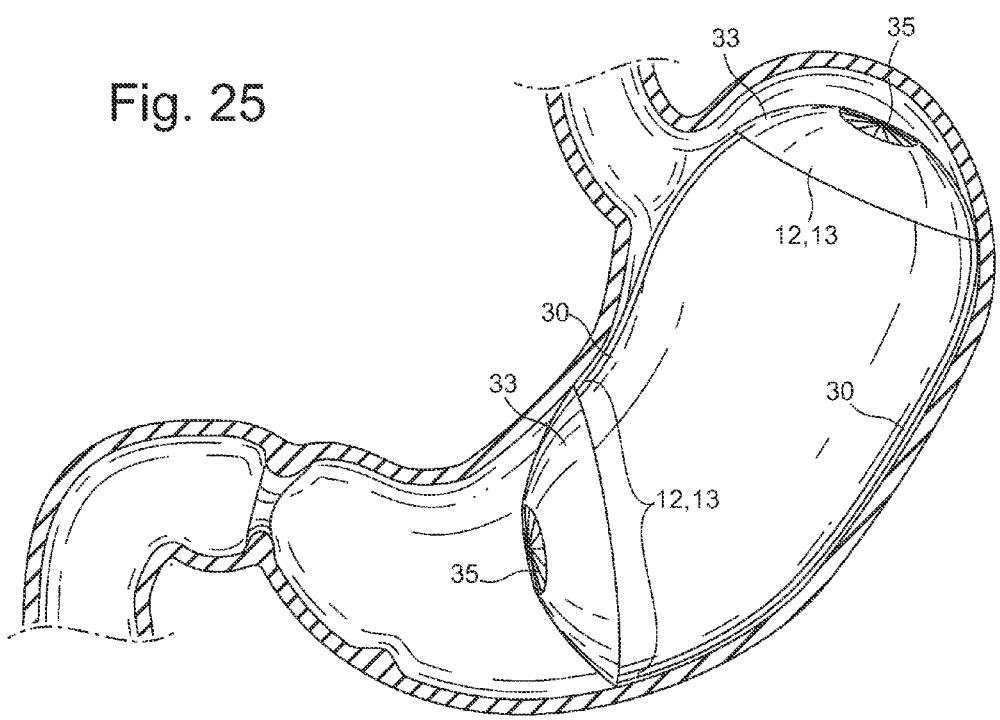
FIG. 25 depicts a side view of an embodiment of the present invention, located within a cross-section of a stomach.

The lower stomach element 26 may also contain a restriction element to slow gastric emptying. Such restriction element could comprise an additional membrane or valve. FIG. 25 shows a device with first and second elements 12, 13 that are hemispherical thin walled shells 33. The shape of the first and second elements 12, 13 could also be asymmetrical but similar to a cone or hemisphere. The first and second elements 12, 13 could be thin walled and could contain a lumen, no lumen, or a valve through which food could pass. These elements could also be thick walled where only the valve 35 portion has a different thickness to accommodate gastric emptying. FIG. 25 shows a valve 35 created by punching multiple crossing slits in an angular pattern through a thin walled membrane. In the case where there is no opening, the food would have to pass to the side the hemisphere or cone 33 which would have adequate flexibility to compress to allow the food to pass into the stomach. These restriction elements may delay gastric emptying resulting in the stretch receptors in the upper stomach in the stomach being stimulated by increased pressure throughout the stomach. In another alternative, the hemispherical shell 33 could have multiple grooves or channels or living hinges along the sides to aid in allowing food to pass around the perimeter. In the case where there is a lumen in the lower stomach element 26, it could be open or it could have a valve 35 that requires some force to allow food to pass through.

Figure 26B:
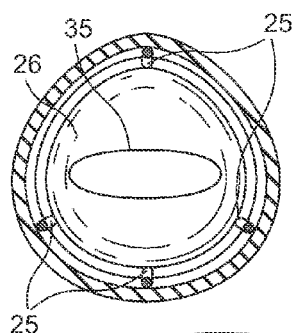
FIG. 26B depicts a back view of a lower stomach element from FIG. 26A.
Figure 26A:
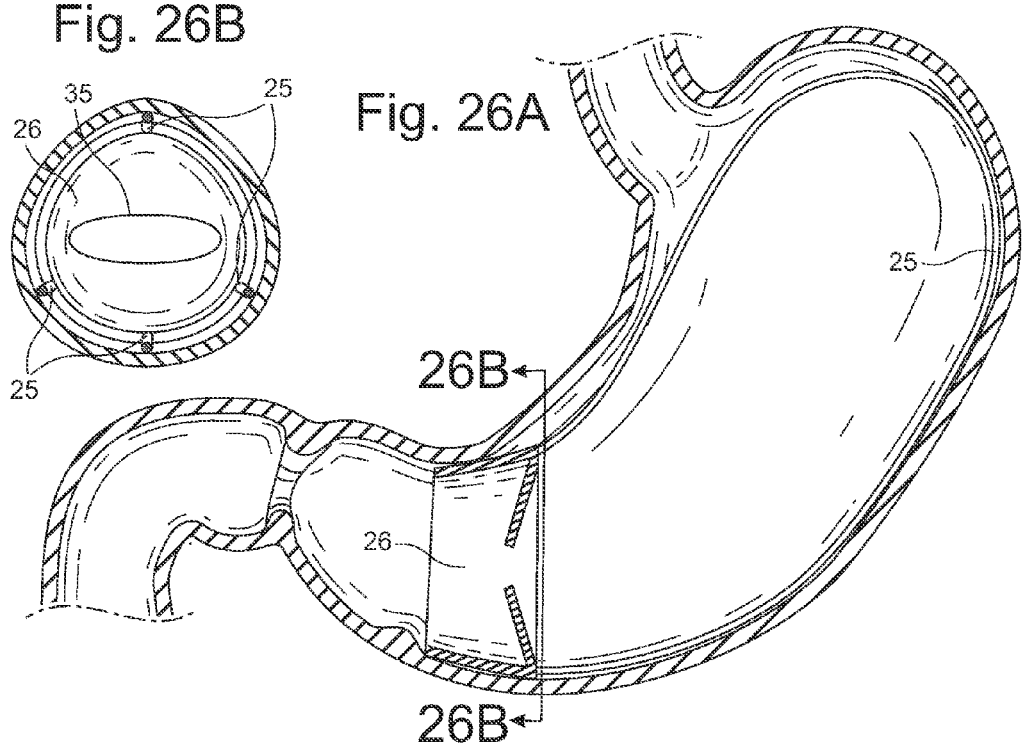
FIG. 26A depicts a cross-sectional side view of an embodiment of the present invention, located within a cross-section of a stomach.

Another variation of the restriction element to slow gastric emptying comprises a thin walled flexible membrane, small protrusions, wire loops, or fingers that extend from the inner surface of the lower stomach, first or second elements 26, 12, 13. FIGS. 26A and 26B depicts a device with a conical lower stomach 26 element with a thin walled flexible membrane 35 crossing through the center of the element. These figures depict a membrane with an oval opening, but the opening could be a slit, a hole or other shape. In this embodiment, the lower stomach element 26 has a wide profile and may maintain its position near the proximal antrum and the incisura angularis. In this embodiment, the device is not intended to contact the pylorus. In other embodiment, however, the lower stomach element 26 may be sized to contact the pylorus.

Figure 26C:
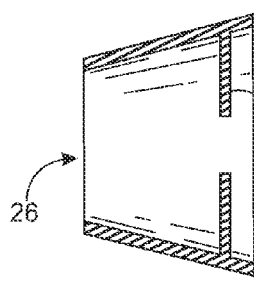
FIG. 26C depicts a cross-sectional side view of a variation of the lower stomach element from FIG. 26A.
Figure 26D:
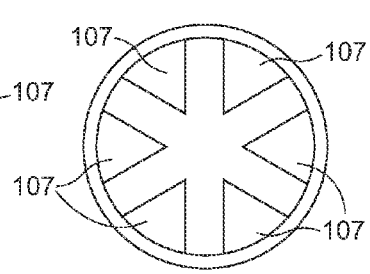
FIG. 26D depicts a back view of the lower stomach element from FIG. 26C.
Figure 26E:
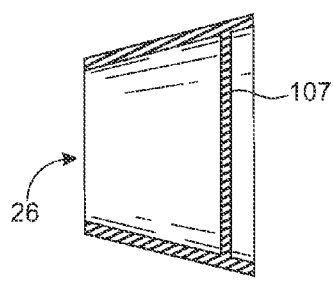
FIG. 26E depicts a cross-sectional side view of a variation of the lower stomach element from FIG. 26A.
Figure 26F:
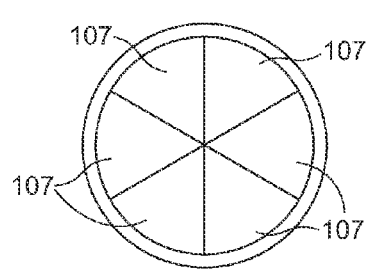
FIG. 26F depicts a back view of the lower stomach element from FIG. 26E.
Figure 26G:
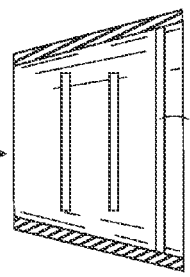
FIG. 26G depicts a cross-sectional side view of a variation of the lower stomach element from FIG. 26A.
Figure 26H:
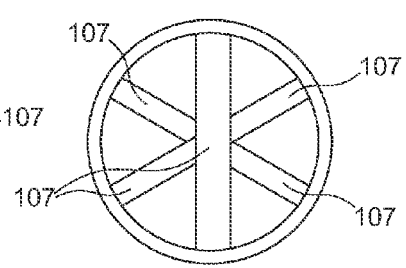
FIG. 26H depicts a back view of the lower stomach element from FIG. 26G.

FIGS. 26C, 26D, 26E, 26F, 26G and 26H show other examples of a restriction element, which may include a reduced lumen, valve or tortuous path to reduce the flow of food through the lower stomach element 26. FIGS. 26C and 26D show multiple flexible members 107 that extend from the internal surface of the lower stomach element 26 to reduce the flow of food. FIGS. 26E and 26F show a similar valve but with complete closure to increase the amount of restriction, but opens with pressure to allow for gastric emptying. Similarly, FIGS. 26G and 26H show multiple flexible members 107 that cross the inner surface of the lower stomach element 26 at different heights to slow gastric emptying. These elements could also be at the same height or close to the same height.

Figure 28:
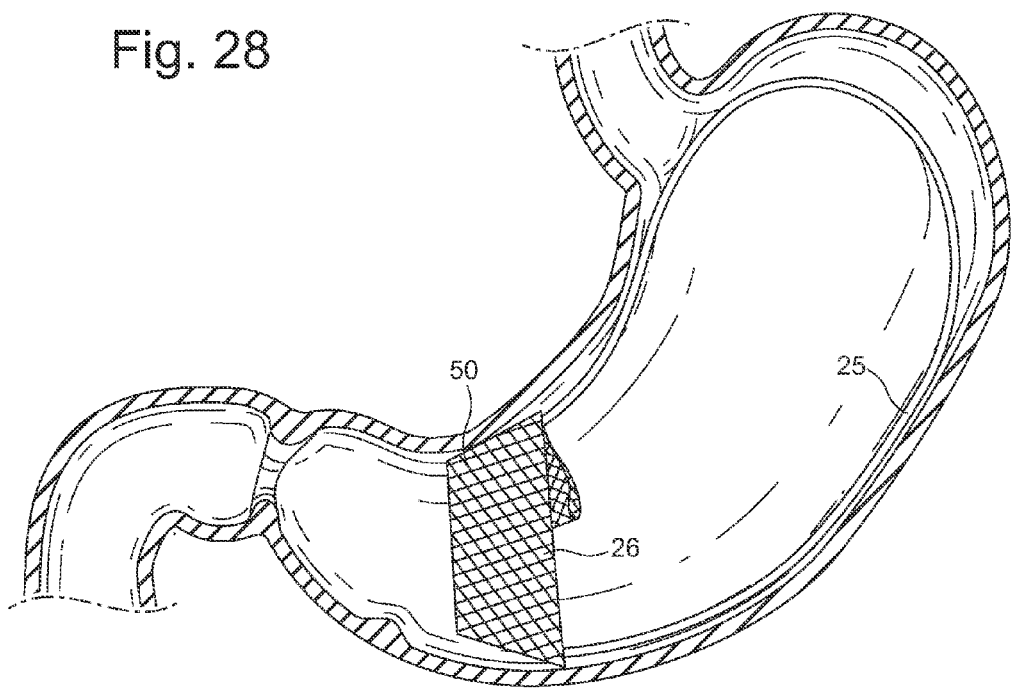
FIG. 28 depicts a side view of an embodiment of FIG. 27A in a folded, compressed state, located within a cross-section of a stomach.

In another embodiment, the same structure as described above for the foldable lower stomach element 26 as described in FIGS. 23C and 23D may be combined with a positioning element 25, 51 such as the wireform structure shown in FIGS. 27A, 27B, 27C, and 27D. This could combine the folded lower stomach element 26 with a positioning element 51. These embodiments would be intended to maintain its relative position. This embodiment may be able to move in the stomach or slide along the greater curve, but reseat into the lower stomach due to peristalsis compressing the device to seat in the lower stomach region. The curve and profile of the positioning elements where they connect to the lower stomach element may be wide enough to prevent the device from migrating too distal in the stomach. Alternatively, the device could compress more and migrate lower in the pyloric region. FIG. 28 shows a side view of the folded lower stomach element 26 and it shows an optional shape and size of the positioning element 51. The lower stomach element 26 and positioning element 51 could also sit in various other positions. In this embodiment, the positioning element 51 stands off of the fundus. The folded lower stomach element 26 has compressed into position and may slide along the greater curve until the positioning element 51 contacts the fundus, but then the device migrates back down into the lower stomach. Such configuration would allow for intermittent contact of the lower stomach and fundus.

Figure 29:
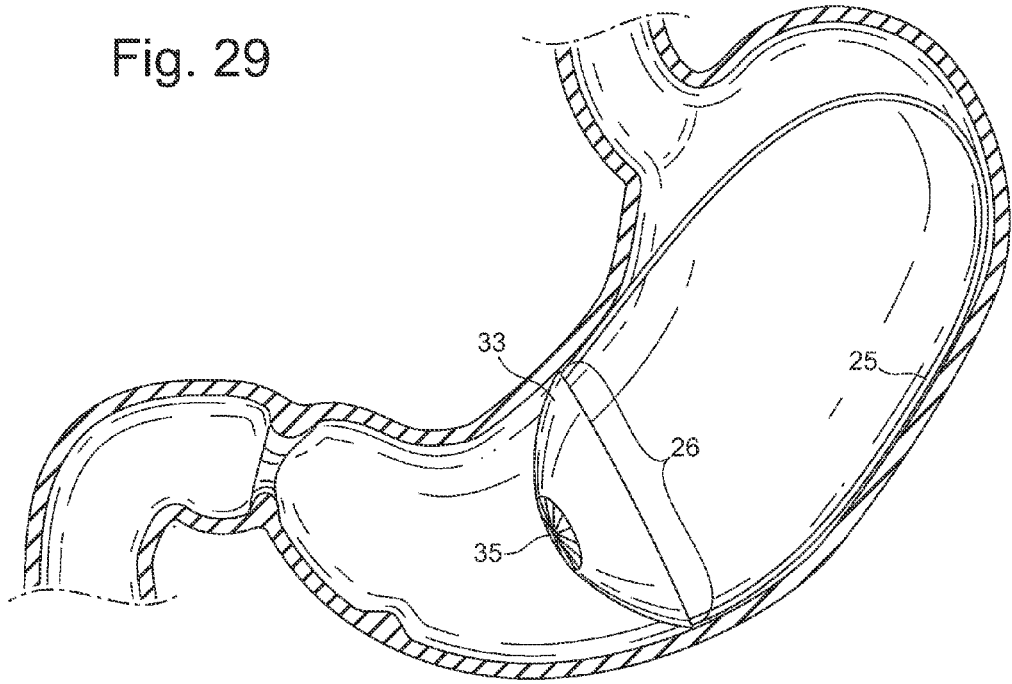
FIG. 29 depicts a side view of an embodiment of the present invention, located within a cross-section of a stomach.

FIG. 29 shows another variation of this embodiment where the lower stomach element 26 is a thin walled hemisphere with a valve 35. Due to the wide profile of the lower stomach element 26, this device will tend to sit in the mid stomach, but could sit lower pending on the lower stomach element sizing. FIG. 29 shows another optional shape for the positioning element 26 where the device could slide along the greater curve 17, or move proximal then distal, and then reseat in the lower stomach during peristalsis. Alternatively, the lower stomach element 26 could contain an open lumen.

Where the positioning element 51, 52 is formed from loops, the loops could be formed from Nitinol wire. The Nitinol wire used for the positioning elements or any elements in the device could be passivated to improve acid resistance. They could also be coated in an acid-resistant coating 53 such as silicone or silicone covering, PTFE, or other suitable coating, or not coated. These loops could also be made of spring steel, stainless steel, super alloys, Teflons, polymers or other suitable materials or combinations of materials. The loops could be closed or connected in a variety of ways. For the example of Nitinol, the loops could be closed by a glue joint where the wire loop ends are glued inside of another tube. They could also be closed by a crimping, swaging, welding or joined by a mechanical mechanism. The loops could also be left open, if a feature is added for adjustability, such as a multi-member translational element, and it is preferred to have the loops open with both ends fixed to the elements as needed.

In another embodiment, the device 10 may consist of a single lower stomach element 26 with a longer shape than previously described. The lower stomach element 26 could take any of the previously described shapes such as a cone, folding cone, preformed folded wire form, hemisphere, any shape disclosed herein or other. The lower stomach element 26 could move into position based on peristalsis. Similarly, weights 39 could be added to the distal portion of the lower stomach element 26 to guide the element to seat lower in the stomach. FIG. 30A shows a bariatric device 10, constructed of a single lower stomach element 26. The size and length of the lower stomach element 26 could vary to encourage the device to remain seated in the proper location. FIG. 30A shows a lower stomach element 26 that contacts the body of the stomach. The size of the lower stomach element 26 may be longer or shorter than this figure to stay positioned in its intended location. As previously described this element could contain a restrictive element. FIG. 30A shows a valve 35 which could create a restriction. Although the valve 35 is shown as oblong, it could also be a slit or round or other shape. FIGS. 30C and 30D show multiple protrusions extending from the inside surface to restrict flow. FIG. 30E shows a top view of a similar structure but with complete closure to increase the amount of restriction that will open under pressure during peristalsis. FIG. 30C also shows some weights or weighted elements 39 that could be applied to the inner surface of the lower stomach element 26. These weights could be used to orient the device distally and seat into the pyloric region. Alternatively, the lower stomach element 26 could be fixed into the lower stomach with sutures or fixation elements 36. By applying multiple weighted pads, it allows the device to maintain flexibility and compressibility. However a less flexible, or rigid weight could also be applied which could create a rigid structure. Flexible weights could also be applied. FIG. 30F shows an example of a circumferentially weight ring added to the inside of the device. The lower stomach element is preferably self-expanding to apply radial pressure to or contact with the stomach walls, and to maintain the structure from collapsing or passing through the pylorus. Similarly, FIGS. 30F and 30G show multiple flexible members 107 that cross the inner surface of the distal stomach element 26 at different heights to slow gastric emptying. These elements could also be at the same height or close to the same height.

Figure 31:
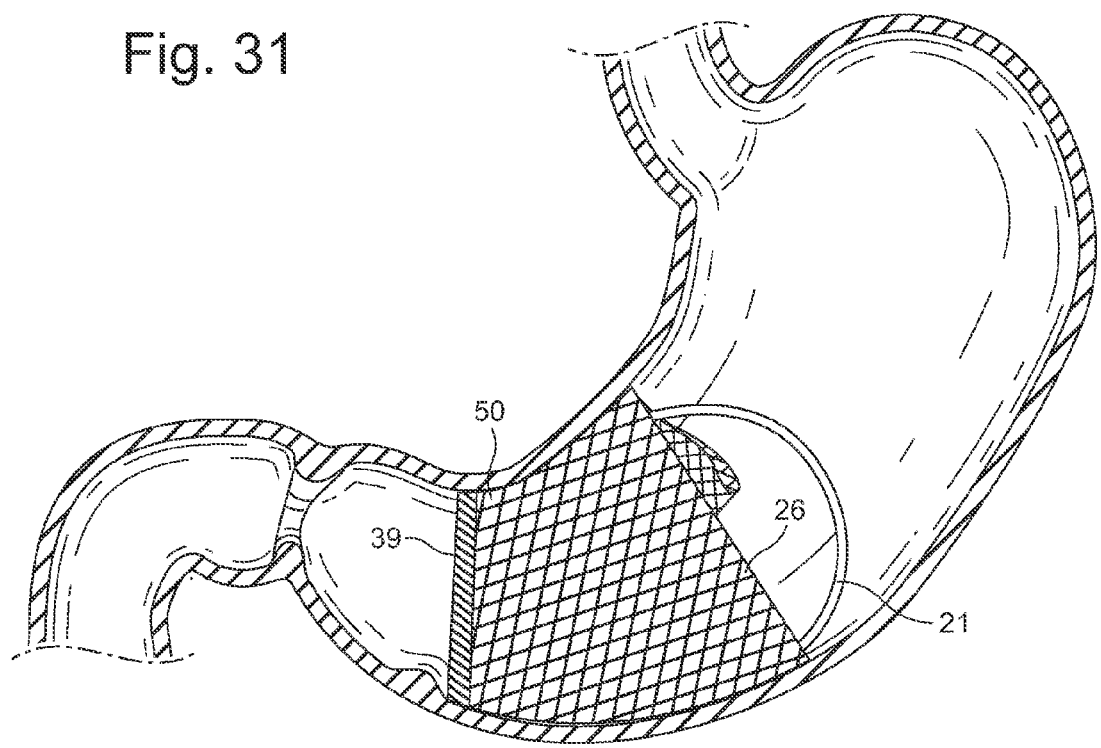
FIG. 31 depicts a side view of an embodiment of the present invention, located within a cross-section of a stomach.

FIG. 31 shows another variation of a folded lower stomach element 26, which could also vary in length and size. This device could also contain weights to encourage proper orientation and seating within the stomach. The device could also contain a stiffening element 21 to further improve the structural integrity of the device so that it cannot pass through the pylorus. As shown in FIG. 31, the stiffening element 21 is a round shape. The bariatric device 10 could contain multiple stiffening elements 21. These stiffening elements 21 that could cross to create a joint similar to previously described positioning elements described in FIGS. 23A and 23B, or could be incorporated into the lower element surface 26 structure or other.

Figure 32A:
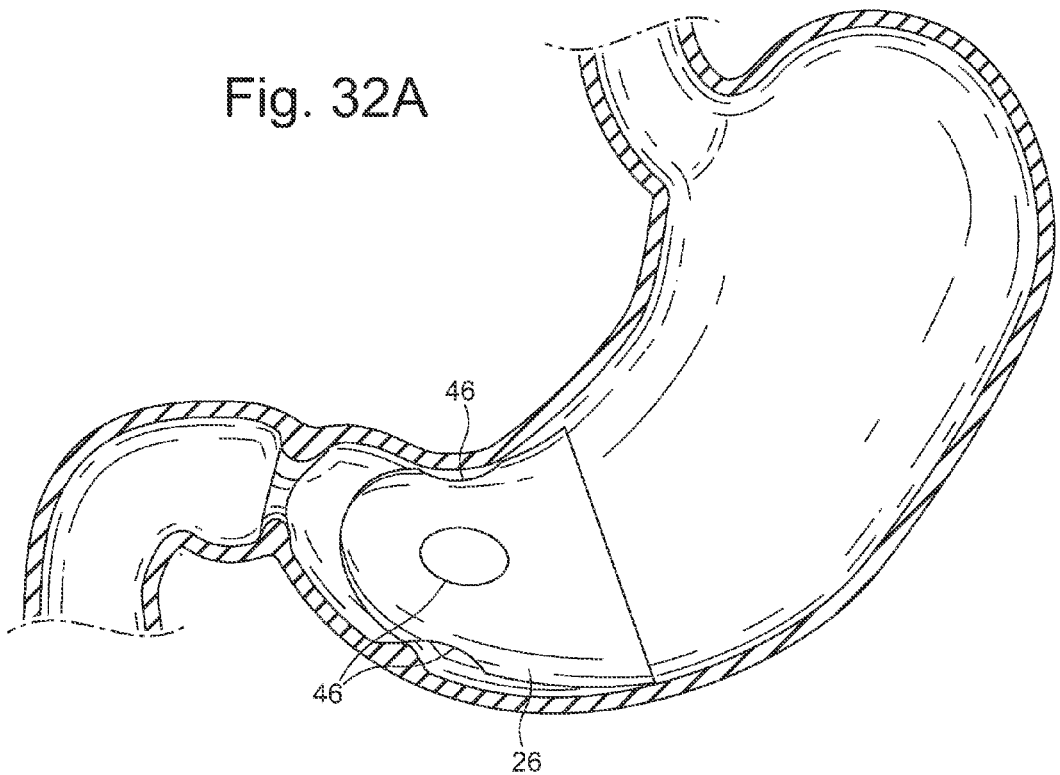
FIG. 32A depicts a side view of an embodiment of the present invention, located within a cross-section of a stomach.
Figure 32B:
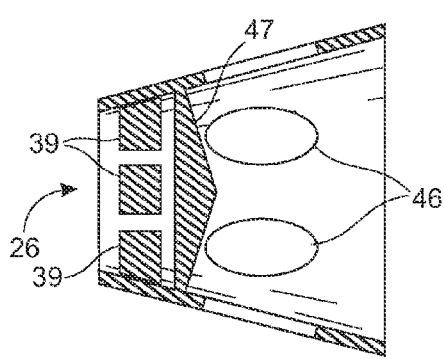
FIG. 32B depicts a cross-sectional side view of a variation of the lower stomach element from FIG. 32A.
Figure 32C:
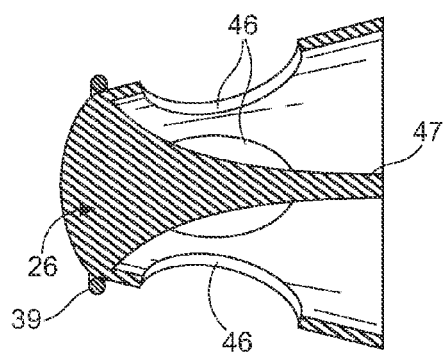
FIG. 32C depicts a cross-sectional side view of a variation of the lower stomach element from FIG. 32A.

In another embodiment, the device 10 may consist of a single lower stomach element 26 with a closure at the distal end of the device, but with multiple side wall openings 46. The lower stomach element 26 could take any of the previously described shapes such as a frusto-cone, a folding frusto-cone, preformed folded wire form, hemisphere, a frusto-cone or cone with a full radius at the end, or any shape disclosed herein or other. The lower stomach element could move into position based on peristalsis and could sit in the mid to lower stomach, but be of sufficient shape and resistance to resist passing through the pylorus. FIG. 32A shows a device with a rounded, atraumatic end. When the device is positioned in the mid to lower stomach, the side wall openings 46 would be in close contact with the stomach wall to create a reduced passage to reduce the speed of stomach emptying. Another feature of this device would be increase the pressure inside the stomach as the stomach is trying to empty itself. The lower stomach would contract to attempt to empty the stomach and this increase pressure would be applied to the upper stomach as well. This increased pressure would engage stretch receptors throughout the stomach including those located in the upper stomach or cardia to induce a neurohormonal response throughout the stomach and not just in a localized area due to contact. During peristalsis, the device could flex between the peristaltic waves to allow food to pass through the side holes. To modulate the rate of emptying, the device 10 could have features along the outside surface such as grooves, channels or raised surfaces to create a space between the stomach and the device 10 where food could drain through the side wall openings 46. The lower stomach element 26 could also contain living hinges along the side walls to encourage controlled compression and drainage through the openings. As shown in FIG. 32A, the distal end the lower stomach element would be closed, but could contain a funnel or directional flow feature 47 at the distal end of the device to funnel or direct food contents toward the holes such as a cone, a taper, a hemisphere or a central core or protrusion to allow food to pass into the device and direct it to the openings 46. This would prevent food from becoming trapped at the bottom of the lower stomach element 26. FIG. 32B shows an internal taper that would direct food toward the holes. This feature could be a thin membrane or a solid section at the distal end of the inside surface of the device 10. FIG. 32C shows another variation of the lower stomach element where a funnel feature 47 is constructed of a central core to direct food towards to the openings 46. This core could be solid or a thin walled structure.

Similarly, weights 39 and/or an anti-migration element 49 could be added to the distal portion of the lower stomach element 26 to guide the element to seat lower in the stomach as shown in FIGS. 30B and 30C. This would allow the device to push out of position based on a retrograde wave and then reseat later. Alternatively, the device could also be coupled with a positioning element 25 to maintain the relative position. The device could contain one or more openings 46, and these openings could take several shapes such as a round, an oval, a rectangle, a square or other. Where multiple openings were used, they could be arranged in a variety of patterns. The lower stomach element is preferably self-expanding to apply radial pressure to the stomach walls, and to maintain the structure from collapsing or passing through the pylorus. However the openings or surfaces around the openings 46 may be constructed of softer more compliant material to encourage sealing or compliance with the stomach wall.

The contact members of the elements may be comprised of a variety of materials. For example, the Nitinol wire pattern of the lower stomach, first or second, elements 26, 12, 13 may be exposed for direct contact with the stomach or the wire could be covered or sealed in another material, such as silicone, PTFE, polyurethane or other suitable materials. The contact and stiffening members of the elements may be separate, entirely integrated, or both. For example, if the lower stomach element 12 is made entirely of Nitinol wire, the wire acts as both a contact member and a stiffening member. The same would apply if an element were made entirely of silicone; the silicone would act as both a stiffening and contact member. In another embodiment, where Nitinol wire is embedded in another material such as silicone, the Nitinol wire acts as a stiffening member and the silicone acts as a contact member. In another embodiment, the Nitinol wire may be partially exposed and partially covered by the silicone (and/or on the interior of the element), in which case the Nitinol wire acts as both a stiffening and contact member. In certain embodiments, the combination of materials may act as a stiffening member. For example, an embodiment where the contact member is silicone with Nitinol wire embedded, the silicone may act in conjunction with the Nitinol to provide more stiffness than the Nitinol could achieve alone. Various combinations of stiffening and contact members may be apparent to those skilled in the art.

As mentioned above, a preferred device 10 has adjustability or adaptability to match any changes in the patient over time. A variation of the above embodiments would be to allow the device 10 to be adjustable via an adjustment element 60. This adjustability could be in the length, shape, angle or stiffness of the lower stomach, first, second or positioning elements 26, 12, 13, 25. Similarly, different sized devices could be manufactured and the device replaced with a different size.

The bariatric device 10 could be adjustable to allow for adjustment of the sizing of the device 10 at the time of placement or could be adjusted at a later time. This adjustability could be achieved by having a variable spring tension in one of the elements to allow the device 10 to extend, contract, or distort as needed. It could also be achieved by adding an expansion joint 75 in a member to elongate or compress as needed. This expansion could be a manual adjustment performed by the physician in the office through a gastroscopic procedure. This expansion could be achieved by various mechanisms, including but not limited to those operated by: rotating a threaded member, ratcheting backwards or forwards, a hydraulic mechanism, a pneumatic mechanism, a cam, a tension mechanism, a telescoping mechanism, a spring or other elongation or contraction mechanisms, or any combination of the above. The outer surface of the positioning element 25 is preferably smooth with rounded or gently angled edges to prevent irritation of the stomach during peristalsis, although sharp angles may be preferred in some applications. To create a smooth interface, these elements could be encased in a sleeve or sheath that could be removed or remained fixed during the expansion. A sheath may not be required if the expansion joint 75 is designed with smooth contours on its own.

Figure 33A:
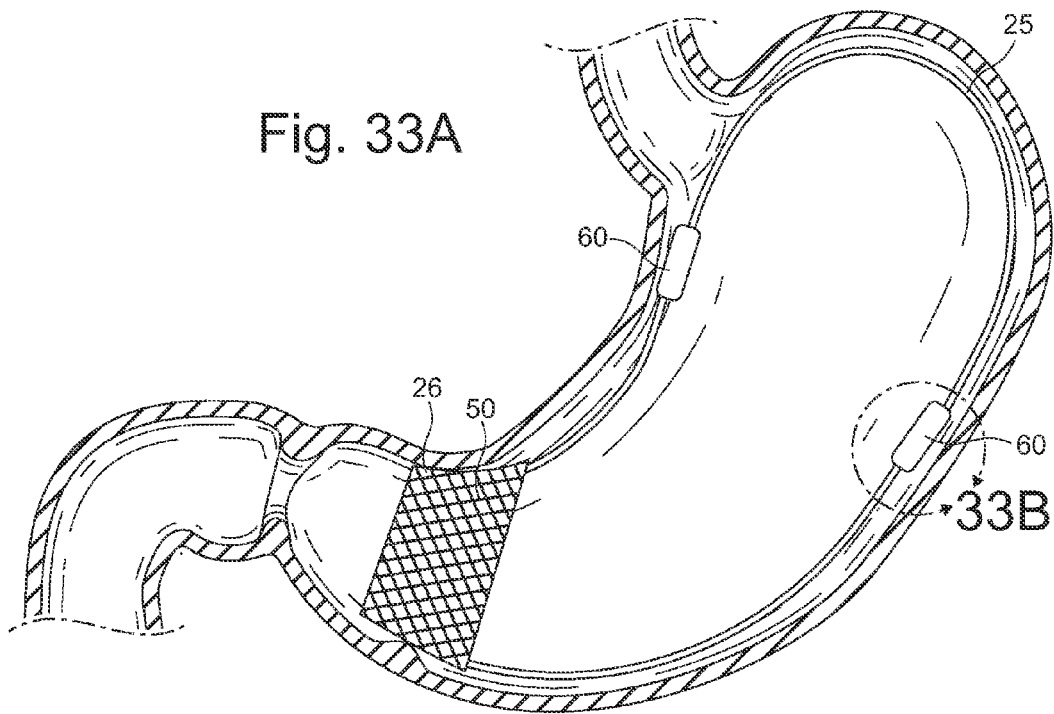
FIG. 33A depicts a side view of an embodiment of the present invention, located within a cross-section of a stomach.
Figure 33B:
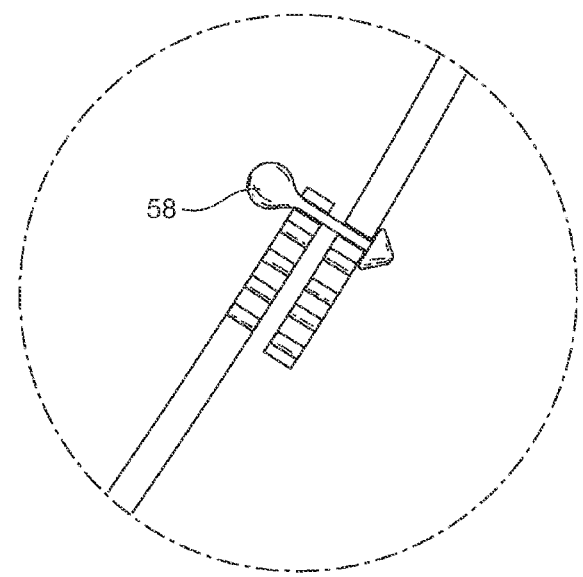
FIG. 33B depicts a cross-sectional side view of an adjustment mechanism shown in FIG. 33A.

FIG. 33A shows another embodiment with a self expanding lower stomach element 26 and a positioning element 25 within the stomach. The positioning element 25 has an adjustment element 60 such that the device length could be modified to increase or decrease the force or pressure that is applied to the distal stomach or to accommodate different sizes or shapes of stomachs. Adjustability of the length would allow the device to be adjusted to custom fit the device to the patient. As shown in FIG. 33B, the length could be adjusted by a variety of means such as a positional feature with multiple holes and a pin 58 to allow the element to slide along itself until the desired length is achieved and a pin or feature is placed into the matching holes to fix the length. This could also be achieved with two articulating ribbons or a piston inside of a cylinder, and a set screw to fix the length or other adjustability feature.

Manual Actuation

The device 10 could also be adjusted by manual means inside the stomach by using a gastroscopic instrument to come into direct contact with the device 10.

Figure 34A:
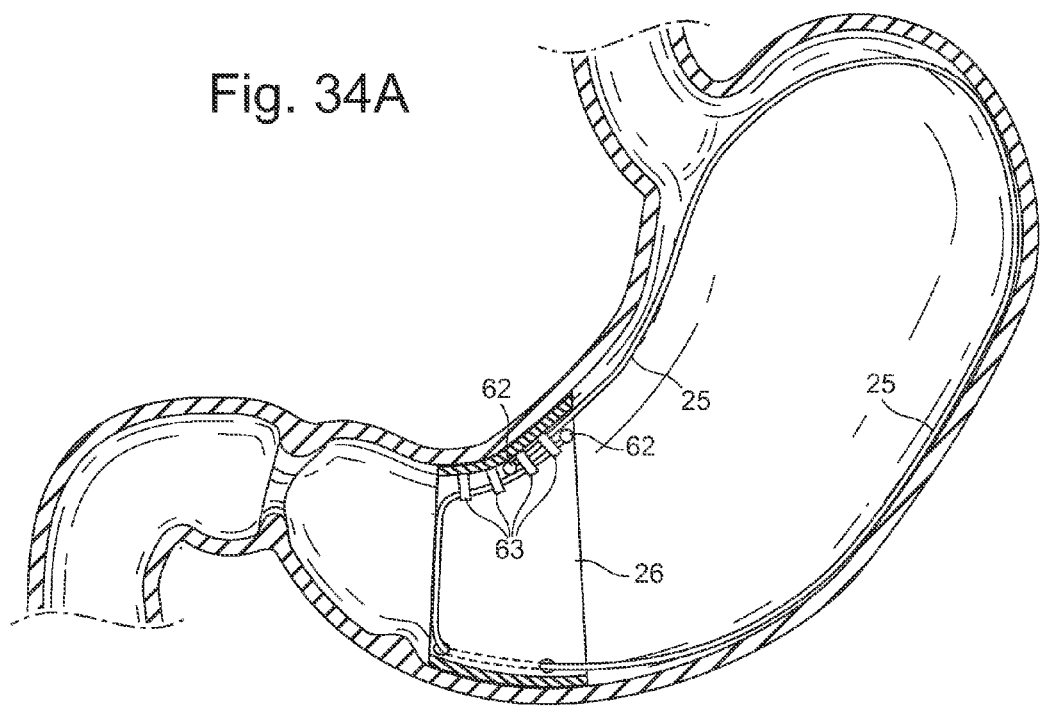
FIG. 34A depicts a cross-sectional side view of an embodiment of the present invention, located within a cross-section of a stomach.
Figure 34B:
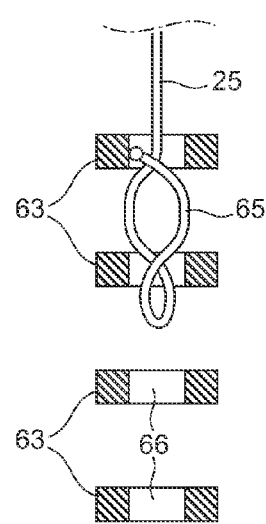
FIG. 34B depicts a cross-sectional side view of an adjustment mechanism in a compressed state.
Figure 34C:
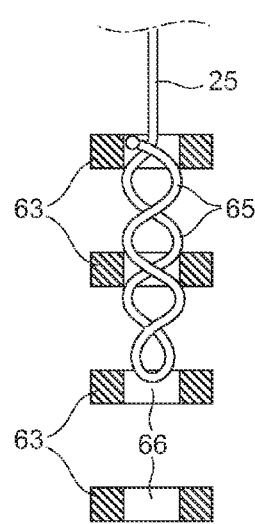
FIG. 34C depicts a cross-sectional side view of an adjustment mechanism in a compressed state.
Figure 34D:
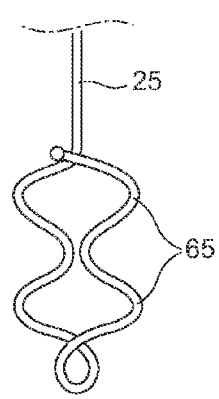
FIG. 34D depicts a side view of an adjustment mechanism in an uncompressed state.

- The instrument could also act as a pusher or puller to activate a pulley mechanism or a clipping mechanism. For example, the positioning element 25 could be a ratchet or strut with multiple positional features such as holes, grooves, teeth or wedging action. The device 10 could have a feature to engage the ratchet teeth or positional features such as a pin or clip or other. The instrument could retract the pin or compress the clip and then reposition this feature in the next available location.
- In another embodiment, the members of the positioning element 25 could have multiple beads or spheres 62 that are captured by a cuff or ring retainer on the lower stomach, first or second elements 26, 12, 13. An instrument could be used to expand the cuff to pull the bead through for positioning. Similarly, the cuff could have a keyway retainer feature that allows the bead to only fit through a specific location and then lock into position where the beads connect to the wire or ribbon or tube.
- FIGS. 33A and 33B show an example of a 2 element device where the positional element has features to allow for length changes. FIG. 33B shows and example of how a pin could be used adjust the length of the positional feature by placing it into a hole pattern on the 2 members of the positional element.
- FIGS. 34A, 34B, 34C and 34D shows several examples of compressible clips 65 acting as a "bead" or positional feature that could be used for adjustability. For example a retainer strap 63 of silicone could be bonded on both sides to create a narrow passageway 66 where the clip 65 could be placed in the compressed position, and then expand open after passing through the strap 63 to maintain its position. Several straps 63 could be bonded in a row to create several positional locations. FIG. 34D shows the clip 65 in is open, relaxed state, where 34B and 34C show the clip 65 in a compressed state where it can pass through the retainer strap 63.
- Another option for adjustability would be to use a locking ring to fix the location of the positioning elements 25 into the lower stomach element 26. The lower stomach element 26 could have several positional features connected to it. The positioning element 25 could also have several positional features attached to it. When the positional features of the lower stomach element and positioning loop are aligned, a locking ring could be placed inside to hold the position of the elements together and to alter the length of the whole device 10 to be longer or shorter. In another embodiment, the ring could be fixed to the lower stomach element 26 and compressed to capture the positional features located along the positioning element 25.

In another embodiment, an instrument could act as a screw driver to rotate a member to thread the two elements closer or farther apart. The instrument could also have a needle to inject fluid into an inflation element 74. Such an element may be a self sealing membrane to increase or decrease the length, diameter or stiffness through positive displacement of an inflatable body as shown in FIG. 9A or 35A. The self sealing membrane could be an injection port or it could be a self sealing surface on the inflatable body, or the entire inflatable body could be comprised of a self sealing surface as shown in FIG. 9B. In all descriptions below, the term inflation element 74 can also refer to an injection port or to an area on the inflatable body with a self sealing membrane. The inflation element 74 or self sealing membrane could also be a self sealing valve which can be accessed by a blunt needle or tube to allow access to add or remove fluid. The valve could be attached directly to the inflatable member or it could be attached by a tube. FIG. 35A shows an inflation element 74 fixed to the lower stomach element 26 or the positioning element 25. This valve or port could be connected by a fluidic path to an expandable joint such as a sealed inflatable body inside of an expansion joint 75 such as a piston and cylinder. The valve could be accessed by an endoscopic instrument with a blunt end, while an injection port could be accessed by an endoscopic instrument with a non-coring needle where saline or other suitable fluid could be injected or removed from the port which would allow the inflatable body to expand or contract to control the length of expansion. Although this figure shows one expansion joint 75, the device 10 could contain one or more with a manifold set up to deliver fluid from the port to all of the expansion joints. In an alternative embodiment, the system could also have an expandable joint 75 such as a syringe type joint which would not require a sealed internal inflatable body.

In another embodiment, the lower stomach element may include a linearly expandable body 68, as shown in FIG. 35B. This figure shows a variation of the inflation element 74 where a valve is attached to the lower stomach element by a retractable inflation tube 106. The retractable inflation tube 106 may be constructed of a coiled tube, which may be may be contained in a housing or not contained in a housing. Alternatively, the retractable inflation tube 106 may be attached to a separate leash or tether. The inflation element 74 can be grasped inside the stomach using a standard grasper or snare, and then pulled up the esophagus for access outside the body while maintaining the device inside the stomach. The inflation element may be a slit valve that can be accessed by a blunt needle or small diameter instrument to push through the valve to allow fluid to be added or removed.

After the appropriate volume of fluid has been added, the retractable inflation tube 106 can then be placed back into the stomach. Preferably, the retractable inflation tube 106 would be designed so that it would not pass through the pylorus. The inflation element 74 is located along the lower stomach element where fluid can be added or removed to expand the length of the balloon and the device 10. Any inflation element could be combined with any embodiment that includes an inflatable member.

A gastroscopic instrument could also deliver heat directly to an expandable joint such as a heat expanding mechanism (such as one made of Nitinol) for expansion of a wax or wax-like expansion member.

For example, a Nitinol clip could clip into a positional location on a strut. The instrument could heat the clip to release and then reposition it into a different location, remove the heat and allow the clip to re-engage the positional feature to lock it into place. Alternatively, the clip could be cooled to contract, removed from a specific position, repositioned and then allowed to return to a higher temperature to re-engage a different position.

The instrument could also have an inflatable body or a balloon to allow for physical contact with the device 10 to disengage a feature for repositioning into another location.

Figure 36:
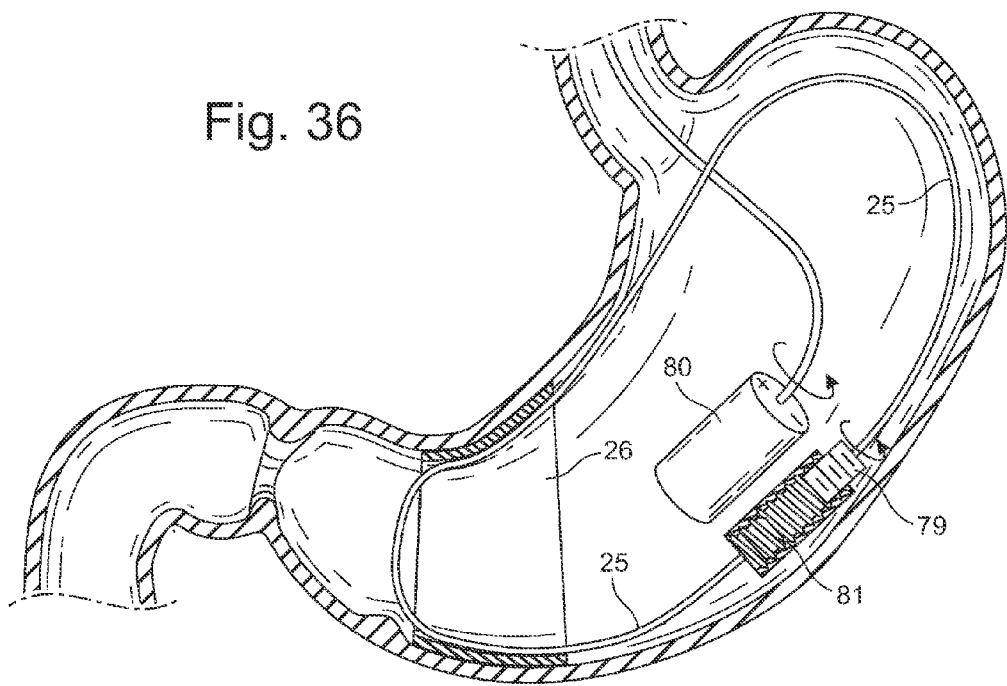
FIG. 36 depicts a cross-sectional side view of an embodiment of the bariatric device of the present invention, located within a cross-section of a stomach.

Magnetic actuation. Another adjustment mechanism could use magnets. See FIG. 36.

For example, the positioning element 25 could contain a thread with a magnetic nut 79 placed over it. Another strong magnet, the controller magnet 80, could be placed in close proximity to the implanted magnet to cause it to rotate. The rotation of the controller magnet 80 could create a magnetic field which would cause the internal magnet 79 to turn allowing it to advance and retreat along the threaded member 81.

The controller magnet 80 could either be external to the body or it could be placed on the end of a gastroscopic instrument for close proximity.

The controller magnet could be a magnet or an electromagnet to increase the intensity of the field and to improve magnetic coupling to ensure actuation.

The controller magnet 80 could also be multiple magnets to improve magnetic coupling.

Another means of manually adjusting the length of the device 10 would be to have modular pieces that could attach or adhere to the lower stomach elements 12, 26. For example, an additional frusto-cone could be placed over the lower stomach element 26 to increase the length of the overall design. Several could be stacked together to create a variety of lengths. Stacking frusto-cones could also be distanced from one another with a balloon on either frusto-cone to increase the distance between the two.

A variation of this embodiment would be to have an additional member that could be collapsible or compressible and inserted down the center of the lower stomach element 26. Once it passes the lower stomach element distal surface, the modular element would expand and attach to the outer surface. Several modular elements could be stacked together to create a variety of lengths.

An alternative embodiment could have an additional element that could also pass down the center of the lower stomach element 26 and expand past the distal surface, but with a clip that would allow it to remain clipped to the inside surface. The attachment mechanism could be positionally based so that the element could be repositioned to several locations for a variety of lengths.

There could be several other means for manually actuating the design for repositioning.

As another variation of the above embodiments, the manual expansion mechanism could be adjusted remotely by an apparatus outside the body, and/or automated. The expansion could be achieved by a small motor that could be driven by an implanted power source or driven by a remote power source such as induction. Energy could also be supplied by an RF signal, kinetic energy, ultrasound, microwave, cryogenic temperatures, laser, light, or thermal power. Power could also be supplied by a battery or implantable power cells that utilize glucose or other means for fuel. The automated expansion could also be achieved by a pump, a syringe type plunger, a piezoelectric crystal, a bellows, a Nitinol motor, a pH responsive material that changes shape, thermal expansion of a gas, fluid or solid (example wax) expansion, magnet forces or any other type automated expansion or compression mechanism.

The control for activating this mechanism could be a remote control using a radiofrequency signal which can pass through tissue. The remote control could also be achieved by magnetic fields, time varying magnetic fields, radio waves, temperature variation, external pressure, pressure during swallowing, pH of any frequency or any other type of remote control mechanism.

Actuation Mechanisms

Figure 37:
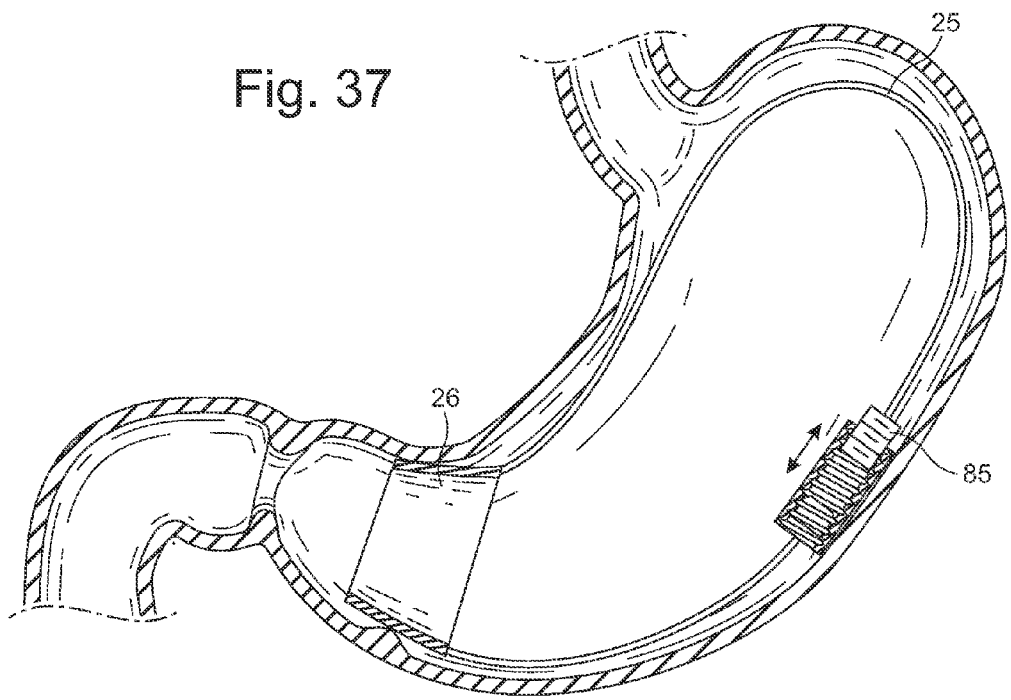
FIG. 37 depicts a cross-sectional side view of an embodiment of the bariatric device of the present invention, located within a cross-section of a stomach.

Stepper Motor:

To adjust the length of the positioning element, 25 to ensure proper seating, the adjusting element could be the positioning element, 25 entirely or partially comprised of a flexible, semi-flexible or rigid screw. A stepper motor 85 could be placed onto the flexible thread and could drive forward or back to allow the positioning element, 25 to draw together or push apart the elements. See FIGS. 37 and 39. These figures represent a threaded element that can be drawn together or apart. These figures also show optional locations of where the lower stomach element may sit in the stomach.

The adjusting element may require power to drive the motor 85. The power could be supplied by an implanted power source such as a battery or it could be powered externally by induction through the coupling of an external antenna and an internal antenna.

Figure 38A:
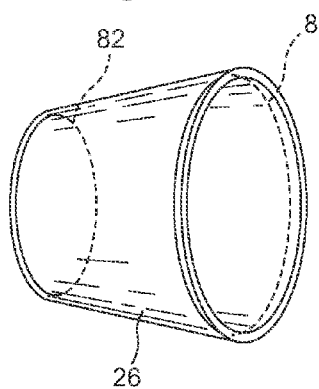
FIG. 38A depicts a side view of an antenna located within an embodiment of the bariatric device of the present invention.
Figure 38B:
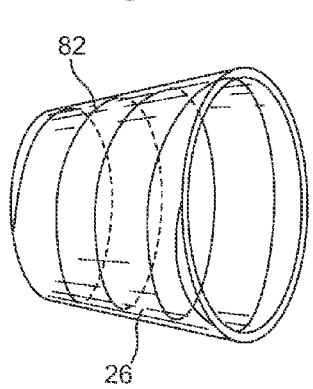
FIG. 38B depicts a side view of an antenna located within an embodiment of the bariatric device of the present invention.
Figure 38C:
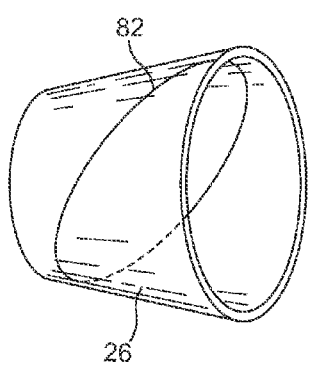
FIG. 38C depicts a side view of an antenna located within an embodiment of the bariatric device of the present invention.

An option would be to embed the internal antenna into any or all of the elements. This would allow for fewer structures in the design by encasing the antenna inside of one or more of the existing elements. FIG. 38A, 38B or 38C show how the antenna could be a simple ring at the top or bottom or obliquely on either element or it could be placed in the wall of the device 10. The internal antenna could also be attached by a tether, free floating inside the esophagus, stomach or intestine. These could be made from materials to make them MRI compatible and/or MRI safe. This feature could be applied towards any actuation method where it is powered by induction.

Figure 40:
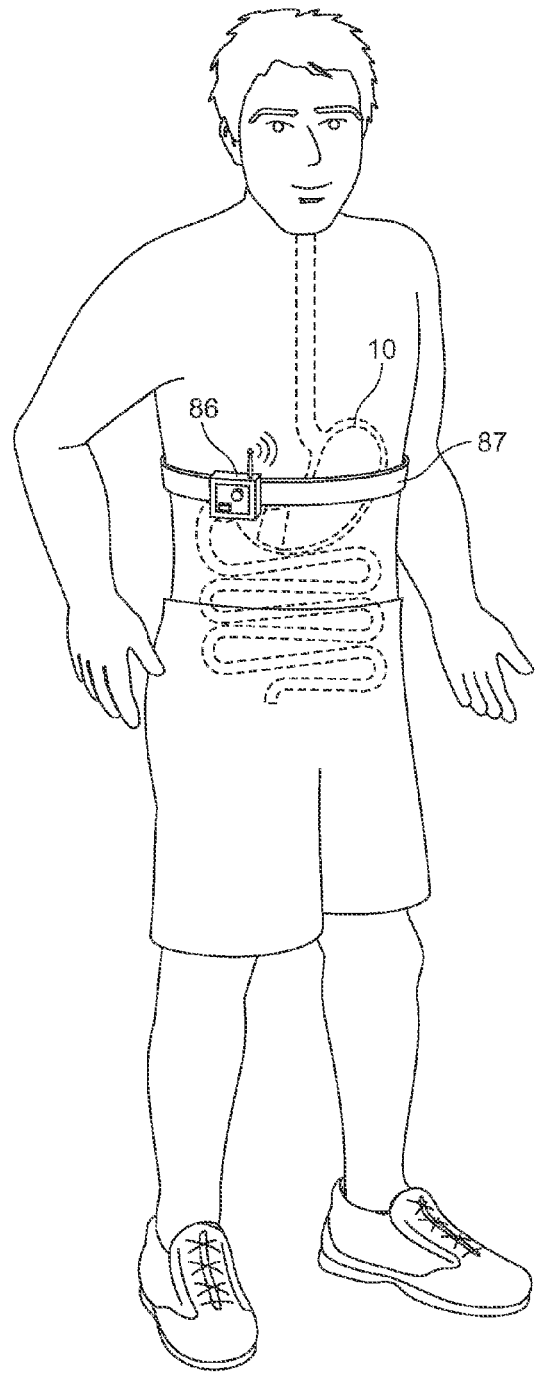
FIG. 40 depicts a remote controller of an embodiment of the present invention, worn next to the user's body.
Figure 41:
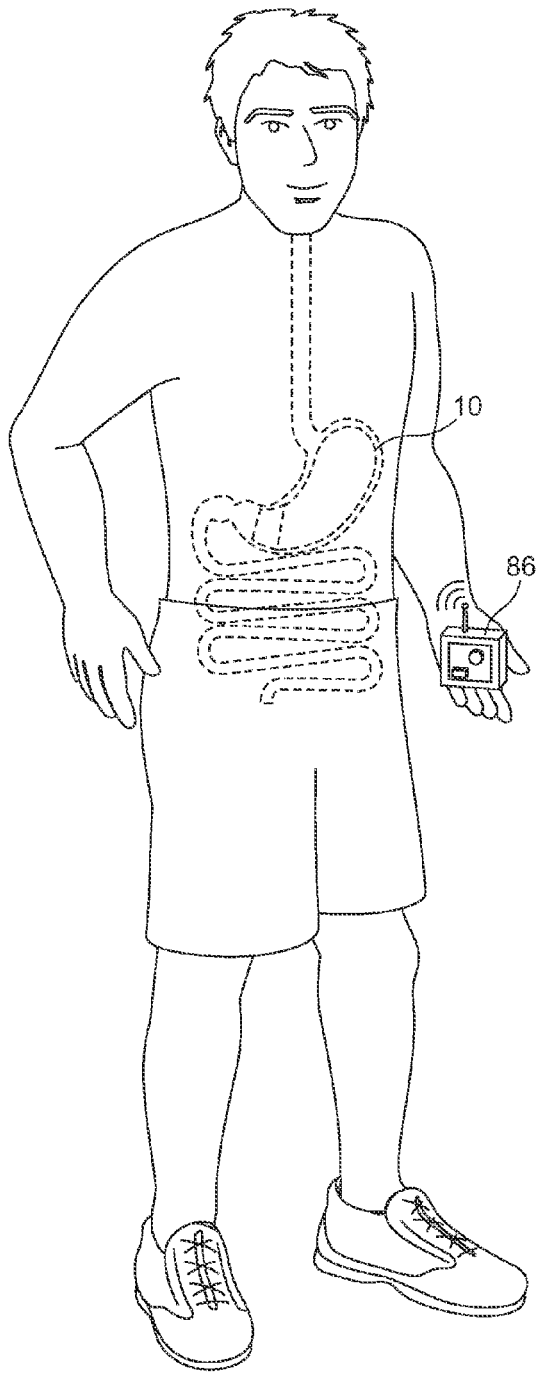
FIG. 41 depicts a remote controller of an embodiment of the present invention, used without wearing or placing adjacent to the body.

For induction, an external hand held controller 86 may be required to transmit power for coupling. See FIGS. 40 and 41. The controller 86 could be set up to auto detect the internal antenna's presence and identify when coupling between the two antennas was adequate to allow for transmission and powering to take place, and to inform the user of function. This external controller 86 could then be used to display the distance that the stepper motor 85 had been advanced or retracted to allow the physician to control the adjustment. Similarly, the external controller 86 could be used for communication and control signals as an interface between the physician and the placed device 10. This feature could be applied towards any actuation method powered by induction.

An external antenna would be required for induction and could be placed into an external handheld controller 86. This could be placed directly against or close to the patient's body preferably at the height of the internal bariatric device 10. The antenna could be housed with the other controller electronics in a single unit. This feature could be applied towards any actuation method powered by induction.

Another alternative would be to have the external antenna in the form of a belt 87 that would wrap around the patients abdomen at the height of the device 10 to better align the antennas for improved coupling. This feature could be applied towards any actuation method powered by induction.

The location of the actuation mechanism could also be inside any of the elements, or above or below any of them, or another location as would be best suited for the anatomy and function of the device 10. This feature could be applied towards any actuation method. Actuation could be accomplished by allowing the screw to be pushed or pulled inside any of the elements to embed the adjustment mechanism internally to one of the other elements. Other actuations mechanisms such as those listed above or others could also be used for this adjustment.

Induction could also be powered by an endoscopic or intragastric instrument. The instrument could have a flexible shaft that could fit through the mouth and down the esophagus or down the working channel of a gastroscope. Once the instrument was placed within or near the esophagus or stomach, it would allow the instrument to be in close proximity with the device antenna and actuation mechanism in the device 10. The end of the instrument could have antenna(e) to allow for inductive powering and/or communication with the actuation mechanism for adjustment. This feature could be applied towards any actuation method.

Piezoelectric Motor

Figure 42:
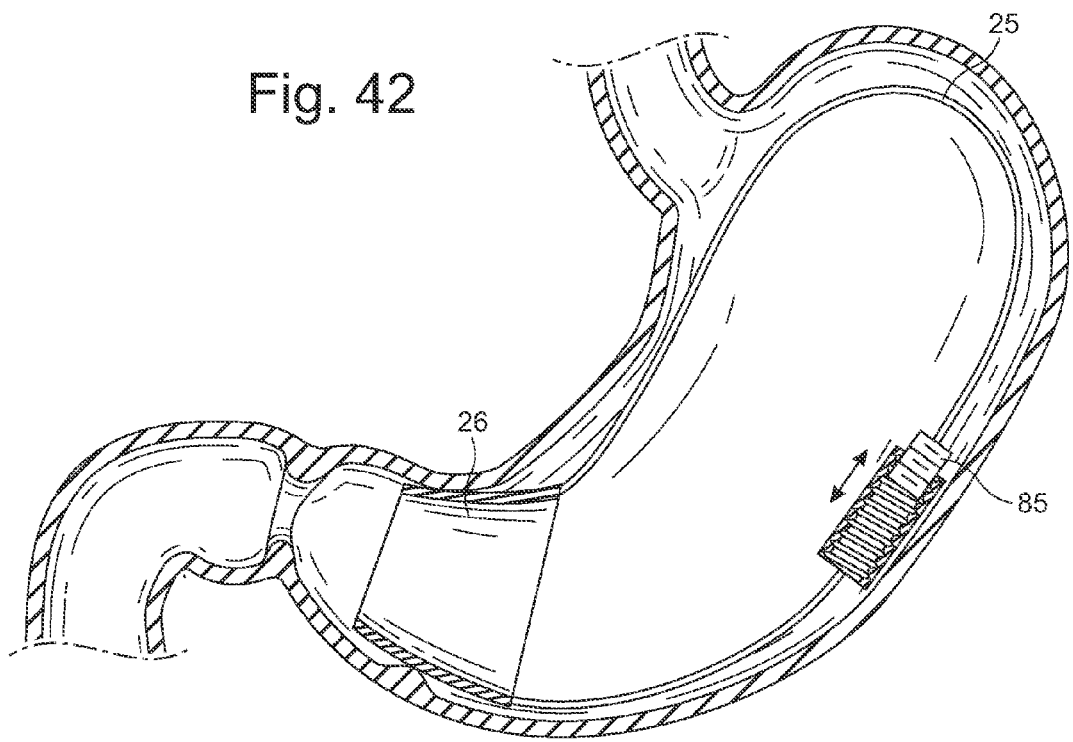
FIG. 42 depicts a cross sectional side view of an embodiment of the bariatric device of the present invention, located within a cross-section of a stomach.

The adjustment could also be achieved by a piezoelectric element or motor 85. See FIGS. 39 & 42. These figures represent a threaded element that can be drawn together or apart.

There are several types of piezomotors that could be used for linear actuation. For example, a motor from NewScale Technologies (www.newscaletech.com) called the Squiggle Motor could be used which is very low profile and can be actuated when powered. Other motors or actuation mechanisms could also be used, and the Squiggle motor is just used as an example. In this example, there is a rigid screw that passes through the center of a threaded piezoelectric "tube" or element. When powered the piezoelectric element flexes side to side along the central axis to create an oscillating "hula hoop" action which causes it to translate axially along the rigid screw. The Squiggle motor could be attached to the positioning element, 25 to advance or retract the lower stomach and positioning element 26, 25. Alternatively, the Squiggle motor could be placed in between any of the elements. Alternatively, more than one Squiggle motor could be placed at these locations. One of the advantages of a piezoelectric motor 85 is that it would allow the device 10 to be MRI compatible and safe. As mentioned with the stepper motor 85 above, the piezoelectric motor 85 could be powered by an internal power source such as a battery or it could be powered by remote induction. The remote induction could be by a handheld external controller or it could be by a gastroscopic instrument placed down the esophagus. This motor could be encased in other materials to keep it dry and protected from the stomach environment.

Another embodiment of a piezoelectric actuated motor 85 would be to have a rotating piezoelectric member that could thread along one or two threaded members similar to a worm gear.

Another embodiment of a piezoelectric actuated motor 85 would be to have a piezoelectric crystal that elongates or flexes to actuate another member.

All of the piezoelectric motors 85 may contain a sealed housing such as an expandable metal, plastic bellows or other to prevent moisture of fluid from contacting the piezoelectric elements.

Magnetic Actuation

As mentioned above in the manual adjustment section, another adjustment mechanism could use magnets. See FIG. 36.

For example, at least a portion of the positioning element could be a semi-flexible thread or rigid thread with a magnetic nut placed over it. Another strong magnet, named a controller magnet 80, could be placed in close proximity to the implanted magnet to cause it to rotate. The rotation of the controller magnet 80 could create a magnetic field which would cause the internal magnet to turn allowing it to advance and retract along the threaded member.

- The controller magnet 80 could either be external to the body or it could be placed on the end of a gastroscopic instrument for close proximity.
- The controller magnet 80 could be a magnet or an electromagnet to increase the intensity of the field and to improve magnetic coupling to ensure actuation.
- The controller magnet 80 could also be multiple magnets to improve magnetic coupling.

Nitinol Actuation

The adjustment element could also be actuated by Nitinol or a substance with similar properties. When a current is passed through Nitinol, it heats and causes the Nitinol to change its shape. Nitinol can expand into a variety of different shapes. A linear actuator could be made from Nitinol to advance or retract along an actuation member.

- Heat could be generated from an implanted battery or it could be delivered by induction, or by direct contact as described above for manual actuation.
- The positioning element could have multiple positional features such as holes, grooves, teeth or a wedging feature. A Nitinol clip could have a feature to engage these positional features. The Nitinol clip could be heated to change shape to allow it to advance or retract into different positional features to increase or decrease the length.
- There are other Nitinol actuations that could be provided as well.

Ultrasound Motor

Another adjustment mechanism could be by use of an ultrasound motor or one powered by external ultrasound. This could use external ultrasound equipment to send sonic waves into the body to actuate the motor. This would also provide an MRI compatible option without requiring an internal power source or induction.

Hydraulic Actuation

The adjustment element 60 takes the form of an inflatable body 77 in FIG. 9A and an inflatable body 68 in FIG. 35B, and is actuated through hydraulic means for radial expansion or linear actuation as previously described. The lower stomach element 26 could be inflated with a fluid to increase the diameter or length of the device 10 to increase pressures against the pyloric region 42. It could increase in volume by accessing a self sealing membrane such as a self sealing drug delivery port, self sealing membrane on the expandable body, or a self sealing valve attached to the device 10. The inflation could be achieved by a piezoelectric pump, a peristaltic pump, a positive displacement pump or a syringe pump.

Piezoelectric pump: The pump could be comprised of a piezoelectric element which can flex to propel fluid directly or a member that could propel fluid. For example, a piezoelectric disk could be captured in a housing with an incoming channel and an outgoing channel. The disk could be powered to cause it to flex into a dome shape to push fluid into the outgoing channel. A valve would be required to close the incoming channel to ensure directional flow to the outgoing channel. Similarly, the piezoelectric Squiggle motor as described above could be used to linearly actuate a fluid up or down a tube to hydraulically actuate position.

Stepper motor pump: Actuation could be achieved by a stepper motor where the motor linearly actuates to compress a reservoir or syringe to move fluid within a tube or constrained volume.

Wax expansion pump: Fluid could also be propelled by a wax expansion mechanism. When wax is heated to melting it expands by approximately 30%. A solid plug of wax could be heated to expand and drive fluid through a valve to hydraulically actuate lengthening. The lengthening structure could be made to move only in one direction, so that when the wax cools it will not contract. The wax expansion could also be used to actuate other adjustment mechanisms.

Peristaltic pump: The members could also be driven by a peristaltic pump. In this mechanism, the external diameter of a cylindrical actuator could be used to compress a length of tubing to create an occlusion. The cylindrical actuator could be rotated along the tube to drive fluid forward or backwards inside the tube. The peristaltic pump could also be actuated by a stepper motor or by a piezoelectric element or other.

Gas expansion/propellant pump: The length could also be actuated by a gas expansion pump where a gas like Freon or others could be used to expand when exposed to a higher temperature. Similar principles to the devices like the Codman pump could be used. This change in volume could drive the pump forward. Similarly, there could be compressed gas constrained in a pressure vessel with a valve. The valve could be remotely activated to allow gas to propel a syringe, fluid or to compress a constrained volume.

Positive displacement pump: There are implant grade positive displacement pumps that are available on the market for drug delivery that could be used to displace a specific amount of fluid for hydraulic inflation of the adjustment element 60.

Syringe pump: A syringe pump could be made by advancing fluid through a syringe. The syringe could be actuated by a stepper motor, a piezoelectric actuator, a magnet or by a Nitinol actuator as described above.

Hydrogel: the adjustment element could also be inflated by use of a hydrogel to absorb fluids and could be actuated by changes in temperature, pH or tonicity to change shape or volume Hypertonic fluid: the adjustment element 60 could also be inflated by using a hypertonic fluid in the inflation area and allowing it to absorb fluid across a semi permeable membrane.

Mechanical means for diametrical changes. Similar to the inflation, elongation, and shortening embodiments described above, the device 10 could change diameter by various actuation mechanisms. All of the above-described mechanisms could also be adapted for use for a diametric change instead of a linear change.

As a variation of the embodiments discussed above, the device 10 could have a sensor 88 that could sense a parameter such as pressure, motion, peristalsis, tension, pH, temperature, chemical or other appropriate parameters, or various parameter combinations. The sensor 88 could output a signal to be used by an actuation element to actuate an adjustment element, to a memory element such as a microchip, or be read by a remote reader or remote controller.

Figure 39:
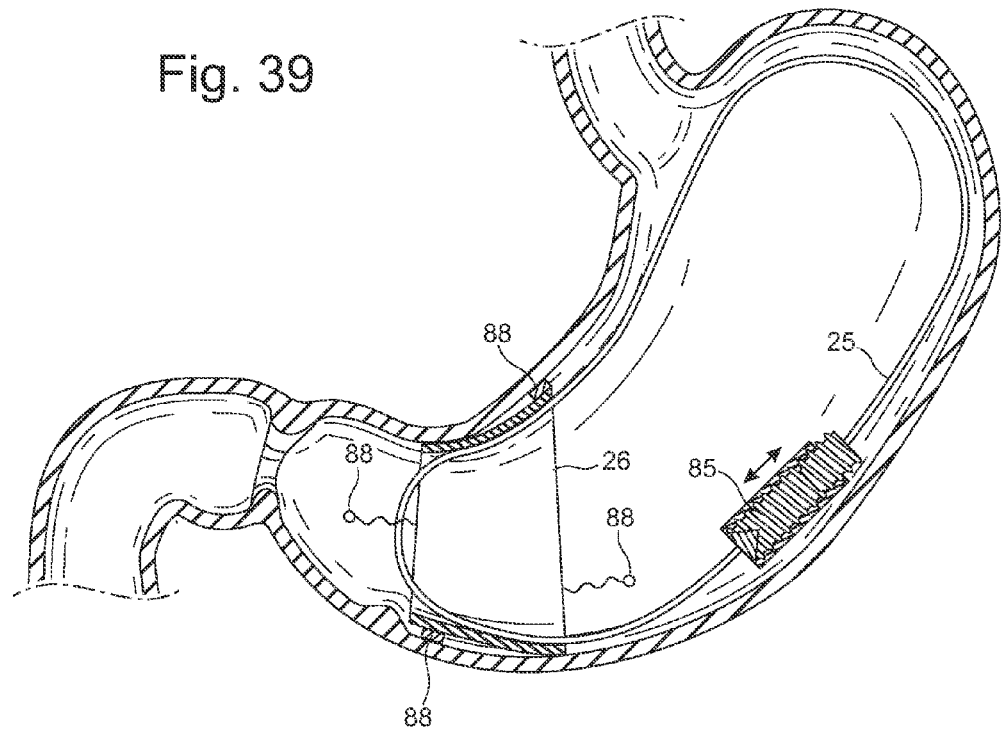
FIG. 39 depicts a cross sectional side view of an embodiment of the bariatric device of the present invention, located within a cross-section of a stomach.
Figure 43:
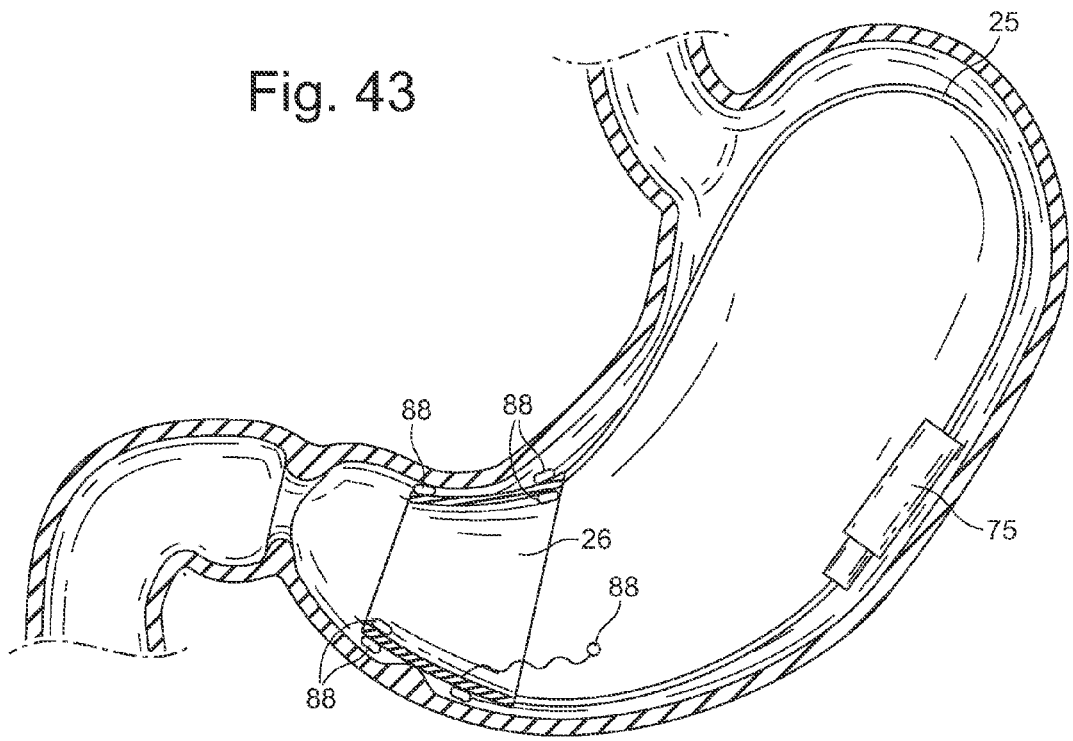
FIG. 43 depicts a cross sectional side view of an embodiment of the bariatric device of the present invention, located within a cross-section of a stomach.

Sensors 88 could be used to gather important patient data to understand performance, patient status or whether an adjustment needs to be performed. For ease of use and compatibility with the body, wireless sensors would be preferred. The sensors 88 could be direct tissue contact, intermittent patient contact or could monitor the intraluminal pressure inside GI tract. The data could be used for no other reason than to just monitor patient status. FIGS. 39 and 43 depict sensors 88, which could be embedded in any of the elements or it could be tethered to any of the elements to allow it to be suspended inside the GI tract. Based on the sensed parameter, the device 10 could be adjusted. The adjustment could have an open or closed loop system increasing or decreasing the applied force, pressure or sensed parameter. The sensed parameter could detect whether the device 10 was not at an ideal condition, and could then send a signal to a control mechanism for automatically adjusting the system. This mechanism could be under physician control (open system) or without physician control (closed system). The adjustment could also be a manual adjustment where the parameters are being monitored to guide the adjustment. It could also control the shape of the lower stomach, and/or positioning elements 26, 25 to vary stiffness, size, length, form or shape. In general, the sensor 88 could sense a parameter and then adjust the device 10 as needed to bring the sensed parameter into the ideal range. There could be an algorithm that controls the ideal parameter or it could be based on a parameter range. The device 10 would be adjustable to meet the needs of the patient.

In an open loop system, the physician would have control of when the device 10 would adjust. The device could have it owns internal power source or the device 10 could be passive and only inductively powered when in close proximity to an external controller under the supervision of a physician. For example, in the clinic the physician could have a remote controller with the ability of powering the device 10 inductively, and then begin to monitor the sensors feedback signals to see physical parameters of the patient at baseline such as pressure of the device 10 against the lower stomach. The sensor monitoring could also be performed while the patient is eating or drinking, or not eating or drinking. As the patient consumes, the esophageal and stomach peristaltic waves will increase in intensity as they propel the food or drink from the mouth to the stomach. A sensor 88 could detect when these waves increase in amplitude, frequency, and pressure. The parameter could read on the external controller by the physician, and then the physician could send a signal to the automated expansion mechanism in the device 10 to adjust the device. The physician could then query the sensor 88 again to determine whether the device 10 was in the ideal settings and whether the pressure against the stomach or sensed parameter was optimized. The physician could iteratively control the amount of adjustment and monitor the parameters until the ideal condition was met. Where the device has its own power source, the physician may still have the control to wake up the device, query the sensors and then adjust the device as described above. The only difference would be that the device was powered by the power source and not require inductive power from outside.

Alternatively, the physician could read the parameter signals while under his supervision, but have the sensors 88 send a signal directly to the automated expansion mechanism to adjust until the device 10 was within the ideal parameters. The data collected could be analyzed by the controller for averages, minimums, maximums and standard deviations over time and use an algorithm to determine the ideal settings. The controller could then monitor and adjust on its own until the ideal conditions were met, but while the physician was present to verify all conditions and verify patient acceptance.

In a closed loop system, the device 10 would be active with its own integrated power source. The device 10 could wake up at routine intervals to monitor or could monitor all the time. The data collected could be analyzed for averages, minimums, maximums and standard deviations over time and use an algorithm to determine the ideal settings. As the patient begins to consume food or drink, the device sensors 88 would detect the sensed parameter and signal the automated expansion/contraction mechanism to adjust the device 10 as needed. In this embodiment, the device 10 could be fully automated and would not require intervention from an outside individual. This could also be performed when the patient is not eating, but during another point of interest during the day.

In either the open or closed loop system, there could be multiple sensors 88 on the device 10 to determine the pressure or force areas, or other sensed parameters on the device 10 and where it needs to be varied to meet the ideal conditions for the stomach. In the case where the positioning element 25 has multiple components, this could be used to align the device 10 in the stomach to provide a custom fit for each person. There could also be a mechanism to adjust the alignment of the first of lower stomach elements 12, 26 relative to the positioning element 25. The sensor(s) 88 could have a built in power source or it could have a remote power source such as induction so that it would only wake up and activate when an external controller was brought near, or it could have a combination of both internal and external powering sources.

The device 10 could have integrated memory to allow storage of patient and device 10 data. This could include but is not limited to the serial number, the patient's information such as name, patient number, height, weight; the physician's name, the adjustment history including the date and time, the amount adjustment and the sensed parameters. For the active device, there could be 24 hour data recording of key parameters or there could be data collected at key intervals throughout the day to detect when the patient is eating and whether they are being compliant with their eating. It could record weight tracking, BMI or other data as needed which could be queried by an external controller. This data could also be downloaded into a physician's patient tracking database for ease of patient tracking. Similarly, this data could be downloaded and tracked on an internet tracking website, where the patient could log on and see their history and progress. The patient could add information to the website such as weight or an eating log, adverse events or other conditions that the physician or patient would like to track.

In the open system, the physician could choose to collect and record data as needed at the time of the adjustment such as weight, date, time, and adjustment amount or other.

For an open loop system, the device 10 could be adapted to allow for remote adjustments over the phone. This would be especially advantageous for patients living in rural areas where they are far from their physician's office. It could also be for convenience of having an adjustment without having to travel to the physician's office. This would allow a physician to discuss the patient's progress with the patient directly and then query the device sensor 88 to see how the device performance is. Based on the feedback of the device 10, the physician could then adjust the patient.

In yet another embodiment, the device 10 could have an emitter element for dispensing a drug, hormone or bioactive agent to further induce satiety, weight management or other disease management such as diabetes. As used in the claims, the term bioactive agent includes all of these substances. The drug could be a weight management drug currently on the market or one to be developed. Similarly, it could be a satiety hormone or other bioactive agent. In the published literature, there is a growing mass of information on satiety hormones. The bioactive agent could be applied by the emitter element through a drug eluting coating, a reservoir with a pump, or a permeable membrane placed on the device 10 where the drugs could pass from the device 10 into the gut. The emitter element could release such substances in response to a signal from a sensor 88, a timed basis, or other release criteria. The device 10 could have a tube that trails into the intestines to allow the drug to be delivered downstream where the pH is higher and would not destroy the bioactive agent.

The device 10 could have a surface finish or macrotexture for gripping the stomach. If the device 10 could grip the inner mucosa of the stomach, it could elongate or expand to further stretch the stomach in key areas to induce further satiety as needed. For example, the lower stomach element 26 could be a conical spiral with a surface texture that lightly grips the mucosa and or stomach musculature. If the spiral were made of Nitinol or other temperature-sensitive substance, the device 10 could expand the spiral by a variation of temperature. By applying a temperature variation, such as by drinking a hot liquid or otherwise, the device 10 could expand and cause a satiety response. The surface could be multiple protuberances, barbs, a rough bead blast, or other finishes suitable for gripping the stomach wall.

Figure 44:
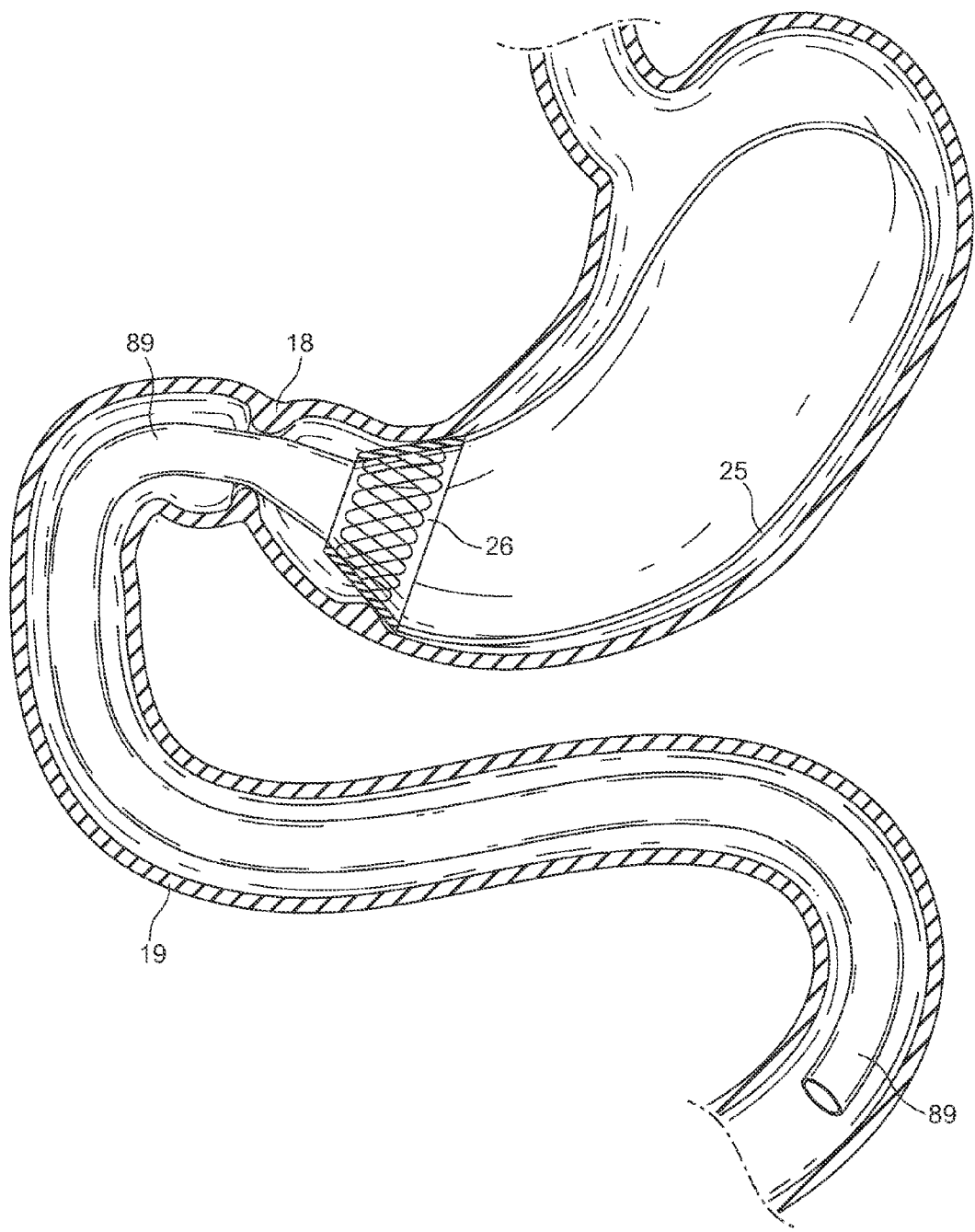
FIG. 44 depicts a side view of an embodiment of the bariatric device of the present invention, located within a cross-section of a stomach and a duodenum.

As a variation of the concepts above where, the device is intended to maintain its relative position in the stomach, the device could have a thin flexible tube attached to the device that could trail into the duodenum to act as a barrier to food absorption. See FIG. 44. This tube would be of similar diameter to the duodenum and all food passing through the device would pass directly into this sleeve. Similar to the rerouting performed in a gastric bypass or Roux en Y bypass, the sleeve would be approximately 100 cm long, but could be longer or shorter depending on the amount of malabsorption required. This tube may be made of an acid resistant material such as Teflon, PTFE, ePTFE, FEP, silicone, elastomers or other acid resistant materials.

As a variation of the device 10, it could incorporate electrical stimulation to the stomach musculature, stomach nerves or the vagus to further improve satiety stimulation and weight loss. Energy used for this stimulation could be RF, ultrasound, microwave cryogenic, laser, light, electrical, mechanical or thermal. The device 10 could have leads incorporated that could embed into the stomach wall or be surgically placed around a nerve, or the stimulation could be applied directly through surface contact of the device 10 to the stomach mucosa.

In yet another embodiment, the bariatric device 10 may have an adjustment element 60 that is equipped with a temporary expansion/contraction element that may allow for temporary adjustment based on activation of a material property, sensor 88 or mechanism of the device 10. This could be applied to any of the above-discussed embodiments. It may be desirable for the temporary expansion/contraction element to adjust only upon eating, and then retract after eating. It may be desirable for the device 10 to adjust with the pH cycle of the patient where pH will be higher prior to eating and then lower after eating. This would allow for intermittent stimulation of the stretch receptors to avoid receptor fatigue over time. For example, the material could be heat sensitive using materials such as Nitinol, which could expand after consuming a hot liquid. Similarly, the device 10 could have a sensor 88 or material that is pH or glucose sensitive or detect the presence of food, which could activate the temporary expansion/contraction element to expand when a certain threshold for pH has been reached or glucose or fat is present after eating. Similarly, this temporary expansion/contraction element could be activated by a magnetic field such as swallowing a magnetic pill that could temporarily expand the device 10. In this example, the magnetic pill would be small enough and shaped appropriately for passage through the gastrointestinal tract, and biocompatible. The patient could consume the electromagnetic pill when a satiety signal was desired. It may also be desirable for the device 10 to adjust based on time or sleep cycle such that the device 10 adjusts at specific times of the day or when the patient lays horizontal. Other parameters or mechanisms to trigger the temporary expansion could be used.

Placement

As mentioned above, a tube, catheter, or sheath may be required to protect the anatomy during placement of the device 10 down the esophagus and into the stomach. It could be a simple flexible tube such as silicone or urethane tube to aid in straightening and compressing the device 10 while it is being introduced. Insertion of the device 10 into the tube would require compression of the device 10 into a narrow, insertable shape. A standard gastroscopic tool could be used to push or pull the device 10 down the tube. Similarly, a custom gastroscopic tool or sheath could be used to introduce the device 10 into the stomach through the esophagus or other narrow opening.

A delivery sheath 91 may be used to insert the device 10 though the esophagus 32 or other narrow opening into the stomach for placement. In one such embodiment, a lightweight fabric, sheeting or material 92 may be used for the sheath 91, made of a suitable material that is thin, flexible, soft, smooth, compliant, adequately lubricious to slide down the esophagus 32 and adequately strong to hold the device 10 in a compressed state 93 such as fabrics made from polymers such as nylon, teflons, eptfe, polyester, or polymer coated fabrics such as ptfe coated cotton or other fabrics or other sheeting materials. Although a fabric could be used for the material 92, other substances may be used, such as silicone, polyurethane, thin walled plastic or other suitable substances. First, the bariatric device 10 may be compressed into a narrow shape to fit inside the sheath 91, and held in a compressed state by a tube, fixtures, or the like. Then the material 92 may be draped around the compressed device 10 lengthwise, and secured in a closed position with a deployment member 94. The material 92 could also be closed with a deployment member 94 and the collapsed device 93 then inserted inside the closed sheath 91. The deployment member 94 could be a small gauge wire or lace placed in a single straight stitch along the length of the material 92 around the compressed device 93, as shown in FIGS. 45 and 46. The deployment member 94 may be of any of a variety of suitable materials. In a preferred embodiment, the deployment member 94 is a single thin wire, preferably capable of holding its original shape even after being bent. Such wire could be made of Nitinol, spring steel, small diameter braided cable or spiral wound guide wire, or other suitable material. Although a deformable wire could be used, it may be more difficult to remove for placement if the bends become too extreme during handling. The deployment member 94 may also be thread material, such silk, rayon, nylon, polyester, eptfe thread, ptfe coated thread and the like. The deployment member 94 may be terminated by stitching the deployment member 94 around the distal end (the end inserted into the body first) of the material 92 to close the distal end of the sheath 91, and turned back around and inserted inside the material 92 towards the proximal end.

Alternatively, the distal end of the deployment member 94 may be secured in a pocket attached to the interior or exterior of the material 92 at or near the distal end of the sheath. For the deployment member 94 such pocket may be in the form of a plastic cap, silicone cap or other suitable material that will protect the wire end from poking or snagging tissue during placement. In such an embodiment, the distal end of the material 92 may be folded over towards the proximal end like an envelope so that the deployment member 94 may secure the distal end of the sheath material 92 without having to stitch around the end. The pocket may then be attached to the material 92 at or near the fold.

The deployment member's proximal end 96 may extend far enough so that it may be accessed outside the patient after the device 10 is placed into the deployment position in the stomach. Preferably, a thin tube 95 made of silicone or plastic is secured to the proximal end of the material 92, and the deployment member 94 is routed inside the tube 95. Such a tube 95 may be independently secured to the material 92 so that the distal end of the tube 95 is just inside the proximal end of the material 92. Then the compressed device 10 may be placed within the material 92 and secured with the deployment member 94. The result is a package with a compressed device 93 inside the closed material 92 and a tube 95 also secured inside the proximal end of the material 92, with the deployment member 94 running through the tube 95. For adequate stiffness for placement, an additional guidewire may be needed to be placed down the center the sheath assembly.

For placement, such a sheath package is placed into the esophagus 32 or other narrow opening or surgical incision, and routed into the stomach. Once in deployment position, the deployment member 94 is pulled through the tubing 95, which releases the closure of the sheath. The device 10 will then expand or regain its operational shape. Then the tube 95, along with the material 92, may be removed from the patient leaving only the device 10 in place.

The delivery sheath 91 may be used for any delivery of any medical device through a narrow opening. If the medical device is naturally narrow, or can be compressed, deflated, or other means of holding it in a narrow shape, it may be placed in a delivery sheath 91 as discussed above. After the deployment member 94 is pulled through the tubing 95, the medical device may expand or rebound into its operational shape, whether by its construction of shape-retaining materials, or by mechanical, hydraulic, pneumatic, or other means.

Removal

For removal, a flexible tube such as a standard overtube could be used with a standard or custom endoscopic tool. The tube may be placed down the esophagus and a gastroscope and the tool then placed down the lumen of the overtube. A standard tool such as a grasper or snare could grasp the device 10 and pull it up the tube. The device 10 would be straightened by the overtube for removal from the stomach and esophagus.

Figure 47:
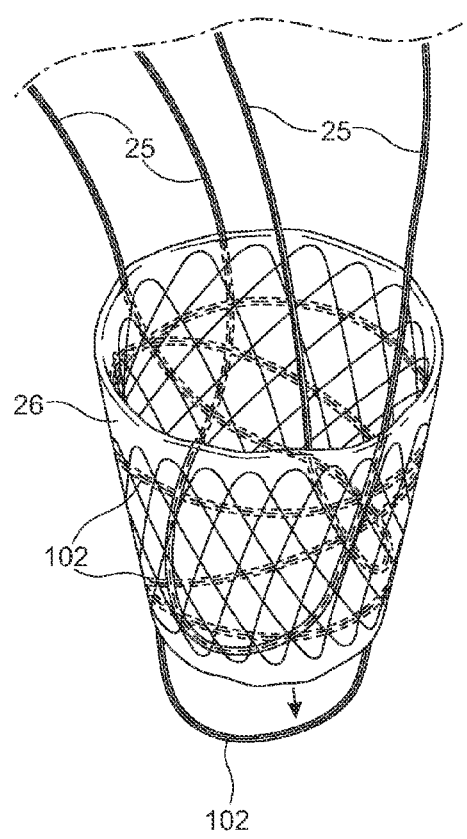
FIG. 47 depicts a perspective view of a lower stomach element equipped with a constriction element, in an embodiment of the present invention.
Figure 48:
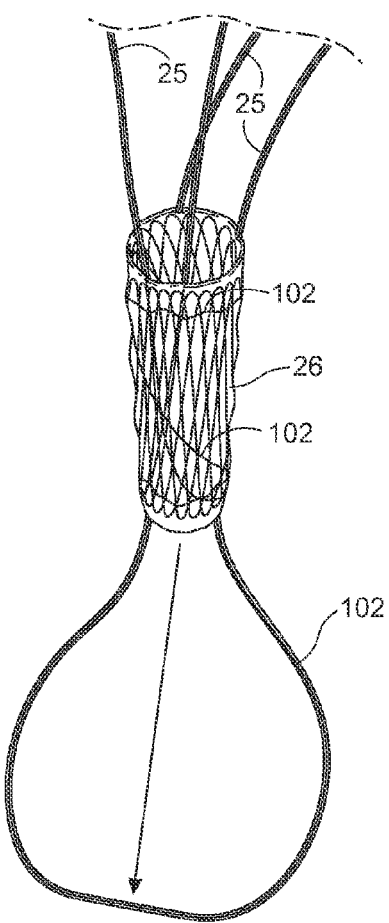
FIG. 48 depicts a perspective view of the lower stomach element shown in FIG. 47, with the constriction element engaged to constrict the pyloric element.

In another embodiment, the elements may incorporate a collapsing mechanism designed to collapse the element into a compact shape for removal. For example, FIGS. 47 and 48 depict a lower stomach element 26 with a constriction member 102 comprising a wire or thread sewn spirally around, through, or inside the length of the element. The constriction member 102 could also be sewn through eyelets or features attached to the inside of the lower stomach and/or positioning element 26, 25. The ends of the constriction member 102 may be connected. When the constriction member 102 is pulled, it tightens the circumference of the lower stomach element 26 like a drawstring, which collapses the element down to a narrow profile that can be safely removed through the esophagus or other narrow opening, or ease its placement into a tube for removal. Similar collapsing mechanisms can be installed in the first, second or positioning elements 12, 13, 25. The constriction member 102 could be made from Nitinol, stainless steel wire, PTFE thread, ePTFE thread or ptfe coated threads or other suitable materials. The constriction member 102 could be integrated into the elements in a variety of patterns such as a continuous spiral, two spirals of reversing orientation, or other.

Figure 49A:
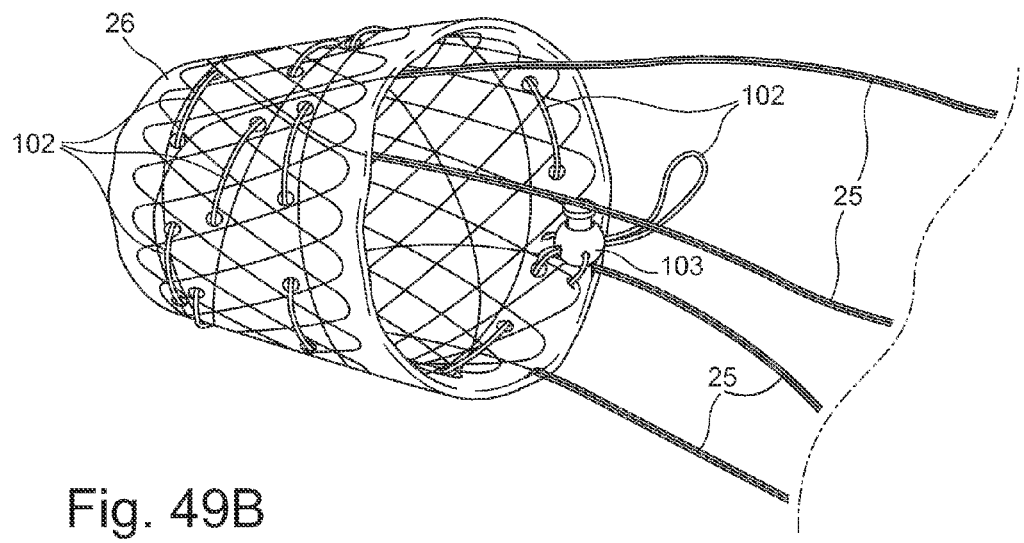
FIG. 49A depicts a perspective view of a lower stomach element equipped with a constriction element with a mechanical stop, in an embodiment of the present invention.
Figure 49B:
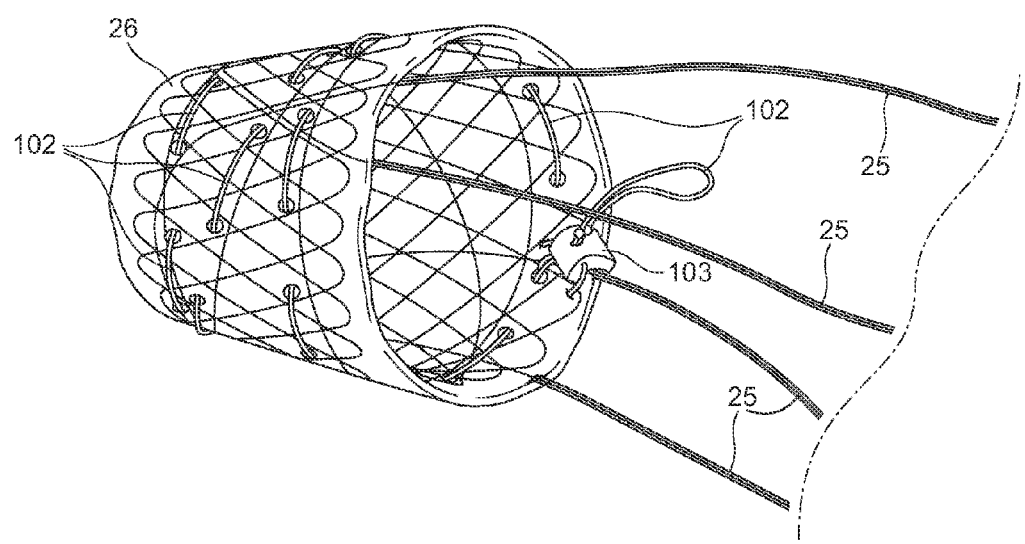
FIG. 49B depicts a perspective view of a lower stomach element equipped with a constriction element with a mechanical stop, in another embodiment of the present invention.
Figure 50:
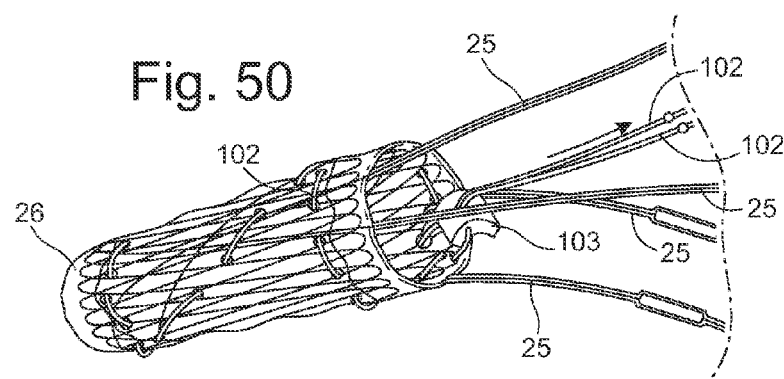
FIG. 50 depicts a perspective view of the lower stomach element shown in FIG. 49B, with the constriction element engaged to constrict the lower stomach element.

The constriction member 102 may also be threaded through a retaining element 103 to aid in maintaining the collapsed position such as a drawstring cord stop or the like. See FIGS. 49A, 49B and 50. This figure shows a stop element that is affixed to the lower stomach element 26 and the constriction member is threaded through. For example, this mechanical stop 103 could be a thick sheet of silicone with a slit or small hole punched through the center section, and the retrieval drawstring is pulled through the opening. When the constriction member 102 is pulled, it is drawn through this stop element 103 and the mechanical stop applies resistance to the retrieval drawstring to hold the device 10 in the collapsed state. To further improve the holding capacity of the mechanical stop 103, a feature could be added to the retrieval drawstring 102 such as a knot tied or an arrowhead or bead attached to the drawstring that allows the feature to be pulled through the slit of the mechanical stop 103, but creates a mechanical interference to prevent the drawstring from pulling back through the stop. The mechanical stop could also be a cord stop 103 as shown in FIG. 49A.

In another embodiment, the connection of the lower stomach and positioning elements 26, 25 may be equipped with a release element, which would allow the lower stomach and/or positioning elements to be releasable, cut-able or modular, as to allow the device to be disassembled into components for ease of removal. FIGS. 51, 52A and 52B show a release element in the form of a releasable clip 108 in the closed and open positions. The clip could be made of an elastomer or polymer or other, but would need adequate flexibility to allow the clip to close and then re-open. The clip has a locking tooth 109 which compresses when pulled through a narrow channel 110, and then expands into an opening to lock the clip into position. To release the clip, the release tab 111 is pulled upward which allows the narrow channel to flex open, and the locking tooth 109 is released. FIG. 51 shows as side view of the releasable clip in the locked position in a suggested location to attach a positioning element to another element. A release element like this could be bonded or incorporated into the lower stomach elements and then could be locked around the positioning element to secure the assembly. When the device is ready for removal, standard instruments could be used as a releasing tool under the visualization of a gastroscope to release the tabs to disassemble the lower stomach 26 element 12 from the positioning elements 25. Then each element or combination of elements could then be removed up the esophagus or through an over tube. As described above, the lower stomach element could still contain a collapsing member to further collapse the element for removal. The connections could be placed over a single section of the positioning element or it could be placed over a joint to join two positioning elements. The connection length could be a short distance or it could be a relatively long distance. With a short distance, several clips could be used to join a positioning element to a lower stomach element such as shown in FIG. 53A. With a long element, one clip could feasibly connect the two elements such as shown in FIG. 53B. FIGS. 53A and 53B show an example of release elements where the modular clips could be used to connect the lower stomach and positioning elements, 25, 52. These are only examples of where a connection could be located, but other locations could be used. Similarly, this modular clip only shows one type of clip, but several other options could be used.

The modular connection of the components could be equipped with release elements comprising many different mechanisms such as other clip designs, ties and could also provide an area where the connection is to be cut by a releasing tool, such as endoscopic scissors or electro-cauterizer, or other custom tools. In another embodiment, the positioning elements could be sewn into the lower stomach element with acid resistant thread such as ePTFE thread and/or cloth. The thread or cloth could be cut by a releasing tool such as surgical scissors or an electro-cauterizer for removal. The connection could be made of many different materials such as silicone, Nitinol, polymers, super alloys, or other suitable materials that can withstand the acidic environment of the stomach. Likewise, the releasing tool could be many different endoscopic instruments.

Several features are described in the embodiments above and the scope of this specification allows that any feature or combination of features may be combined with another other feature. Although these combinations may not be expressly described or shown in the drawings, it is covered under the scope of this invention. For example, any lower stomach, first or second element 26, 12, 13 may be combined with any restriction element, stiffening rib 31, positioning element 25, adjustability feature, peristaltic accommodation feature or other technology.

The foregoing description of the preferred embodiments of the invention has been presented for the purposes of illustration and description. It is not intended to be exhaustive or to limit the invention to the precise form disclosed. Many modifications and variations are possible in light of the above teaching, including but not limited to the mixing and matching of various elements described herein. It is intended that the scope of the invention not be limited by this detailed description, but by the claims and the equivalents to the claims appended hereto.

INDUSTRIAL APPLICABILITY

This invention may be industrially applied to the development, manufacture, and use of bariatric devices for weight loss purposes.

What is claimed is:

1. A bariatric device for weight loss, comprising
   a. a lower stomach element comprised of a wall forming a lumen, the wall having an interior surface, an exterior contact surface comprising a steep-sided frusto-cone adapted to fit the walls of the mid to lower stomach, and wherein the lower stomach element is constructed of resilient material capable of being collapsed for placement and rebounding to maintain its shape for operation, and sized to prevent the lower stomach element from contacting the pylorus;
   b. a positioning element with proximal and distal ends, comprising two closed loops arranged in separate planes, wherein the distal ends of the loops are coupled with the lower stomach element, and the proximal ends are adapted to engage the upper stomach, wherein the positioning element is constructed of resilient material such that the proximal end is capable of contacting on the upper stomach to maintain the relative position of the lower stomach element to cause the lower stomach element to have at least intermittent contact with the mid to lower stomach; and
   c. a restriction element coupled with the lower stomach element.

2. The bariatric device of claim 1, wherein the two loops are aligned to be generally parallel as they extend from the lower stomach element.

3. The bariatric device of claim 1, wherein the two loops intersect at a joint between the distal and proximal ends to form a figure-8 structure.

4. The bariatric device of claim 1, further comprising a stiffening rib coupled with the positioning element and extending towards the proximal ends of the loops.

5. The bariatric device of claim 4, wherein the stiffening rib comprises a wire loop with ends terminating in the joint.

6. The bariatric device of claim 1, further comprising an anti-migration element coupled with the lower stomach element, wherein the anti-migration element is of sufficient size and resistance to prevent migration of any part of the lower stomach element past the pylorus.

7. The bariatric device of claim 1, wherein the restriction element is an inflatable body.

8. The bariatric device of claim 1, wherein the inflatable body further comprises an inflation element to vary the degree of inflation to expand or reduce the size of the restriction element.

9. The bariatric device of claim 1, wherein the restriction element comprises a multiple loop structure.

10. The bariatric device of claim 1, wherein the restriction element comprises one or more ribs arranged in a radial pattern from the interior surface of the lower stomach element.

11. The bariatric device of claim 1, wherein the restriction element comprises a valve.

12. The bariatric device of claim 11, wherein the valve is actuated by peristalsis.

13. The bariatric device of claim 1, wherein the restriction element comprises multiple flexible members that cross the interior of the lower stomach element.

14. The bariatric device of claim 1, wherein the restriction element comprises a reduced lumen within the lower stomach element.

15. The bariatric device of claim 1, wherein the restriction element slows gastric emptying.

16. The bariatric device of claim 1, further comprising a weight coupled with the lower stomach element to preferentially orient the lower stomach element in the mid to lower stomach.

17. The bariatric device of claim 1, wherein the lower stomach element and positioning element are constructed to allow the lower stomach element to unseat and reseat in response to peristalsis.

18. The bariatric device of claim 1, wherein the restriction element causes an increase in pressure to the upper stomach and a satiety signal.

19. The bariatric device of claim 1, wherein the contact of the lower stomach element to the stomach wall alters peristalsis.

20. The bariatric device of claim 1, further comprising a lumen coupled with the lower stomach element, said lumen extending past the pylorus and into the duodenum, to prevent food absorption in the upper portion of the intestine.

21. The bariatric device of claim 1, further comprising an adjustment element coupled with the positioning element to adjust the sizing of the positioning element.

22. The bariatric device of claim 21, wherein the adjustment element comprises at least one positional feature held in a retainer.

23. The bariatric device of claim 21, wherein the adjustment element comprises a locking ring which movably engages a positional element.

24. The bariatric device of claim 21, wherein the adjustment element comprises male and female threaded members.

25. The bariatric device of claim 21, wherein the adjustment element comprises an expandable joint.

26. The bariatric device of claim 21, wherein the adjustment element comprises an inflatable body coupled with the lower stomach element.

* * * * *